United States Patent
Ruschel et al.

(10) Patent No.: US 11,098,308 B2
(45) Date of Patent: Aug. 24, 2021

(54) TREATMENT OF CNS INJURY WITH RNAI THERAPEUTICS

(71) Applicant: BioAxone BioSciences, Inc., Cambridge, MA (US)

(72) Inventors: Joerg Ruschel, Cambridge, MA (US); Lisa McKerracher, Boston, MA (US); Emily Niederst, Cambridge, MA (US); Kenneth M. Rosen, Milton, MA (US)

(73) Assignee: BioAxone BioSciences, Inc., Boston, MA (US)

( * ) Notice: Subject to any disclaimer, the term of this patent is extended or adjusted under 35 U.S.C. 154(b) by 0 days.

(21) Appl. No.: 16/321,229

(22) PCT Filed: Jul. 27, 2017

(86) PCT No.: PCT/US2017/044235
§ 371 (c)(1),
(2) Date: Jan. 28, 2019

(87) PCT Pub. No.: WO2018/022927
PCT Pub. Date: Feb. 1, 2018

(65) Prior Publication Data
US 2020/0032268 A1 Jan. 30, 2020

Related U.S. Application Data

(60) Provisional application No. 62/367,199, filed on Jul. 27, 2016.

(51) Int. Cl.
*C12N 15/113* (2010.01)
*A61P 27/02* (2006.01)
*A61P 25/00* (2006.01)

(52) U.S. Cl.
CPC .......... *C12N 15/1137* (2013.01); *A61P 25/00* (2018.01); *A61P 27/02* (2018.01); *C12Y 301/03067* (2013.01); *C12N 2310/14* (2013.01); *C12N 2310/315* (2013.01); *C12N 2310/344* (2013.01); *C12N 2310/346* (2013.01); *C12N 2310/3515* (2013.01)

(58) Field of Classification Search
CPC ............ C12N 15/1137; C12N 2310/14; C12N 2310/315; C12N 2310/344; C12N 2310/346; C12N 2310/3515; A61P 27/02; A61P 25/00
See application file for complete search history.

(56) References Cited

U.S. PATENT DOCUMENTS

2009/0305333 A1* 12/2009 He .................. A61K 31/28
435/29
2013/0131141 A1 5/2013 Khvorova et al.

FOREIGN PATENT DOCUMENTS

WO WO-2009/149435 A2 12/2009
WO WO-2010/033247 A2 3/2010

OTHER PUBLICATIONS

Blesch et al., "Spinal cord injury: plasticity, regeneration and the challenge of translational drug development," Trends Neurosci. 32(1):41-7 (2009).
Christie et al., "PTEN inhibition to facilitate intrinsic regenerative outgrowth of adult peripheral axons," J Neurosci. 30(27):9306-15 (2010).
Du et al., "Pten Deletion Promotes Regrowth of Corticospinal Tract Axons 1 Year after Spinal Cord Injury," J Neurosci. 35(26):9754-63 (2015).
International Search Report for International Application No. PCT/US2017/044235, dated Dec. 11, 2017 (4 pages).
Written Opinion for International Application No. PCT/US2017/044235, dated Dec. 11, 2017 (6 pages).
Zukor et al., "Short hairpin RNA against PTEN enhances regenerative growth of corticospinal tract axons after spinal cord injury," J Neurosci. 33(39):15350-61 (2013).
International Preliminary Report on Patentability for International Application No. PCT/US2017/044235, dated Feb. 7, 2019 (10 pages).

* cited by examiner

*Primary Examiner* — Richard A Schnizer
(74) *Attorney, Agent, or Firm* — Clark & Elbing LLP

(57) ABSTRACT

Self-delivering PTEN RNA and methods of reducing PTEN expression are provided herein. Also provided are methods of treating spinal cord injury (SCI) and other neurotrauma with PTEN sdRNA.

16 Claims, 56 Drawing Sheets
Specification includes a Sequence Listing.

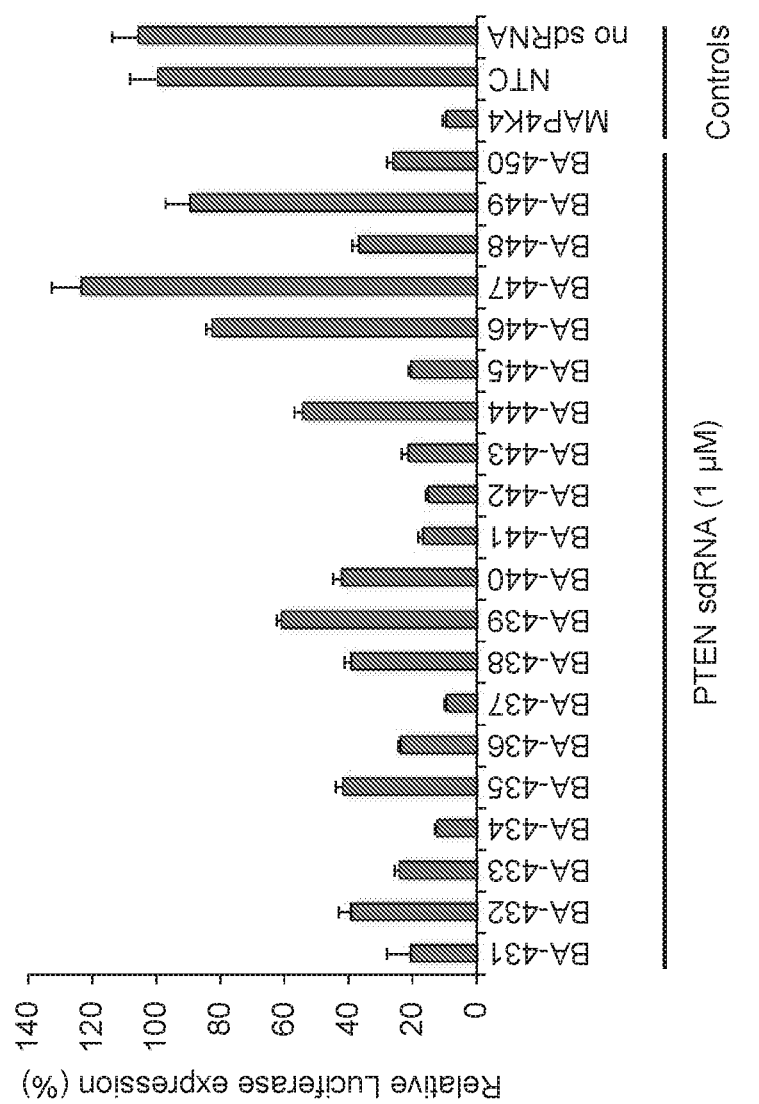

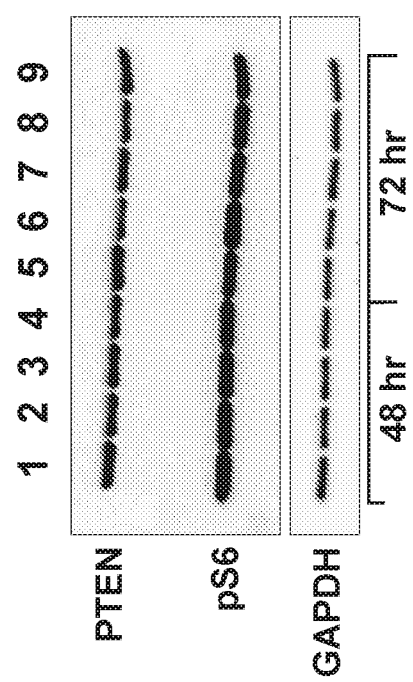

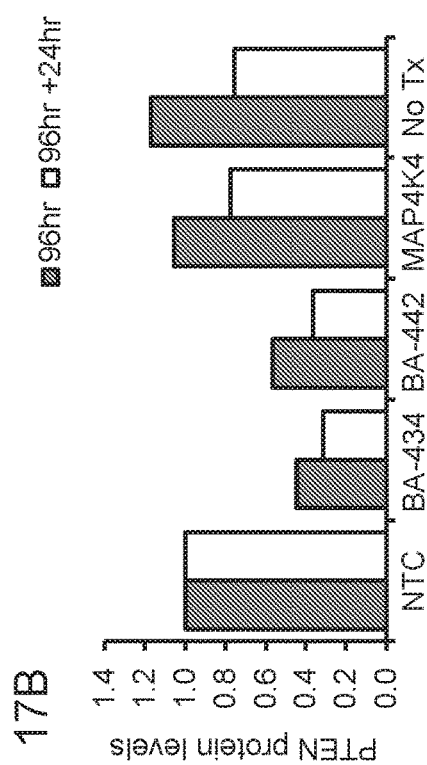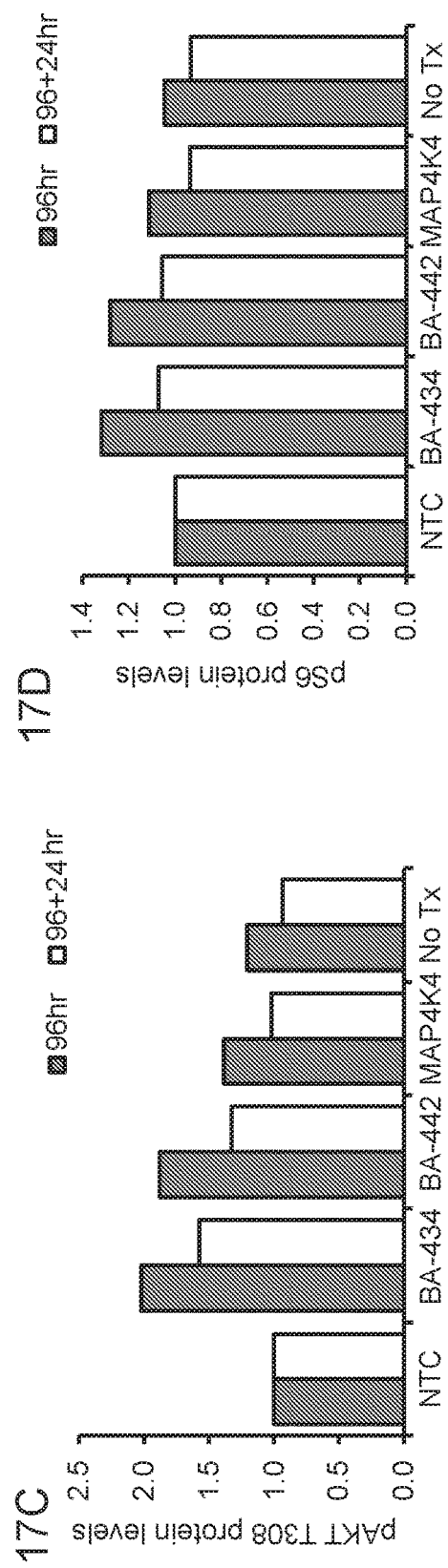
Figs. 17B-17D

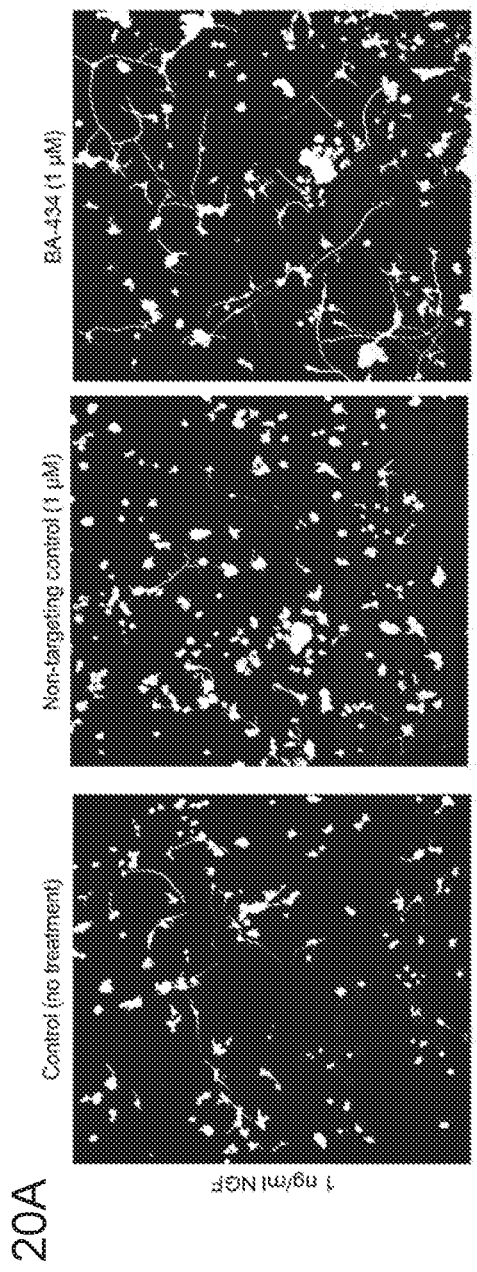
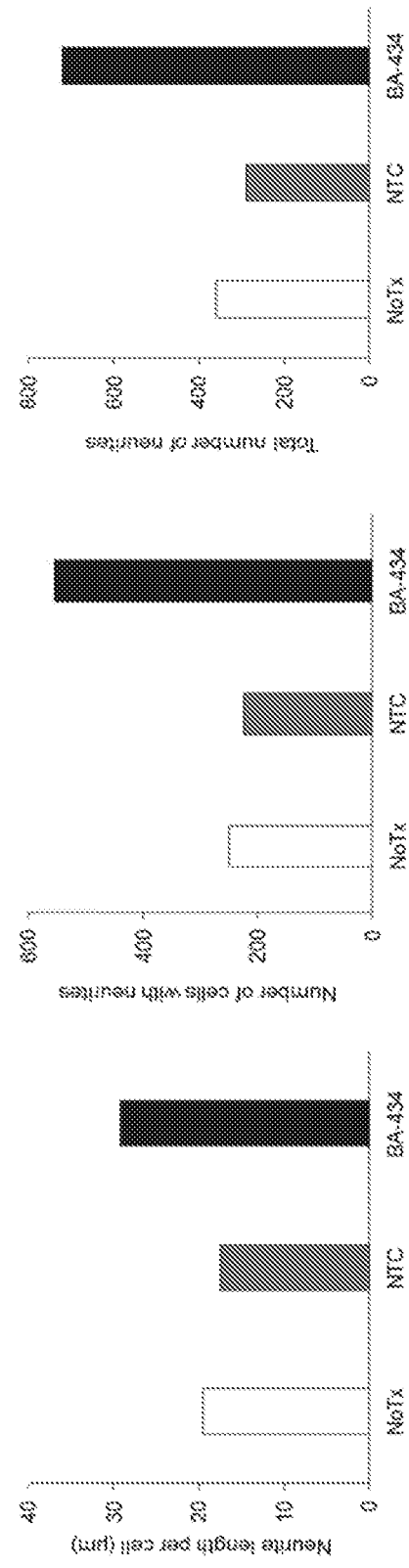
Figs. 20A-20D

Alignment of PT434 to human PTEN cDNA [NCBI Reference Sequence: NM_000314.6]
8718 nt
CDS   1032..2243
CLUSTAL W (1.83) multiple sequence alignment

```
huPTEN                                                      CCTCCCCTCGCCCGGCGCGGTCCCGGTCCGCCTCTCGGCCTCGGCCTCCCCTCGGTC   60
PT434 huPTEN                                                      TTCCGAGGCGCCCCGGGCTCCCGGCGCGGCGGCGGAGGGGCGGGCAGGCCGGCGGGT   120
PT434 huPTEN                                                      GATGTGGCGGGACTCTTTATGCGCTGCGGCAGGATACGCGCTCGGCGCTGGGACGCGACT   180
PT434 huPTEN                                                      GCGGCTCAGTTCTCTCCTCTCGGAAGCTGCAGCCATGATGGAAGTTTGAGAGTTGAGCCGC   240
PT434 huPTEN                                                      TGTGAGGCGAGGCCGGGCTCAGGCGAGGGAGATGAGAGACGGCCGCGGCCCGGA   300
PT434 huPTEN                                                      GCCCCTCTCAGCGCCTGTGAGCAGCCGCGGGGGCAGCGGCCCCTCGGGGAGCCGGCCT   360
PT434 huPTEN                                                      GCGGCGGCGGCAGCGGCGGCGGCGGCCGTTTCTCGCCTCTTCGTCTTTCTAACCGTGCAGCCT   420
PT434
```

Fig. 34

```
huPTEN    CTTCCTCTGGCTTCTCCTGAAAGGGAAGTGGAAGCCGTGGGCTTGGGCGGGAGCCGGCTG    480
PT434 huPTEN    AGGCGGGGGGGGGGGGGCATCCCGCCTCCTGAGCGGGAGGAGCGGCGGCAGAAGCGGCGG    540
PT434 huPTEN    CGGCGGCGGCGGCGGCGGCCTCCAGCTCCAAGGAAGGGGTCTGATCGAGTCCCTGTACTT    600
PT434 huPTEN    GGGCTGGAACGGGCACAGCCCGGAAGGGGTGGTCTCTCTCCCCTTCTACTGCCTCCAACA    660
PT434 huPTEN    CGGCGGCGGCACATCCAGGGACCCTGGGCCGGCGGCCGGTTTTAAACCTCCGCGCCGCAC    720
PT434 huPTEN    CCCCGTGGCCCGGGCTCCGAAGGCCAGCGGAGCGGAGCAGCCGTTCGGAAGGATTATTGT    780
PT434 huPTEN    CTTCTGCCCATTCCGCGCCCCCAGCTGCAGCCTCTGGCTGCTGAAGGCAAGCAAGCCC    840
PT434 huPTEN    AGTCCCTGCCAACCATCCAGAGGCGAGGCGGGCCAGCGCCATTACCGGTGCGTCCAGAGCC    900
PT434 huPTEN    AAGCGGCCGGCAGAGCGAGGCGGCCATCAGTTACCCAAGTCCAGAGCCCATTCCATCCTGC    960
PT434 huPTEN    AGAAGAAGCCCCGCCACCAGCAGCTTCTGCCATCTCTCCCTTTTCTCAGCCACA    1020
PT434
```

Fig. 34 (continued)

| | | |
|---|---|---|
| huPTEN PT434 | GGCTCCCAGAACATGACAGCCATCATCAAGAGAGATCGTTAGCAGAACAAAGGAGATATC | 1080 |
| huPTEN PT434 | AAGAAGAGATGGATTCGACTTAGATTGACCTATATTTATCCAAACATTATTGCTATGGAT | 1140 |
| huPTEN PT434 | TTCCTGCAGAAAGACTTGAAGGCGTATACGGACAATATTGATGATGTAGTAAGGTTTT | 1200 |
| huPTEN PT434 | TGGATTCAAAGCATAAAACCATTACAGGAGATATACAATCTTTGTGCTGAAAGACATTATG | 1260 |
| huPTEN PT434 | ACACCGCCTAAAATTTAATTGCAGAGTTGCACAATATCCTTTTGAAGACCATAACCCACCAC | 1320 |
| huPTEN PT434 | AGCTAGAACTTATCAAACCCTTTTGTGAAGATCTTGACCAATGGCTAAGTGAAGATGACA | 1380 |
| huPTEN PT434 | AATCATGTTGCAGCAATTCACTGTAAAGCTGGAAAGGGGAACGAACTGGTGTAATGATATGTG | 1440 |
| huPTEN PT434 | CATATATTATTACATCGGGGCAAATTTTTAAAGGCACAAGAGGCCCTAGATTTCTATGGGG | 1500 |
| huPTEN PT434 | AAGTAAGAACCAGAGACAAAAAGGGAGTAACTATTCCCAGTCAGAGGCGCTATGTGTATT | 1560 |
| huPTEN PT434 | ATTATAGCTACGTGTTAAAGAATCATCTGGATTATAGACCAGTGGCACTGTGTTCACA | 1620 |

Fig. 34 (continued)

```
huPTEN       AGATGATGTTTGAAACTATTCCAATGTTCAGTTGGCGGAACTTGCAATCCTCAGTTGTGG   1680
PT434 huPTEN       TCTGCCAGCTAAAGTGAAGATATATTCCTCCAATTCAGGACCCACACGACGGGAAGACA   1740
PT434 huPTEN       AGTTCATGTACTTTGAGTTCCCTCAGCCGTTACCTGTGTGTGATATCAAAGTAGAGT     1800
PT434 huPTEN       TCTTCCACAAACAGAACAGATGCTAAAAAGGAACAAAAATGTTTCACTTTTGGGTAAATA  1860
PT434 huPTEN       CATTCTTCATACCAGGACCAGAGGAAACCTCAGAAAAAGTAGAAGTCTATGTG         1920
PT434 huPTEN       ATCAAGAATCGATAAGCATTTGCAGTATAGAGCGTGCAGATAATGACAGAAATCTAG     1980
PT434 huPTEN       TACTTACTTTAACAAAAAATGATCTTGCACAAATAAAGCAAAATAAACAGTAGAGGAATATAGAGA   2040
PT434 huPTEN       TTTTCTCCAAATTTTAAGGTGAAGCTGTACTTCACAAAACAGTAGAGGAGCCGTCAAATC 2100
PT434 huPTEN       CAGAGGCTAGCAGTTCAACTTCTGTAACACCAGATGTTAGTGACAATGAACCTGATCATT 2160
PT434 huPTEN       ATAAATATTCTGACACCACTGACTCTGATCCAGAGAATGAACCTTTTGATGAAGATCAGC 2220
PT434
```

Fig. 34 (continued)

```
huPTEN    ATAACTAAATTACAAAAGTCTGAATTTTTTTTATCAAGAGGGATAAAACACCATGAAAA    2280
PT434 huPTEN    TAAACTTGAATAAACTGAAAATGAACAATTCTCTTTTTTTTTAATGGCAATAGGACATTGTGTC    2340
PT434 huPTEN    AAGATTACCAGTTATAGGAACAATTCTCTTTCCTGACCAATCTTGTTTTACCCTATACAT    2400
PT434 huPTEN    CCACACAGGTTTTGACACTGTGTCAAGTTGAACATTTAAAATTCAATTAAGATTAATAAGATGTAT
PT434 huPTEN    ATACCTTTTTTGTGTCAAAAGGAACATTTAAAAAGTGAAAAAGTGTGTAGCGTGTCATGTAT
PT434 huPTEN    TCCCGTTTTATTCCAGTTTTTATAAAAGTGAGACAGACTGAGTGTGTATACCTGTAGGAATT
PT434 huPTEN    TTTTCCTTTGTGTTCTGTCAACCAACTGAAGTGGCTAAGAGCTTTGTGATATACTGGTT
PT434 huPTEN    CATATCCTACCCTTGCACTTGTGGCAACAGATAAGTTTGCAGTTGGCTAAGAGAGTT
PT434 huPTEN    TCCGAAGGTTTTGCTACATTCTAATGCATGTATTCGGGTTAGGGAATGGAGAATGC
PT434 huPTEN    TCAGAAGGAAATAATTTTTATGCTCTCTGGACCTATAACCATCTCCAGCTATTTACA
PT434
```

```
huPTEN    ACCCTTTTGACCTTTACACATTCTATTACATGAATTTTGCAGTTTGCACATTTTTAAA
PT434     ------------------------------------------------------------ huPTEN    TGTCATTAACTGTTAGGAATTTTACTTGAATACTGAATACATATAATGTTATATTAAA
PT434     ------------------------------------------------------------ huPTEN    AAGGACATTTGTGTTTAAAAGGAAATTAGAGTTGCAGTAAACTTTTCAATGCTGCACACAA
PT434     ------------------------------------------------------------ huPTEN    AAAAAAGACATTTGTGATTTTTTCAGTAGAGAATTGTCCTACATGTGCTTTATTGATTTGCTAT
PT434     ------------------------------------------------------------ huPTEN    TGAAAGAATAGGCAGGTTTTTTTTTTTTTTTTAAAGTGCAGTGTTGAAT
PT434     ------------------------------------------------------------ huPTEN    CATTTCTTCATAGTGCTCCCCCGAGTTGGGACTAGTGCTTCAATTCACTTCTTAAAAAA
PT434     ------------------------------------------------------------ huPTEN    AATCATCATATATTTGATATGCCCAGACTGCATAACGATTTAAGCGGAGTACAACTACTA
PT434     ------------------------------------------------------------ huPTEN    TTGTAAAGCTAATGTGAAGATATTATTAAAAAGGTTTTTTTTCCAGAATTTGGTGTCT
PT434     ------------------------------------------------------------ huPTEN    TCAAATTATACCTTCACTTGACATTGAATATCCAGCCATTTGTTCTTAATGGTATA
PT434     ------------------------------------------------------------ huPTEN    AAATTCCATTTTCAATAACTTATTGGTCTGAATTGTTCACTAGCTGTGGTCTGACCTA
PT434     ------------------------------------------------------------
```

Fig. 34 (continued)

```
huPIEN    GTTAATTTACAAATACAGAATTGAATAGGACCTACTAGAGCAGCATTTATAGAGTTTGATG
PT434     ------------------------------------------------------------ huPIEN    GCAAATAGAATTAGGCAGAACTTCATCTAAAATATTCTTAGTAAATAATGTTGACGACGTTT
PT434     ------------------------------------------------------------ huPIEN    TCCATAACCTTGTCAGTTTCATTCAACAATTTTTAAATTTTAACAAAGCTCTTAGGATTT
PT434     ------------------------------------------------------------ huPIEN    ACACATTTATATTTAAACATTGATATATAGAGTATTGATTGATTGCTCATAAGTTAAATT
PT434     ------------------------------------------------------------ huPIEN    GGTAAAGTTAGAGACAAACTATTCTAACACCCTCACCATTGAAATTTATATGCCACCTTGTC
PT434     ------------------------------------------------------------ huPIEN    TTTCATAAAAGCTGAAAAATTGTACCTAAAATGAAAATCAACTTCATGTTTTGAAGATAG
PT434     ------------------------------------------------------------ huPIEN    TTATAAATATGTCTTGTTAATTCGGGCACCGCATAATAAAAGTAACTTTATTG
PT434     ------------------------------------------------------------ huPIEN    TTCCAATATGTAACATGGAAGGCCAGGTCATAAATAATGACATTATAATGGGCTTTTGCA
PT434     ------------------------------------------------------------ huPIEN    CTGTTATTATTTCCTTGGAATGCAAGGTCTGAATGAGGGTTTGATTTTGAATGTT
PT434     ------------------------------------------------------------ huPIEN    TCAATGTTTTTGAGAAGCCTTGCTTACATTTTATGGTGTAGTCATTGGAAAATGGAAAAAT
PT434     ------------------------------------------------------------
```

| | |
|---|---|
| huPTEN<br>PT434 | TTTAACTGTAGTATTTGGCAGAAGTTGCCTTCTACCTGCTGCAAGTTCAAAAGTCAACCTGTT |
| huPTEN<br>PT434 | TTCATATAGAATATATACTAAAAATTCAGTCTGTTAACAGCCTTACTCTGATTCA |
| huPTEN<br>PT434 | GCCCTCTTCAGATACTCTTGTGCTGTGCCAGTGCCTCTGTGTGTAAATGCTATGCACTG |
| huPTEN<br>PT434 | AGGATACACAAAAATACCAATATGATGTGTACAAGAATAATGCCTCATCCCAATCAGAATGT |
| huPTEN<br>PT434 | CCATTTGTTATTGTTTGTTAACAACCCTTTATCTCTTAGTGTTATAAACTCCACTTAA |
| huPTEN<br>PT434 | AACTGATTAAAGTCTCATTCTGTCATTGTGTGAGTGTTTATTAAATGAGAGTTTATAA |
| huPTEN<br>PT434 | TTCAAAATTGCTTAAGTCCATTGAGTTTTAATTAATGGCAGCCAAAATGTGAATACAAAG |
| huPTEN<br>PT434 | TTTTTCAGTTTTTTTTTTCCTGCTGTCCTTCAAAGCCTACTGTTTAAAAAAAAAAAAAAA |
| huPTEN<br>PT434 | AAAAAACATGGCCTGAGAGTAGAGTATCTGTCTACTCATGTTTAATTAAGGAAAAACACT |
| huPTEN<br>PT434 | TATTTTTAGGGCTTTAGTCATCACTTCATAAATTGTATAAGCACATTAAATAGCGTTCTA |

Fig. 34 (continued)

| | |
|---|---|
| huPTEN<br>PT434 | GTCCTTGAAAAGTCCAAGAATTCTTAGAAGAATTGTGCATATTTTATTATGACAATGTTT |
| huPTEN<br>PT434 | GAAGATAATTCCCCAGAATGGAATTGATATACTTAGATTCAATTTGTGGCTTTGTCTA |
| huPTEN<br>PT434 | TTATTCTGTACTCTGCCATCAGCATATGAAAGCTTCATTACTCATCATGACTTGTGCC |
| huPTEN<br>PT434 | ATATAAAAAATTGATATTTCGGAATAGTCTAAAGGACTAAAGCATATCCTTTCAACAAAGCATATGT |
| huPTEN<br>PT434 | TTGTTTCTAATATTCTTAAAAGCTTGAAGACTAGTTTGTACAAGTGTTAAAAAAAATAAAGTAGCAATGTTACA |
| huPTEN<br>PT434 | AAAGTAATAAGAAAGTGTAGTTTGTACAAGTTACATTTCTCCATGTAATTTTTTAAAAAGTAAAATGAA |
| huPTEN<br>PT434 | GTCGGGACTTTATTATTCAAGTTACATTTCTCCATGTAATTTTTTAAAAAGTAAAATGAA |
| huPTEN<br>PT434 | AAAAGTGCAATAATGTAAAAATATGAAGTGTATGTGTACACAATTTATTTCGGTAT |
| huPTEN<br>PT434 | CTTGGGTATACGTATGTTTGAAAACTATACTGGAGTCTAAAAGTATTCTAATTTATAAGA |
| huPTEN<br>PT434 | AGACATTTTGGTGATGTTTGAAAAATAGAAATGTGCTAGTTTGTTTTTATATCATGTCC |

Fig. 34 (continued)

```
huPTEN    TTTGTACGTGTAATATGAGCTGGCTTGGTTCAGTAAATGCCATCACCATTCCATTGAG
PT434 huPTEN    AATTTAAAACTCACCAGTGTTAATATGCAAGGCTTCCAAGGCTTATGAAAAATCAAG
PT434 huPTEN    ACCCTTAAATCTAGTTAATTGCTGCTAACATGAAACTCTTTGGTCTTTATTTTGCC
PT434 huPTEN    AGATATATTAGACACACATCTAAAGCTTAGTCTTAAATGCTTAAGTAGCTATTGATTA
PT434 huPTEN    GTGCTGTGTGCTAGTTCAGAAAGAAATGTTTGTGAATAACAAGAATATTCAGTCCAAA
PT434 huPTEN    CTGTTGTAAGGACTACCTGAAACCAGGAACAGGATAATGGAAAAGTCTTTTAAAG
PT434 huPTEN    ATGAAAATGTTGGAGCCAACTTCTTATAGAATTAATTGTATGTGGCTATAGAAAGCCTAA
PT434 huPTEN    TGAATTGTTGCTTATTTTTTGAGAAGCATATTATTCTTTTATGACCATAATCTTGCTGTTTT
PT434 huPTEN    CCATCTTCCAAAAGATCTTCCTTCTAAATATGTATATCAGAATGGGTAGCCAGTCAGAC
PT434 huPTEN    AAATTCATATTGGTTGGTAGCTTTAAAAGTTTGTAATGTGAAAGACAGGAAGGACAAAA
PT434
```

Fig. 34 (continued)

```
huPTEN  TAGTTTGCTTTGGGTAGTACTCTGTGTGTTAAGCTAAGTATTTGAGAGACTACTTCCCC
PT434 huPTEN  ATCACACAACAACAATAAAATAATCACTCTATCACCTGGAAGACATAGCCATCGTT
PT434 huPTEN  AATATGTTAGTGACTATACAATCATGTTTCTCTGTATATCCATGTATATTCTTAAAA
PT434 huPTEN  ATGAAATTTATACTGTACCTGATCTCAAAGCTTTTAGCTTAGTATATCTGTCATGATT
PT434 huPTEN  TGTAGGATGTTCCATTGCATCAGAAAACGGACAGTGATTGATTACTTTCTAATGCCACA
PT434 huPTEN  GATCAAGCTTAACATTGTTGACATTGAATGTTTCTCTCAAAAATCATCTAAACATTAGA
PT434 huPTEN  TCTAAATATTGTTGACATTAGGATGATACAATGTAAATTAAAGTTACATTGTTTAGCATA
PT434 huPTEN  GACAAGCTTAACATTGTTAGAATGTTTCTCTTCAAAAATCATCTAAACATTAAGA
PT434 huPTEN  ATTGTGTTAAATAAGAATGTGTGAAACACTGTATTAGTAAACTTCATCACCTTTCTACTTC
PT434 huPTEN  CTTATAGTTTTTCAGTTTTGTAGTTCCCAAAACAGTTGCTCAATTTAAGCAAA
PT434
```

Fig. 34 (continued)

```
huPTEN    TTAATTTAACACCTGCCAAAAAAGCTGCTGTGGCTTATCAGTGTGTCTTAAATTCAA
PT434     ------------------------------------------------------------ huPTEN    ATGCTCATGTGAACTTTATCACATCAAAAATATTTCATTAATGATTCACCTTTAGCTCT
PT434     ------------------------------------------------------------ huPTEN    GAAAATTACCGCGTTTAGTAATTATAGTGGGCTTATAAAAACATGCAACTCTTTTTGATA
PT434     ------------------------------------------------------------ huPTEN    GTTATTTGAGAATATTTTGGTGAAAAATATTTAGCTGAGGGCAGTATAGAACTTATAACCA
PT434     ------------------------------------------------------------ huPTEN    ATATATTGAGTATATTTTAAAACATTTTACATATAAGTAAACTGCCATCTTTGAGCATAAC
PT434     ------------------------------------------------------------ huPTEN    TACATTTAAAAATAAAGCTGCATATTTTTAAATCAAGTGTTTAACAAGAATTTATATTTT
PT434     ------------------------------------------------------------ huPTEN    TTATTTTTAAAATTAAAATAATTATATTTATTTGTGTGCATATTTCCCTCTGTTGCATGAGGATTCTCATCTGT
PT434     ------------------------------------------------------------ huPTEN    GCTTATAATGGTTAGAGATTTAATTACTGCAGTGAATGAGGCTTGTAGTCTTC
PT434     ------------------------------------------------------------ huPTEN    TAGTGTTTCAGTTTGCCAAGTCTGTGTTTACTGCAGTGAAAATTCATCAAATGTTTCAGTGTG
PT434     ------------------------------------------------------------ huPTEN    GTTTTCTGTAGCCTATCATTACTGGCTATTTTTATGTACACCTTTAAGGATTTTCTGC
PT434     ------------------------------------------------------------
```

Fig. 34 (continued)

```
huPTEN     CTACTCTATCCAGTTGTCCAAATGATATCCTACATTTTACAAATGCCCTTTCAGTTTCTA
PT434 huPTEN     TTTCTTTTTCCATTAAATTGCCCTTCATGTCCTTAATGTGCAGTTTGTTAAGTGTGTGTG
PT434 huPTEN     TGTGTCTGTGTGTGTGTGTGAATTTCAAGAGTGCTAGACTTCCAATTTGAGAGAATT
PT434 huPTEN     AAATAATTTAATTCAGGCCAAACATTTTCATTGGAATTTCACAGTTCATTGTAATGAAAA
PT434 huPTEN     TGTTAATCCTGATGACCTTTGACATACAGTAATGAATCTTGAATATAATGAATTTGTT
PT434 huPTEN     AGTAGCATCTTGATGTGTGTTTTAATGAGTTATTTCAAGTGTGTGCATTAACCAAAGT
PT434 huPTEN     TGGCCATACTGGAAGTGTTTTATATCAAGTTCCATTTGGCTACTGATGGCAAAAATAGAA
PT434 huPTEN     ATGCCTTCCTATGGAGAGTATTTTTCCTTTAAAAAATTAAAAGTTAATTATTTTGACT
PT434 huPTEN     AAAAAAAAAAAAAAAA
PT434
```

Fig. 34 (continued)

Rattus norvegicus phosphatase and tensin homolog (Pten), mRNA
Sequence ID: ref|NM_031606.1|Length:1212Number of Matches:1

See 1 more title(s)

Related Information
Gene-associated gene details
UniGene-clustered expressed sequence tags
GEO profiles-microarray expression data
Map Viewer-aligned genomic context
Range 1: 1 to 1212GenBankGraphics Next Match Previous Match First Match
Alignment statistics for match #1

| Score | Expect | Identities | Gaps | Strand | Frame |
|---|---|---|---|---|---|
| 1940 bits(1050) | 0.0() | 1158/1212(96%) | 0/1212(0%) | Plus/Plus | |

Features:

```
Query  1032  ATGACAGCCATCATCAAGAGAGATCGTTAGCAGAAGCAAACAAAAGGAGAGATATCAAGAGGATGGA  1091
             ||||||||||||||||||||||||||||||||||||||||||||||||||||||||||||
Sbjct  1     ATGACAGCCATCATCAAGAGAGATCGTTAGCAGAAGCAAACAAAAGGAGAGATATCAAGAGGATGGA  60

Query  1092  TTCGACTTAGACTTGACCTATATTTATCCAAACATTATTGCTATGGGAGATTCCTGCAGAA  1151
             ||||||||||||||||||||||||||||||||||||||||||||||||||||||||||||
Sbjct  61    TTCGACTTAGACTTGACCTATATTTATCCAAACATTATTGCTATGGGAGATTCCTGCAGAA  120

Query  1152  AGACTTGAAGGCGTATACAGGAACATTATTGATGATGTAGTAAGGTTTTTGGATTCAAAG  1211
             ||||||||||||||||||||||||||||||||||||||||||||||||||||||||||||
Sbjct  121   AGACTTGAAGGTGTATACAGGAACATTATTGATGATGTAGTAAGGTTTTTGGATTCAAAG  180

Query  1212  CATAAAAACCATTACAAGAGATATACAATCTATGTGCTGAAGAGACATTATGACACCGCCAAA  1271
             ||||||||||||||||||||||||||||||||||||||||||||||||||||||||||||
Sbjct  181   CATAAAAACCATTACAAGAGATATACAATCTATGTGCTGAAGAGACATTATGACACCGCCAAA  240
```

Fig. 35

```
Query  1272  TTTAATTGCAGAGTTGCACAATATCCTTTGAAGAGACCATAACCACCACAGTAGAACTT  1331
             ||||| |||||||||||||||||||||||||||||||||||||||||||||||||||||
Sbjct  241   TTTAACTGCAGAGTTGCACAGTATCCTTTGAAGAGACCATAACCACCACAGTAGAACTT  300

Query  1332  ATCAAACCCTTTGTGAAGATCTTGACCAATGGCTAAGTGAAGATGACAATCATGTTGCA  1391
             ||||| |||||||||||||||||||||||||||||||||||||||||||||||||||||
Sbjct  301   ATCAAACCCTTTGTGAAGATCTTGACCAATGGCTAAGTGAAGATGACAATCATGTTGCA  360

Query  1392  GCAATTCACTGTAAAGCTGGAAAGGGACGAACTGGTGTGTAATGATATGTGCATATTATTA  1451
             ||||||||||||| ||||||||| |||||||||||||||||||||||||||||||||||
Sbjct  361   GCAATTCACTGTAAAGCTGGAAAGCTGGAAAGGGACTGGTGTGTAATGATATGTGCATATTATTG  420

Query  1452  CATCGGGGCAAATTTTTAAAGGGAGTAACTATTCCCAGTCAGGAGGCGCTATGTGTA  1511
             ||||||||||||||||||||||||||||||||||||||||||||||||||||||||
Sbjct  421   CATCGGGGCAAGTTTTTAAAGGGACTGGGATTTTTATGGGAAGTAAGGACC  480

Query  1512  AGAGACAAAAGGGAGTAACTATTCCCAGTCAGGAGGCGCTATGTGTA TATTATAGCTAC  1571
             |||||||||||||||||||||||||||||||||||||||||||||| |||||||||||
Sbjct  481   AGAGATAAAAGGGAGTAACTATTCCCAGTCAGGAGGCGCTATGTAT TATTATAGCTAC  540

Query  1572  CTGTTAAAAATCATCTGGATTATAGACCAGTGGCACTGTGTTCACAGATGATGTTT  1631
             |||||||| |||||||||||||||||||||||||||||||||||||||||||||||
Sbjct  541   CTGTTAAA ATCACCTGGATTACAGACAGTGGCACTGTGTTCACAGATGATGTTT  600

Query  1632  GAAACTATTCCAATGTTCAGTGGCCGGAACTTGCAATCCTCAGTTGTGTCTGCCAGCTA  1691
             ||||||||||||||||||||||||||||||||||||||||||||||||||||||||||
Sbjct  601   GAAACTATTCCAATGTTCAGTGGCCGGAACTTGCAATCCCAGTTTGTGTCTGCCAGCTA  660

Query  1692  AAGGTGAAGATATATTCCTCCAATTCAGGACCCACACGACGGGAAGACAAGTTCATGTAC  1751
             ||||||||||||||||||||||||||||||||||||||||||||||||||||||||||
Sbjct  661   AAGGTGAAGAGATCTACTCCTCCAACTCAGGACCCACACGACGGGAAGACAAGTTCATGTAC  720
```

Fig. 35 (continued)

```
Query  1752  TTTGAGTTCCCTCAGCCGTTACCTGTGTGTGTGTGATATCAAAGTAGAGTTCTTCCACAAA  1811
             ||||||||||||||||||||||||||||||||||||||||||||||||||||||||||||
Sbjct  721   TTTGAGTTCCCTCAGCCATTGCCTGTGTGTGTGTGGTGACATCAAAGTAGAGTTCTTCCACAAA  780

Query  1812  CAGGAACAAGATGCTAAAAAAGGACAAAAATGTTTCACTTTTGGGTAAATACATTCTTCATA  1871
             ||||||||||||||||||||||||||||||||||||||||||||||||||||||||||||
Sbjct  781   CAGGAACAAGATGCTAAAAAAGGACAAAAATGTTTCACTTTTGGGTAAATACGTTCTTCATA  840

Query  1872  CCAGGACCAGAGGAAACCTCAGAGAAAAAGTAGAAAAATGGAAGTCTATGTGATCAAGAAATC  1931
             ||||||||||||||||||||||||||||||||||||||||||||||||||||||||||||
Sbjct  841   CCAGGACCAGAGGAAACCTCAGAGAAAAAGTGGAAAAATGGAAGTCTTTGATCAGGAAATC  900

Query  1932  GATAGCATTTGCAGTATAGAGAGCGTGCAGATAATGACAAGGAATATCTAGTACTTTA  1991
             ||||||||||||||||||||||||||||||||||||||||||||||||||||   |
Sbjct  901   GATAGCATTTGTAGTATAGAGAGCGTGCCGGATAATGACAAGGAGTATCTTGCTCACCCTG  960

Query  1992  ACAAAAAATGATCTTGACTTGAAGCTGTACTTCACACCAGAGTTAGTGACAATGAACCAACCGATACTTTTCTCCAAT  2051
             ||||||||||||||||||||||||||||||||||||||||||||||||||||||||
Sbjct  961   ACAAAAAATGATCTTGACTTGAAGCTGTACTTCACAAAAACAGTAGAGACAAGGCCAACCGATACTTCTCTCCAAT  1020

Query  2053  TTTAAGGTGAAGTTAACTTCTGACTCTGATCCAGAGAATGAACCTTTGATGAAGATCAGCCGTCAAATCAAAGGCTAGC  2111
             ||||||||||||||||||||||||||||||||||||||||||||||||||||||||
Sbjct  1021  TTTAAGGTGAAGTTATACTTCACAAAAACAGTAGAGGAGCAAATGAACCTTTGATGAAGATCAGCCATCAAATCAGAGGCTAGC  1080

Query  2112  AGTTCAACTTCTGTGACTCCAGAGATCCAGAGAATGAACCTGATCATTATAGATATTCT  2171
             ||||||||||||||||||||||||||||||||||||||||||||||||||||||||
Sbjct  1081  AGTTCAACTTCTCCAGACGTTAGTGACGTTAGTGACAATGAACCTGATCATTATAGATATTCT  1140

Query  2172  GACACCACTGACTCTGATCCAGAGAATGAACCTTTTGATGAAGATCAGCATACACAATT  2231
             ||||||||||||||||||||||||||||||||||||||||||||||||||||||||
Sbjct  1141  GACACCACTGACTCTGATCCAGAGAATGAACCTTTTGATGAAGATCAGCATTCACAATT  1200

Query  2232  ACAAAAGTCTGA  2243
             ||||||||||||
Sbjct  1201  ACAAAAGTCTGA  1212
```

Fig. 35 (continued)

BA-434 sense (passenger) strand (SEQ ID NO: 5):
5'-UAGCUACCUGUUUAAA-3'

BA-434 antisense (guide) strand (SEQ ID NO: 6):
5'-UUUAAACAGGUAGCUAUAAUA-3'

Fig. 36

BA-434 sense (passenger) strand (SEQ ID NO: 7):
5'-mU.mA.G.mC.mU.A.mC.mU.G.mU.mC.mU.G.mU.mA#mA#mA*-3'

BA-434 antisense (guide) strand (SEQ ID NO: 8):
5'-PmU.fU.fU.A.fC.A.G.mG.fU.A.G.mG.fC.fU.fU#A#fU#A#fU#A-3'

Fig. 37

TREATMENT OF CNS INJURY WITH RNAI THERAPEUTICS

CROSS-REFERENCE TO RELATED APPLICATIONS

This application claims the benefit of and priority to Provisional Application No. 62/367,199, filed Jul. 27, 2016, the contents of which is incorporated by reference in its entirety.

SEQUENCE LISTING

The instant application contains a Sequence Listing which has been submitted electronically in ASCII format and is hereby incorporated by reference in its entirety. Said ASCII copy, created Feb. 2, 2021, is named 51245-011002_Sequence_Listing_02.02.21_ST25.txt and is 16,302 bytes in size.

FIELD OF THE INVENTION

The present disclosure relates to the fields of medicine and neurology, and more specifically, to compositions and treatments for promoting axon regeneration with specific RNA interference (RNAi) drugs.

BACKGROUND

In America, 12,000 people suffer SCI each year, most frequently from motor vehicle accidents or falls; in children SCI are mostly due to sports or water recreational activities. SCI often leads to a lifetime of disability and there are no approved drugs to improve functional outcome. Approximately 70% of patients suffer injuries to the cervical spinal cord which leads to quadriplegia and dependence on care for daily living.

The current treatment for SCI is decompression surgery and rehabilitation. Despite a plethora of targets and compounds that show recovery of function and walking in rodent models of SCI, very few have been taken forward to clinical studies. In the damaged CNS, there are insufficient growth factors to promote regeneration, and the CNS environment lacks positive substrate cues and is rich in growth inhibitory proteins (McKerracher et al. (1994) *Neuron.* 13:805-811; Mukhopadhyay et al. (1994) *Neuron.* 13:757-767; Walsh et al. (1997) *Ann. Rev. Cell Develo. Biol.* 13:425-456). It is also clear that there are intrinsic, cell-type specific signals that repress regeneration (Nawabi et al. (2012) *Genes Develop.* 26:1509-1514). There is a developmental switch in responsiveness to both intrinsic and extrinsic cues (Cai et al. (2001) *J. Neurosci.* 21:4731-4739; Goldberg et al. (2002) Science. (5574):1860-4; Park et al. (2010) *Expt. Neurol.* 223:45-50). PTEN has been identified as a target for regulating intrinsic signalling (Liu et al. (2010) *Nat. Neurosci.* 13:1075-1081; Park et al. (2008) *Science* 322(5903):963-6).

While neurons in the central nervous system (CNS) have the capacity to regenerate their axons after injury, they fail to do so, in part because regeneration is limited by intrinsic signaling pathways that are upregulated in mature neurons suppress axon regrowth; failure to regenerate is also due to growth inhibitory molecules that are present in the CNS environment, and receptors for growth inhibitory molecules activate neuron-intrinsic signaling pathways that prevent axon regrowth and regeneration. Thus, the search for targets to promote regeneration has focused on two general sets of candidates; extrinsic barriers to regeneration present in a damaged CNS environment (e.g., growth inhibitory molecules), and intrinsic signals that become upregulated and activated during neuronal differentiation and maturation e.g., PTEN, KLF4, KLF9, TSC1, SOCS3, and others. One barrier to progress in the field of spinal cord injury SCI has been the failure to translate experimental treatments to clinically relevant drugs after target identification.

The dual function protein known as PTEN (phosphatase and tensin homolog deleted on chromosome ten) plays a role in regulating cytoskeletal dynamics and cell motility (Meili et al. (2005) *Nat. Cell Biol.* 7:334-335) as well as in cell growth and survival (Stambolic et al. (1998) *Cell* 95:29-39) It is also an important target for regulating intrinsic signaling for axonal regeneration in the CNS (Park et al. (2008) *Science* 322 (5903):963-966). Utilizing its lipid phosphatase activity, it is able to downregulate the PI3 kinase AKT pathway, and leveraging its protein phosphatase activity, it can negatively regulate the MAP kinase pathway. By virtue of these activities, PTEN can significantly inhibit the activation of the Akt/protein kinase B pathway, a critical regulator of cellular proliferation, growth and migration in cycling cells. In neurons, Akt is implicated in the regulation of cell survival following neurotrauma, local axon assembly during axon growth and gene expression required for axon regeneration. In neurons, downstream effectors of PTEN are down-regulated during the development of long-tract axons (Liu et al., 2010) and the suppression of PTEN promotes axon regeneration. PTEN knockdown by silencing PTEN in corticospinal in motor neurons improves recovery of motor function after SCI. However, clinically relevant ways to transiently suppress PTEN without creating unwanted side effects have not been devised.

PTEN affects cytoskeletal dynamics, cell migration, growth and survival of non-neuronal cells of the CNS including astroglia and oligodendrocytes.

In astrocytes, PTEN inhibition results in astrocyte growth, proliferation and survival. Activation of the P13K/AKT pathway, which is negatively regulated by PTEN, promotes astrocyte migration (REF). PTEN knock-out promotes cell migration and wound healing in vivo. After mammalian spinal cord injury reactive astrocytes form a glial scar. Migration of reactive astrocyte into the lesion epicenter has a crucial role in CNS wound healing after trauma. Enhancing migration of astrocytes into the lesion site after rodent spinal cord contusion injury promotes seclusion of CNS infiltrating blood borne monocytes to enhance lesion contraction resulting in a reduced lesion area and to improve recovery of hindlimb function.

In oligodendrocytes PTEN inhibition promotes proliferation, differentiation, and axonal myelination. After CNS injury, oligodendrocytes frequently undergo cell death resulting in axonal demyelination and only insufficient axonal remyelination occurs. PTEN inhibitors promote oligodendrocyte survival and/or remyelination after SCI.

RNAi, induced by small interfering RNAs (siRNA), is used in a method for transiently blocking protein expression. RNA silencing is a sequence-specific regulation of gene expression triggered by double-stranded RNA (dsRNA) and is a mechanism that cells use to fight viruses. Different strategies have been developed to modify siRNA to allow stability in and delivery to cells and tissues. For example, stability of the dsRNA is achieved by modifying the nucleotides in various ways. Modifications that confer stability to RNAi are described in U.S. Pat. No. 9,080,171; U.S. Pub. No. 2012/0142763A1; and Rettig et al. (2012) *Mole. Thera.* 20:483-512). Nuclease stability, strand loading, off-target effects, immunogenicity, biodistribution, potency and half-life are all factors that must be considered in making target-specific siRNAs suitable for therapeutics.

Different methods have been used for local delivery of drugs to the CNS. However very few of the techniques tested in animals have proven robust for human use. For example, intrathecal delivery of antibodies to promote regeneration caused unacceptable infection rates in one clinical trial, and the protocol was changed to intermittent, intrathecal bolus injections, a procedure which is difficult and painful for patients. Therapeutic proteins in a clinical trial for SCI are provided in a kit which includes an approved fibrin sealant (e.g., Fehlings et al. (2011) *J. Neurotrauma* 28:787-796), and the technique is to mix the new drug with already approved kit components to facilitate safety and delivery (U.S. Pat. No. 7,141,428). However, reliance on components made by separate manufacturers does not ensure an approved supply of components, necessitating complex manufacturing of individual kit components for drug manufacture.

In vivo delivery of siRNA has been one challenging aspect of developing a therapeutic drug using siRNA technology. A comparison of intracellular delivery of synthetic dsRNA or plasmid DNA encoding short hairpin RNA (shRNA) indicates that synthetic RNA is more effective and that the knockdown in expression is immediate and short-lived (McAnuff et al. (2007) *J. Pharmaceut. Sci.* 96:2922-2930). Also, unlike DNA plasmids and viral vectors, direct-delivery of siRNA does not require a nuclear localization signal and it carries a negligible risk for genomic integration.

Delivery of RNAi to cells in vitro and in vivo has used various methods such as lipid delivery, viral delivery, and by modifying the charge and structure to allow "self-delivery" (see, e.g., U.S. Pat. No. 8,796,443, and U.S. Pub. Nos. 2012/0142763, 2009/0093425, and 2012/0101045A1). While different delivery methods have been developed, little is known about how modifications to enhance delivery affect mRNA localization and trafficking, which ultimately influence translation, function, and specificity.

In addition, delivery to the CNS has been challenging because siRNAs do not penetrate the blood brain barrier. For treatment of spinal cord injury (SCI), viruses that express shRNA against PTEN have been delivered to cell bodies in the brain to treat the injured projection axons in the spinal cord many centimeters away (Liu et al. (2010) *Nat. Neurosci.* 13:1075-1081). However, this is not a clinically suitable delivery because in humans the cell bodies of corticospinal neurons in the cortex can be meters from injured axons in the spinal cord. In addition, viral gene delivery of PTEN shRNA results in a permanent, irreversible knock down of PTEN expression, which bears significant safety liabilities over long term, as PTEN is an important tumor suppressor gene.

Thus, what is needed are more efficacious therapeutic compositions for treating CNS injury and better modes of delivering them.

SUMMARY OF THE INVENTION

It has been discovered that a particular PTEN siRNA used in conjunction with self-delivery technology is a potent effector of PTEN mRNA and PTEN protein expression in mammalian cells. This discovery has been exploited to develop the present disclosure, which, in part, is directed to a composition of matter, pharmaceutical compositions, and methods of treating SCI and other types of neurotrauma using self-deliverable siRNAs (sdRNAs) targeting PTEN mRNA.

In one aspect, the disclosure provides a phosphatase and tensin homolog (PTEN) targeting agent comprising an isolated sdRNA molecule.

In some embodiments, the isolated sdRNA molecule comprises a nucleotide sequence complementary to a PTEN gene, the isolated sdRNA molecule comprising a guide nucleotide strand, a passenger nucleotide strand, and a cholesterol (TEG) molecule attached at the 3' end of the passenger strand. The isolated sdRNA molecule has a double-stranded region 8-15 nucleotides long and a single-stranded region at the 3' end of the guide nucleotide strand and being 4-12 nucleotides long. At least 40% of the nucleotides of the sdRNA molecule comprise at least one modification, and the sdRNA molecule does not form a hairpin. In certain embodiments, the guide strand has a nucleotide sequence comprising SEQ ID NO:5 or SEQ ID NO:7. In some embodiments, the passenger stand has a nucleotide sequence comprising SEQ ID NO:6 or SEQ ID NO:8. In particular embodiments, the guide strand has a nucleotide sequence comprising SEQ ID NO:5 or SEQ ID NO:7, and the passenger stand has a nucleotide sequence comprising SEQ ID NO:6 or SEQ ID NO:8. In a certain embodiment, the sdRNA molecule is BA-434 and comprises a guide sequence comprising SEQ ID NO:6 and a passenger sequence comprising SEQ ID NO:8.

In another aspect, the disclosure provides a pharmaceutical composition comprising a PTEN sdRNA molecule as described above and a pharmaceutically acceptable carrier. In some embodiments, the PTEN sdRNA molecule is BA-434 and comprises a guide sequence comprising SEQ ID NO:6 and a passenger sequence comprising SEQ ID NO:8.

In yet another aspect, the disclosure provides a method of inhibiting PTEN expression in a mammalian cell, comprising contacting the cell with an amount of a PTEN sdRNA as described herein such that PTEN mRNA expression is inhibited.

In some embodiments, the sdRNA molecule is BA-434 and comprises a guide sequence comprising SEQ ID NO:6 and a passenger sequence comprising SEQ ID NO:8. In certain embodiments, the cell is located in the central nervous system. In particular embodiments, the cell is in the spinal cord or in the optic nerve. In certain embodiments, the mammalian cell is a neuronal cell, an astrocyte, or an oligodendrocyte.

In still another embodiment, the disclosure provides a method of treating a CNS injury, comprising contacting the injury with an amount of the PTEN sdRNA as described herein effective to promote axon regeneration and/or effective to promote astrocyte cell migration to, and proliferation at, the injury. In some embodiments, the sdRNA molecule is BA-434 and comprises a guide sequence comprising SEQ ID NO:6 and a passenger sequence comprising SEQ ID NO:8. In certain embodiments, the CNS injury is a spinal cord injury or an optic neuropathy. In some embodiments, plasticity of interneurons is promoted at the injury.

Also provided is a method for promoting the survival or regeneration of a mature CNS neuron, the neuron having an axonal injury, the method comprising contacting the injured neuron with a therapeutically effective amount of a PTEN sdRNA a described herein. In some embodiments, the sdRNA molecule is BA-434 and comprises a guide sequence comprising SEQ ID NO:6 and a passenger sequence comprising SEQ ID NO:8. In certain embodiments, the injured neuron is in the spinal cord or the optic nerve of a mammalian subject.

DESCRIPTION OF THE DRAWINGS

The foregoing features of embodiments will be more readily understood by reference to the following detailed description, taken with reference to the accompanying drawings, in which:

FIG. 3 is a graphic representation showing the results of PTEN sdRNA screening in HeLa cells using a luciferase assay. The different sequences tested are numbered, NTC is a non-targeting control, sdMAP4K4 is a positive control;

FIG. 16A is a representation of a Western blot showing expression of PTEN, phospo-S6 (pS6) and GAPDH from cortical neurons after they were exposed to sdRNAs for either 48 hours (lanes 1-4) or 72 hours (lanes 5-9). lane 1: non-targeting control sdRNA; lane 2: BA-434; lane 3: BA-441; lane 4: BA-442; lane 5: non-targeting control sdRNA; lane 6: BA-434; lane 7: BA-441; lane 8: BA-442; lane 9: untreated cells;

FIG. 17B is graphical representation showing the relative protein expression of PTEN normalized to total S6 protein in cultured rat cortical neurons after indicated treatment for either 96 hours or 96 hours followed by a medium change and cultured for an additional 24 hours;

FIG. 17C is graphical representation showing the relative protein expression of pAKT normalized to total S6 protein in cultured rat cortical neurons after indicated treatment for either 96 hours or 96 hours followed by a medium change and cultured for an additional 24 hours;

FIG. 17D is graphical representation showing the relative protein expression of pS6 normalized to total S6 protein in cultured rat cortical neurons after indicated treatment for either 96 hours or 96 hours followed by a medium change and cultured for an additional 24 hours

FIG. 20A is a series of representations of fluorescent micrographs of PC12 cells immunolabeled for beta-3 tubulin (Tuj-1) 4 days after sdRNA administration showing neurite outgrowth in PC12 cells 4 days after administration of non-targeting control sdRNA (NTC) and BA-434 sdRNA;

FIG. 20B is a graphic representation showing the quantification of neurite outgrowth in PC12 cells 4 days after sdRNA application, where BA-434 treatment increases mean neurite length in comparison to non-targeting control (NTC) and untreated cells;

FIG. 20C is a graphic representation showing the quantification of neurite outgrowth in PC12 cells 4 days after sdRNA application, where BA-434 treatment increases mean number of cells that grow neurites longer than 5 µm in comparison to non-targeting control (NTC) and untreated cells;

FIG. 20D is a graphic representation showing the quantification of neurite outgrowth in PC12 cells 4 days after sdRNA application, where BA-434 treatment increases the mean number of neurites per cell in comparison to non-targeting control (NTC) and untreated cells;

Figure 34:
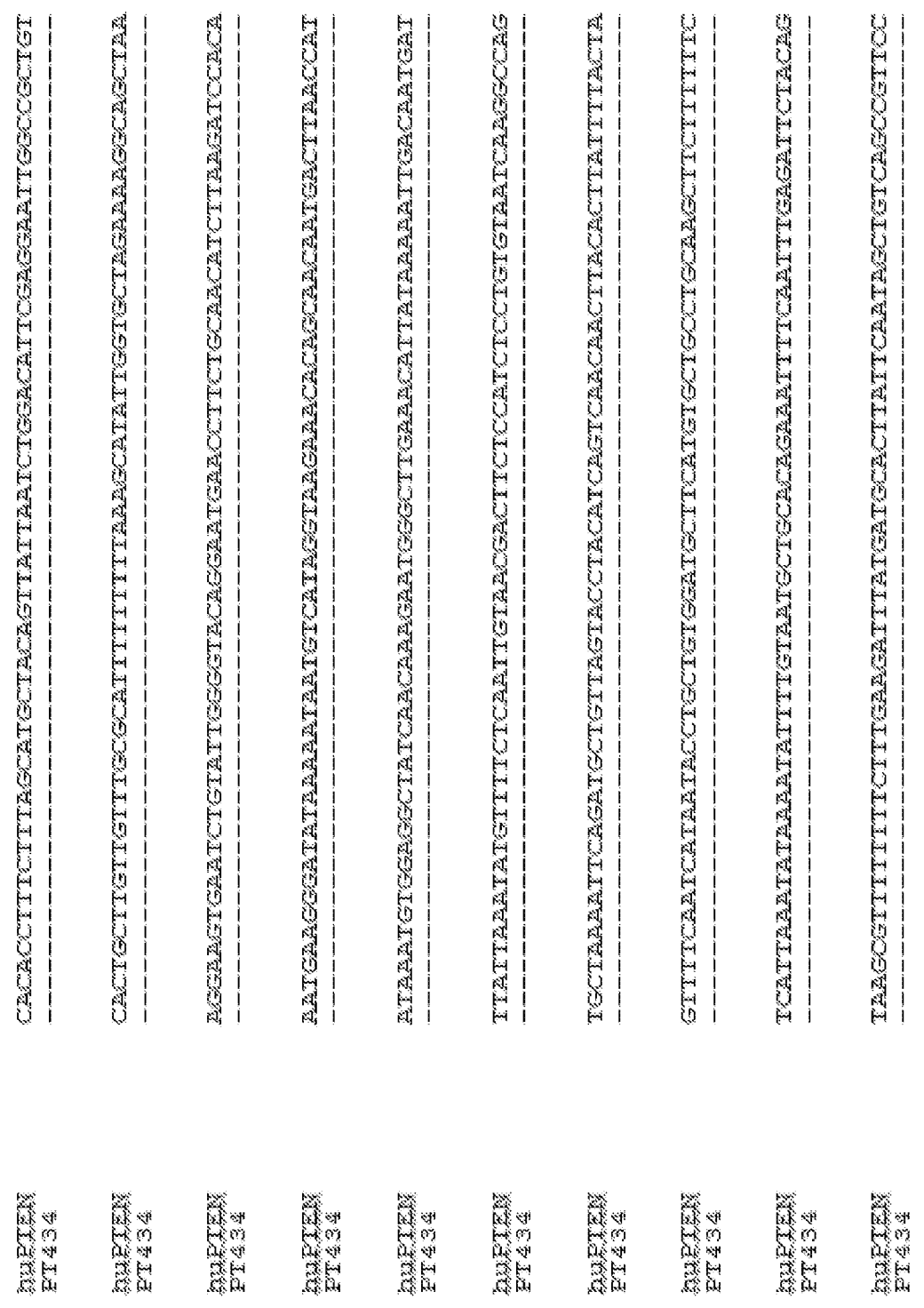

FIG. 34 is a schematic representation showing the alignment of BA-434 to the cDNA sequence for human PTEN (SEQ ID NO: 9) where the BA-434 sequence is shown contained in a black box;

FIG. 35 is a schematic representation showing a comparison of human cDNA (SEQ ID NO: 9) and rat cDNA (SEQ ID NO: 10) for PTEN with a perfect match, where the sequence of BA-434 is shown contained in a black box;

FIG. 36 is a schematic representation of nucleotide sequences of the BA-434 RNA sense strand (=passenger strand) (SEQ ID NO:5) and RNA antisense strand (=guide strand) (SEQ ID NO:6);

FIG. 37 is a schematic representation of the modified BA-434 RNA sense strand (PASSENGER) (SEQ ID NO:7) and the RNA antisense (GUIDE) strand, where the "m" indicates a 2'-O-methylated nucleotide, "f" indicates a 2'-fluorinated nucleotide, and "#" indicates a phosphorothioate linkage between the adjacent nucleotides; "P" indicates a phosphate group; "Cy3" indicates a cyanine 3 group; and asterisk "*" indicates tetraethylene glycol (TEG) cholesterol tagged to the 3' end of the sense strand.

DESCRIPTION

Figure 1:
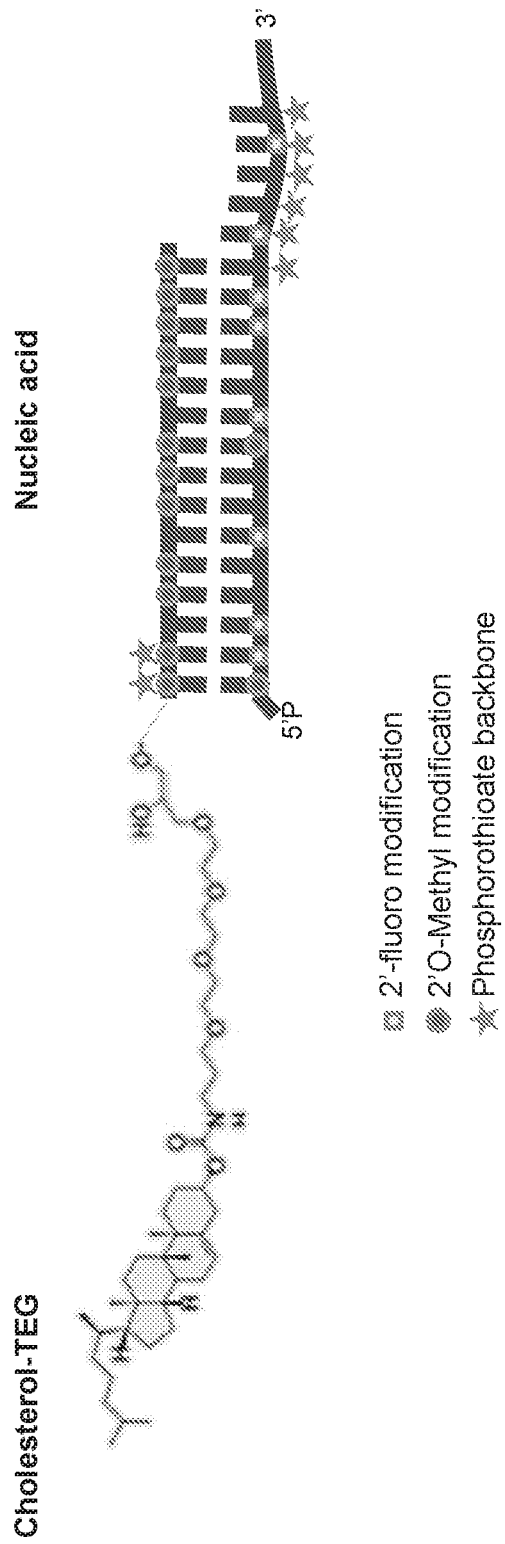
FIG. 1 is a diagrammatic representation diagram showing the structure of an sdRNA molecule.

Throughout this application, various patents, patent applications, and publications are referenced. The disclosures of these patents, patent applications, and publications are hereby incorporated by reference in their entirety into this application in order to more fully describe the state of the art as known to those skilled therein as of the date of the invention described and claimed herein. The instant disclosure will govern in the instance that there is any inconsistency between the patents, patent applications, and publications and this disclosure.

Unless otherwise specified, all technical and scientific terms used herein have the same meaning as commonly understood by one of ordinary skill in the art to which this disclosure pertains.

The present disclosure relates to nucleic acids or RNAi therapeutics which target PTEN mRNA within cells with improved in vivo delivery, and which promote axon regeneration in the CNS of an injured mammal. These novel RNAi therapeutics or sdRNAs easily penetrate neurons to silence PTEN and promote axon regeneration after injury such as traumatic brain injury, acute and chronic SCI, and optic neuropathies. This modulation of PTEN expression improves recovery after CNS injury by helping neurons create new adaptive circuitry to overcome deficits caused by loss of connections after injury. In addition, the sdRNAs according to the disclosure promote astrocyte and oligodendrocyte migration to, and proliferation at, the site of the CNS injury.

I. PTEN sdRNA

The RNAi therapeutic compositions of the present disclosure comprises a PTEN sdRNA. sdRNAs are double-stranded siRNA molecules that are modified to be cell-permeable and to possess increased stability against endo- and exonuclease degradation. Rather than the use of delivery vehicles, self-delivering RNA is effective in vivo by local administration sdRNA triggers degradation of mRNA, thereby decreasing expression of the targeted protein. The strategy of inhibiting PTEN mRNA expression by sdRNA technology differs from use of small molecule PTEN inhibitors described in U.S. Pat. No. 8,728,756. PTEN sdRNAs do not inhibit PTEN protein function; rather, they regulate expression levels of the protein. The use of sdRNA has the advantage of less off-target effect to other phosphatases because pharmacological inhibitors of phosphatases will have off-target effects by binding to related protein classes of other phosphatases.

Furthermore, sdRNAs targeting PTEN expression have a more long-lasting effect on PTEN phosphatase activity. The antisense or passenger strand of sdRNAs is released from the sense strand, which confers lipophilicity to the double-stranded sdRNA. The antisense strand, itself, is lipophobic and hence, remains intracellularly resulting in long lasting inhibition of PTEN protein expression due to increases stability against endonucleases. sdRNA administered to the site of SCI also distributes more locally in contrast to most small molecules, which usually distribute rapidly to other parts of the target organ and other tissues even after local administration. Consequently, off-target tissue exposure is a negligible safety concern for sdRNAs.

The present disclosure provides selected sdRNA molecules useful in the reduction of expression or knock down of PTEN mRNA and protein levels in CNS cells and tissues, such as neurons, astrocytes, and glial cells.

The sdRNA molecule comprises a nucleotide sequence complementary to a PTEN gene and comprises a guide (antisense) nucleotide strand, a passenger (sense) nucleotide strand. There is a cholesterol-TEG molecule attached to the 3' end of the passenger strand. The sdRNA molecule has a double-stranded region 8-15 nucleotides long and a single-stranded region at the 3' end of the guide nucleotide strand 4-12 nucleotides long. At least 40% of the nucleotides of the sdRNA molecule comprise at least one modification, and one nucleotide can have more than one different modification. These modifications include any chemical modifications to the nucleotides which provides stability without interfering with the targeting PTEN effector abilities of the sdRNA. Such modifications include but are not limited to, phosphorothioate, O-methyl, and 2-fluoro modifications. How to make these modifications and other useful modifications are described in e.g., U.S. Pat. No. 9,340,786

These sdRNA molecules do not form a hairpin.

A representative PTEN sdRNA (BA-434) is shown in FIG. 1. This molecule comprises a asymmetric combination of siRNA and antisense oligos, and includes lipophilic sterol and methyl modification which enable cell entry. The modification including fluoro, O-methyl, and phosphorothioate modifications, enable RNA half-life in biological solutions from 30 minutes to 20-24 hours. The guide strand of BA-434 has a nucleotide sequence comprising SEQ ID NO: 7, and the passenger strand has a nucleotide sequence comprising SEQ ID NO:8.(FIG. 37).

The PTEN sdRNA can be commercially obtained e.g. from Advirna LLC, Cambridge, Mass.; Trilink Biotechnologies, San Diego, Calif.).

Alternatively, the PTEN sdRNA can be synthesized according to known methods, (e.g., Byrne et al., (2013) *J. Ocul. Pharmacol. Ther.* 29(10):855-64.). In brief, RNAs are synthesized from Therapure™ ribo phosphoramidite monomers with a oligonucleotide synthesizer using phosphoramidite chemistry. Synthesized oligonucleotides are cleaved from the solid CPG supports and the protecting groups are removed by the treatment of 3:1 aqueous ammonia:ethanol.

Passenger strands are synthesized from CPG functionalized with cholesterol-triethyeneglycol-glycerol succinate. Crude oligonucleotides are precipitated with isopropanol, centrifuged and purified using ion exchange chromatography. The yield is analyzed by reverse-phase ion-pair chromatography, selected fractions are pooled and desalted by Tangential Flow Filtration and evaporated to dryness. Purity and molecular weight of filtered material is determined by HPLC analysis and ESI-MS analysis.

The correct sequence of PTEN to be effectively targeted by a sdRNA, a number of different PTEN-targeting siRNAs sequences were designed and tested for their ability to: (1) promote axon regeneration of CNS neurons; (2) be effectively delivered without the use of carriers; (3) not cause off-target effects; and (4) act on both rodent and human cells to facilitate clinical development. These PTEN sdRNAs are listed in FIG. 3.

As described above, the BA-434 sdRNA sequence (FIG. 36) (SEQ IS NOS; 5 and 6) including its nucleotide modification pattern (FIG. 37) (SEQ ID NOS: 7 and 8) shows efficacy in both cultured PC12 cells and rat primary neurons, which also supports its use for in vivo application. BA-434 sdRNA is not immediately effective in knocking down PTEN mRNA and protein levels, both in tissue culture and in vivo. This delay in RNA knockdown likely indicates that the sdRNA is trapped in the membrane and is only slowly released into the cytoplasm of the cell. Such a delay has utility in a slow release of the sdRNA and a lower dose needed for a sustained decrease in the target protein. The specificity of this delayed response is exhibited in cultured neurons (FIGS. 18 and 19) and CNS tissue (FIGS. 26 and 27), as described in the EXAMPLES below.

Figure 30A:
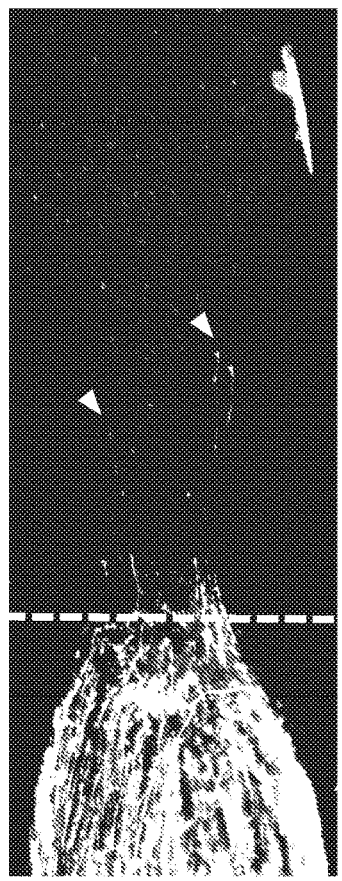
FIG. 30A is a representation of a micrograph showing RGC axon regeneration in the optic nerve 2 weeks after optic nerve crush and intravitreal injection of non-targeting control (NTC). Crush (injury) site is shown with the dotted line.
Figure 30B:
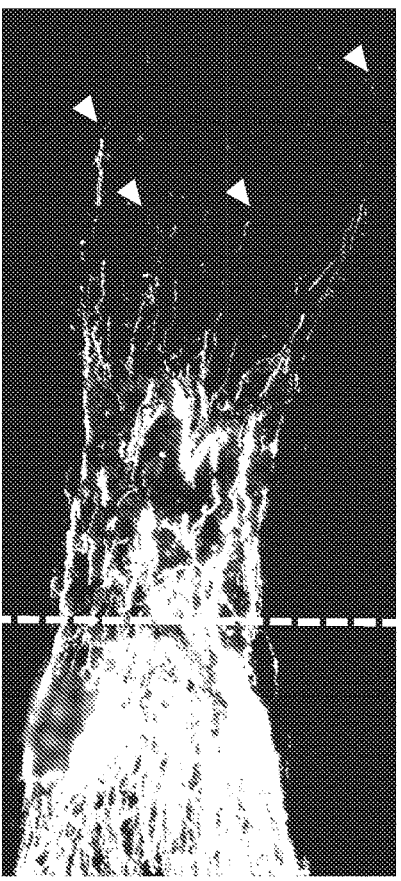
FIG. 30B is a representation of a micrograph showing RGC axon regeneration in the optic nerve 2 weeks after optic nerve crush and intravitreal injection of BA-434. Crush (injury) site is shown with the dotted line, regenerating axon shown with white arrow heads.
Figure 30C:
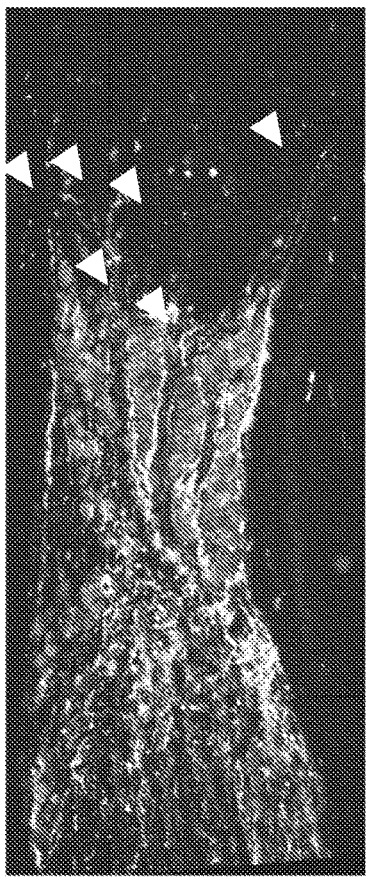
FIG. 30C is a representation of a micrograph showing immunofluorescence of the axon regeneration marker growth associated protein 43 (GAP43) in the same BA-434 treated animal as shown in FIG. 30B (demonstrating that axons are truly regenerating and are not axons that were spared by the initial crush). Where the crush (injury) site is shown with the dotted line, regenerating axon shown with white arrow heads.

The sustained change in protein levels over several days indicates the stability of the response of neurons to PTEN protein knockdown. This is important for axon regeneration. As described below in Example 620, a robust axon regeneration was demonstrated herein 2 weeks after optic nerve injury (FIGS. 30A-30C). This finding using local delivery of the sdRNA shows that this method is useful in a wide variety of types of neurotrauma.

The studies described in the present disclosure demonstrate that (1) BA-434 sdRNA is truly self-delivering; (2) BA-434 mRNA levels decrease rapidly after delivery (by 24 hours), whereas protein levels show a delay before decrease; (3) PTEN protein decreases significantly at 72 hours and longer after sdRNA delivery; and (4) knock-down of PTEN mRNA is sustained for at least 120 hours in primary neurons, while protein levels are reduced for at least 10 days (EXAMPLE 13, FIG. 19).

IV. Pharmaceutical Compositions

The PTEN sdRNAs of the present disclosure are useful in pharmaceutical compositions and methods for treating CNS neurotrauma. These pharmaceutical compositions include a therapeutically effective amount of a PTEN sdRNA. A "therapeutically effective amount" as used herein refers to that amount which provides a therapeutic and/or prophylactic therapeutic effect on the neurotrauma site. Such effects include, but are not limited to, axon regeneration, and glial cell proliferation at, and migration to, the site of the neurotrauma.

Such compositions can be prepared with a pharmaceutically acceptable carrier in accordance with known techniques, for example, those described in Remington. *The Science And Practice of Pharmacy* (9th Ed., 1995). The term "pharmaceutically acceptable carrier" is to be understood herein as referring to any substance that may, medically, be acceptably administered to a patient, together with a compound of this invention, and which does not undesirably affect the pharmacological activity thereof; a "pharmaceutically acceptable carrier" may thus be for example a pharmaceutically acceptable member(s) selected from the group comprising or consisting of diluents, preservatives, solubilizers, emulsifiers, adjuvant, tonicity modifying agents, buffers as well as any other physiologically acceptable vehicle. This pharmaceutical formulation may further contain additional Rho inhibitors.

The pharmaceutical compositions may be prepared in pharmaceutically acceptable dosage forms such as for oral, injectable, transdermal, epidural, and transmembrane use, and the like, or may be formulated for co-delivery in a delivery matrix, as described in U.S. Pat. Nos. 7,141,428 and 7,491,692.

Compositions suitable for oral administration may be presented in the form of a solution, the pharmaceutically acceptable carrier is one that does not inhibit the activity of the PTEN sdRNA, and can be, e.g., an aqueous liquid, such as buffered with a pharmaceutically acceptable pH buffer, or in non-aqueous liquid such as DMSO, or be prepared as an oil-in-water or water-in-oil emulsion.

Injectable dosage forms may be sterilized in a pharmaceutically acceptable fashion, for example, by steam sterilization of an aqueous solution sealed in a vial under an inert gas atmosphere at 120° C. for about 15 minutes to 20 minutes, or by sterile filtration of a solution through a 0.2 µM or smaller pore-size filter, optionally followed by a lyophilization step, or by irradiation of a composition containing a compound of the present invention by means of emissions from a radionuclide source.

The therapeutic compositions may be delivered in discrete units or dosage forms. If orally administered, these dosage forms may be capsules, cachets, lozenges, tablets, pills, powders, granules, chewing gum, suspensions, solutions, and the like. Each dosage form contains a predetermined amount of PTEN sdRNA.

A therapeutically effective dosage of the PTEN-targeting sdRNA therapeutic compound varies from patient to patient, and may depend upon factors such as the age of the patient, the patient's genetics, and the diagnosed condition of the patient, and the route of delivery of the dosage form to the patient. One useful therapeutically effective dose is the from about 10 µg to 950 µg of sdRNA. A therapeutically effective dose and frequency of administration of a dosage form may be determined in accordance with routine pharmacological procedures known to those skilled in the art. For example, dosage amounts and frequency of administration may vary or change as a function of time and severity of the spinal cord injury.

VI. Therapeutic Delivery Methods

Administration of the pharmaceutical compositions according to the disclosure can be local or systematic depending on the target tissue being treated. Alternatively, administration may be by injection into the cerebrospinal fluid as a solution or as a suspension suitable for sustained release from the injected pharmaceutical dosage form such as from a vesicle. For example, Administration may be made to the lesion site by neurosurgical application or by stereotactic injection.

In addition to regeneration of long-tract projections axons, with a focus on the corticospinal tract (CST), contralateral sprouting from uninjured axons and plasticity of the central pattern generators (CPGs) is also functionally important. Plasticity of interneurons in the spinal cord as used herein is the ability of the non-projection neurons to reform synaptic connections locally within the spinal cord which may be axon-dendrite connection, dendrite-dendrite connection, or dendrite-neuronal-cell body connections. Contralateral growth of CST fibers originating from uninjured axons may contribute to recovery of motor function after PTEN suppression following SCI. During CNS development there is an over-production of connections that are later pruned, and the CST also overproduces collateral branches prior to the refinement of circuits (Maier et al. (2006) *Philosoph. Trans. Roy. Soc. B: Biol. Sci.* 361(1473); 1611-1634). The major components of CPG networks are ventral interneurons that establish the rhythm and pattern of output of locomotor circuits. Delivering PTEN sdRNA inhibitors directly at the level of the injury is important in recovery after SCI, and stimulating plasticity of the ventral spinal cord is a good focus. Therefore, delivery of a compound that enhances sprouting and regeneration of axons is best delivered directly to the spinal cord, rather than targeting diverse nuclei of long tract neurons in brain and brainstem. For this reason, a local delivery approach is used here.

Figure 33:
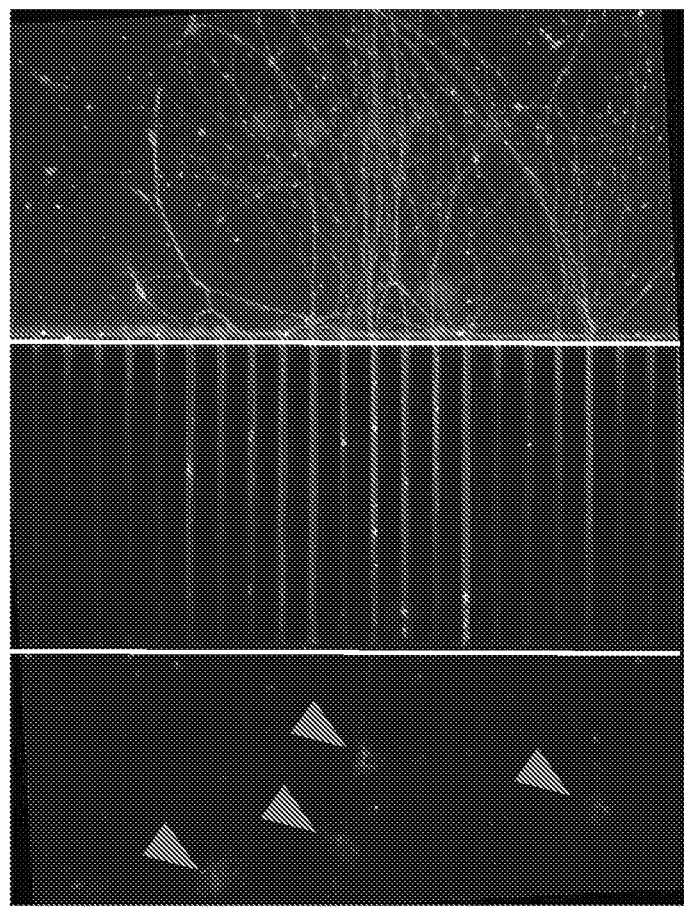
FIG. 33 is a representation of a fluorogram showing retrograde axonal transport of Cy-3 labelled, fluorescent BA-434 sdRNA into the neuronal cell bodies of primary rat cortical neurons growing in a two-compartment microfluidic chamber.
Figures 38A, 38B, 38C:
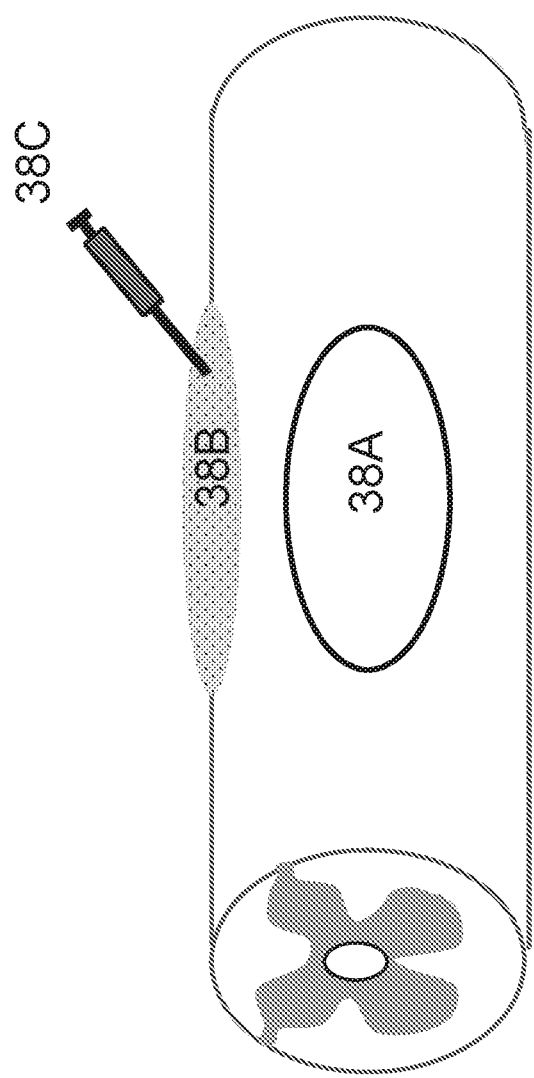
FIG. 38A-38C is a diagrammatic representation of the clinical delivery of an sdRNA to a patient with spinal cord injury, where the person with a spinal cord contusion injury (A) is treated by a surgeon who repairs the injury and applies a fibrin sealant or collagen gel device (B), after which the sdRNA is injected into the fibrin or collagen gel (C).

Local delivery of sdRNA targeted to PTEN enhances regeneration of long-tract neurons via retrograde transport of the sdRNA to the cell body where it decreases expression of PTEN. sdRNA can be retrogradely transported (FIG. 33).

Fibrin sealants, when delivered to the injured spinal cord, are used to seal dural tears after spinal surgery. When delivered with a pre-filled syringe, the sealant forms a clot on the spinal cord that dissolves over several weeks. An alternative method of delivering a sdRNA molecule as described herein is the injection of the concentrated sdRNA solution directly into the clot. This delivery ensures that the sdRNA is not lost with surgical fluids and blood during the surgery, but will be released slowly over time. Delivery of sdRNA directly in the clot is useful because of their potency, and small volumes are required. For example, about 50 µg to about 500 of sdRNA is required for direct delivery to the spinal cord in a volume of about 1 µl to about 50 µl. The volume is injected into a 2 mL clot which is the volume typically used by surgeons when they decompress the spinal cord by surgical intervention.

Chitosan hydrogels are suitable delivery systems for siRNAs. Chitosan hydrogel applied to the injured spinal cord in vivo are a permissive scaffold for axon regeneration after experimental SCI (Gnavi et al. (2013) *Int. Rev. Neurobiol.* 109:1-62). Therefore, delivery of chitosan gels containing PTEN sdRNA to a spinal cord lesion site in patients, either epidurally or by injection into the lesion cavity, is a useful method to enhance the axon regeneration, and at the same time provides a scaffold to support axon growth through the lesion site. sdRNA diluted in chitosan hydrogel can be delivered to the spinal cord injury site in liquid form an polymerizes into a gel at 37° C. siRNA in chitosan gels shows sloe release in vivo for at least 2 weeks (Ma et al. (2014) *J. Nanotechnol.* 12:23). Together with the prolonged activity of sdRNA, in vivo sdRNAs delivery by chitosan gels can provide exposure for at least one month after application to the injury site.

The following examples provide specific exemplary methods of the invention, and are not to be construed as limiting the invention to their content.

EXAMPLES

Example 1

Assay for Identification of Self-Deliverable PTEN sdRNA Compounds

The PTEN targeting agents described herein were designed and sent for synthesis as separate modified sense ("s") and antisense ("as") RNA strands. These strands were then annealed to form the sdRNA prior to testing (FIG. 36).

Figure 2:
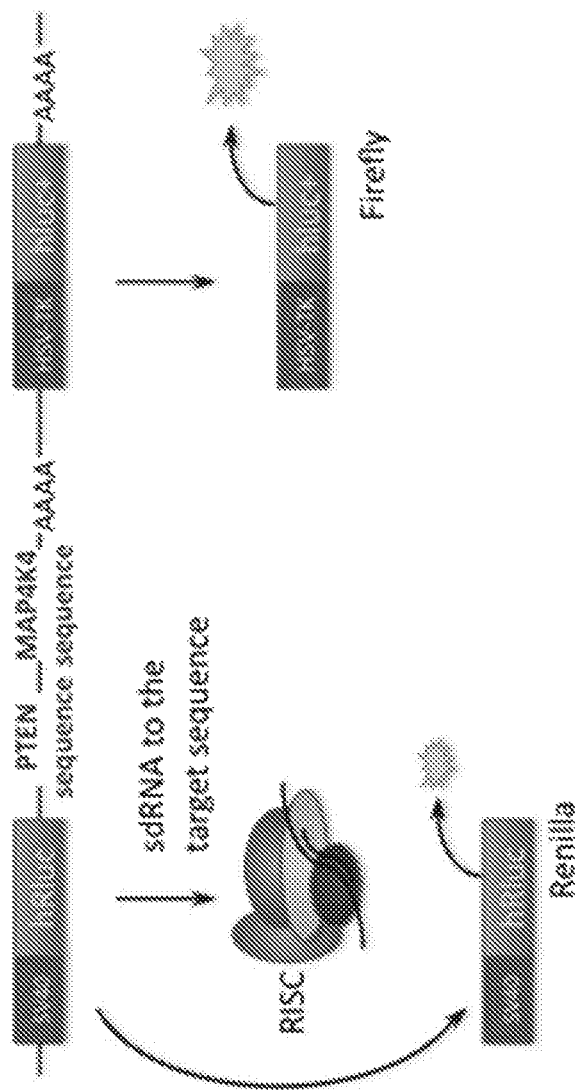
FIG. 2 is a diagrammatic representation of the luciferase reporter gene cloned for PTEN sdRNA screening.

The PTEN targeting agents were identified by treating HeLa cells carrying rat PTEN sequence with designed sdRNA compounds. For that, a luciferase reporter plasmid (FIG. 2) was constructed. *Renilla* luciferase sequence was followed by PTEN sequence and previously validated MAP4K4 sdRNA targeting sequences, as a positive control. Firefly luciferase sequence under separate promoter was used for relative luminescence signal normalization.

HeLa cells were transfected with the PTEN plasmid using Fugene HD (Promega, Madison, Wis.) according to the manufacturer instructions. Briefly, cells were seeded at $2.5 \times 10^6$ cells/10 cm$^2$ dish in the EMEM (ATCC, Manassas, Va.) medium without antibiotics. Cells were transfected 6 hr later with the plasmid at the 2.5:1 FuGENE:DNA ratio. Cells were left in the tissue culture incubator for 16 hr to 18 hr.

For sdRNA transfection, 2 µM solutions of each PTEN lead candidate, MAP4K4 (positive control) and NTC (non-targeting control) sdRNAs were prepared in serum-free EMEM medium at 50 µl/well of 96-well plate.

Luciferase-PTEN expressing HeLa cells were collected by trypsinization in a 50 ml tube, washed twice with medium containing 10% FBS without antibiotics, centrifuged at 200×g for 5 min at room temperature (RT) and resuspended in EMEM medium containing 6% FBS and without antibiotics. The cells were dispensed at 50 µl/well into the plate with pre-diluted oligos and placed in the incubator for 48 hrs.

For luciferase assay, cell lysates were prepared in Glo lysis buffer (Promega) at 50 µl/well, incubated 30 min at RT and split into 2 white 96-well plates. Cell lysates were mixed with *Renilla* and Firefly assay buffers separately. Luminescence was detected in SpectraMax i3 (Molecular Devices, Sunnyvale, Calif.). The *Renilla* signal was normalized for the firefly signal and expressed as a percentage of non-targeting control sdRNA (NTC) transfected cells.

FIG. 3 shows, that six compounds (BA-431, BA-434, BA-437, BA-441, BA-442, BA-445) reduced *Renilla* luciferase expression by 80% or more.

Example 2

Delivery of sdRNA Into Rat Pheochromaocytoma PC-12 Cells

PC-12 cells (ATCC) were cultured on collagen I coated vessels in the presence of 100 ng/ml Nerve Growth Factor (NGF) (Sigma-Aldrich, St. Louis, Mo.). For transfection, cells were collected by trypsinization and diluted with RPMI medium containing 1% FBS and 100 ng/ml NGF and seeded into 96-well plate at 10,000 cells/well.

MAP4K4 sdRNA conjugated with Cy3 fluorophore was added to the cells at 1 µM final concentration. Images were taken on EVOS FL Imaging System (Life Technologies, Carlsbad, Calif.) at various incubation times between 10 min and 24 hrs.

Figure 4A:
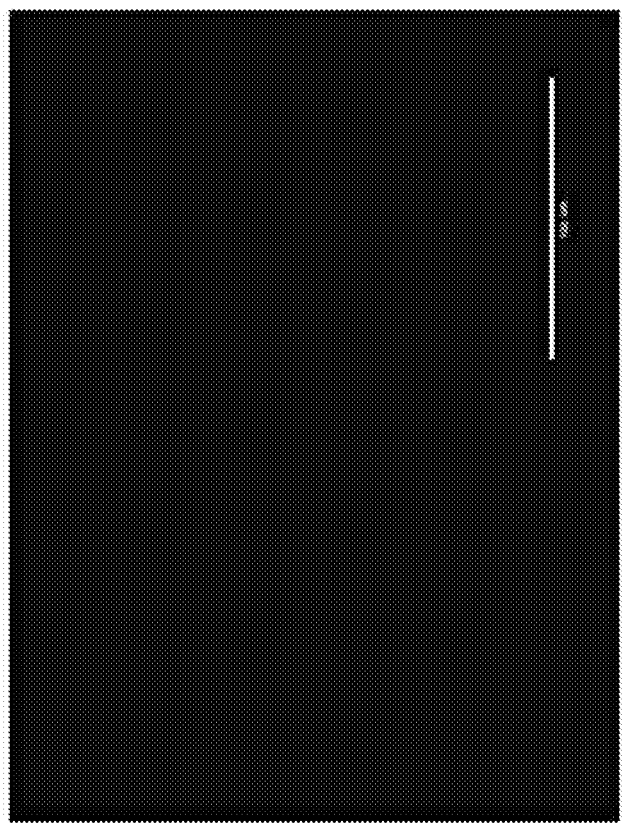
FIG. 4A is a representation of a fluorescent image of Cy3-labeled MAP4K4 sdRNA delivery into PC-12 cells.
Figure 4B:
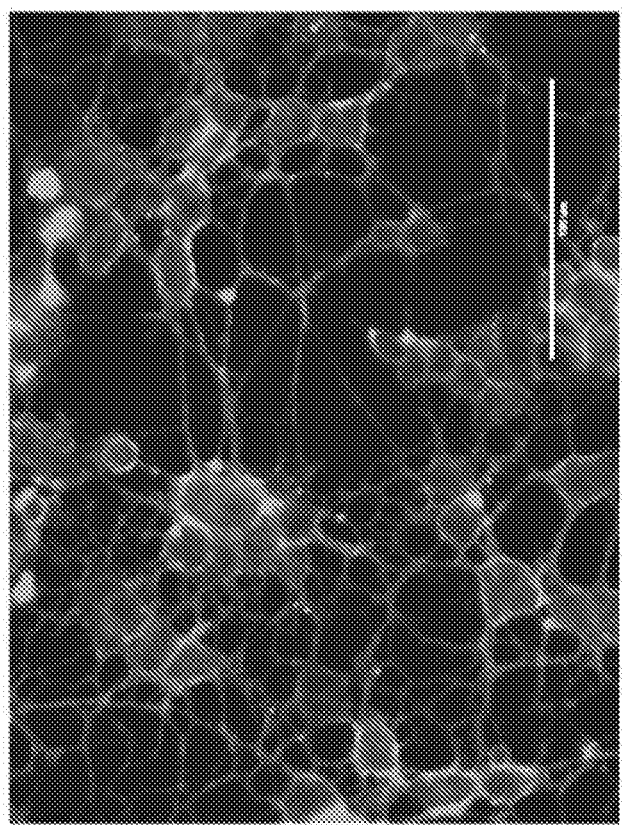
FIG. 4B is a representation of a fluorescent image of a non-transfected control that does not show any labeling.

FIG. 4 demonstrates that Cy3-fluorescence is clearly visible inside the cells, which proves passive, cellular uptake of MAP4K4 sdRNA.

Example 3

Validation of sdRNA Gene Silencing Efficacy in PC-12 Cells

PC-12 cells were cultured as described in EXAMPLE 1. The efficacy of MAP4K4 sdRNA was tested by qRT-PCR.

2× solutions of MAP4K4 and NTC (non-targeting control) sdRNAs were prepared in serum-free EMEM medium, by diluting 100 μM oligonucleotides to 0.08 μM-4 μM final concentration in the total volume of medium for each oligo concentration. Oligonucleotides were dispensed into a 96-well plate at 50 μl/well.

PC-12 cells were collected for transfection by trypsinization in a 50 ml tube, washed twice with medium containing 10% FBS without antibiotics, spun down at 200× g for 5 min at room temperature and resuspended in EMEM medium containing twice the required amount of FBS for the experiment (2%) and NGF (200 ng/ml). Cell concentration was adjusted to 120,000 cells/ml. Cells were dispensed into 50 μl/well into the 96-well plate with pre-diluted oligos and placed in the incubator for 48 hr.

Gene expression was analyzed by qRT-PCR as follows. RNA was isolated from transfected PC-12 cells using the PureLink™ Pro96 total RNA purification Kit (ThermoFisher Scientific, Waltham, Mass.), with Quanta qScript XLT One-Step RT-qPCR ToughMix, ROX (VWR, Radnor, Pa.). The isolated RNA was analyzed for gene expression using the Human MAP4K4-FAM (Taqman Hs0377405_m1) and Human GAPDH-VIC (Applied Biosystems, Foster City, Calif.) gene expression assays.

The incubated plate was spun down and washed once with 100 μl/well PBS and lysed with 150 μl/well buffer provided in the kit. RNA isolation was conducted according to the manufacturer's instructions. RNA was eluted with 100 μl RNase-free water, and used undiluted for one-step qRT-PCR.

Dilutions of non-transfected (NT) cells of 1:5 and 1:25 were prepared for the standard curve using RNase-free water. qRT-PCR was performed by dispensing 9 μl/well into a low profile PCR plate and adding 1 μl RNA/well from the earlier prepared RNA samples. After brief centrifugation, the samples were placed in the real-time cycler and amplified using the settings recommended by the manufacturer.

MAP4K4 gene expression was measured by qPCR, normalized to GAPDH and plotted as percent of expression in the presence of non-targeting sdRNA. The results were compared to the normalized according to the standard curve.

Figure 5:
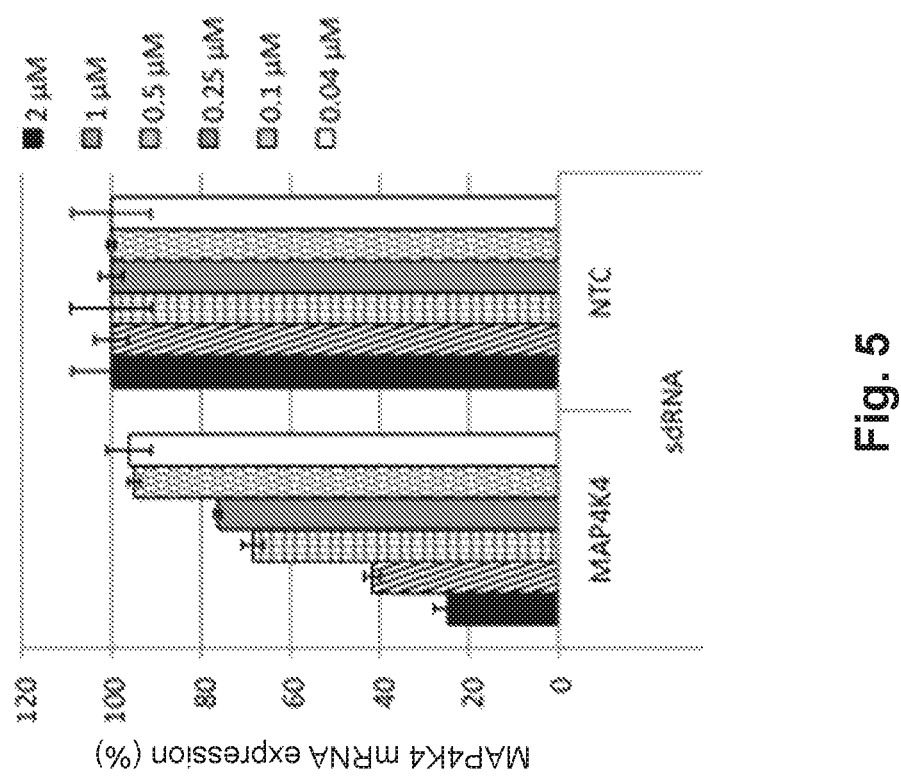
FIG. 5 is a graphic representation showing sdRNA-induced silencing of MAP4K4 by a MAP4K4 specific sequence (positive control) in contrast to a non-targeting control NTC (negative control). sdRNAs were tested in PC-12 cells in a dose-escalation experiment.

As shown in FIG. 5, MAP4K4 sdRNA compound induces a more than 70% reduction of MAPK4K mRNA in PC-12 cells, which demonstrates utility of sdRNA agents to suppress expression of target genes in cells normally very resistant to transfection, and suggests the that sdRNAs are efficacious to reduce target gene expression in vivo.

Example 4

Validation of PTEN Gene Silencing Efficacy in PC-12 Cells

Six out of 20 sdRNAs targeting PTEN with more than 70% knock-down efficacy in luciferase assay (FIG. 3), were validated for PTEN gene silencing efficacy in PC-12 cells. The sense and antisense for BA-434 are shown in FIG. 36.

Solutions of PTEN and NTC (non-targeting control) sdRNAs were prepared in serum-free EMEM medium. The final concentration range of oligonucleotides was 0.04 μM-2 μM. Treatment with sdRNA (48 hr) and qRT-PCR analysis were performed as described in EXAMPLE 3. PTEN expression was normalized to GAPDH and plotted as percent of expression of NTC sdRNA-treated cells.

Figure 6:
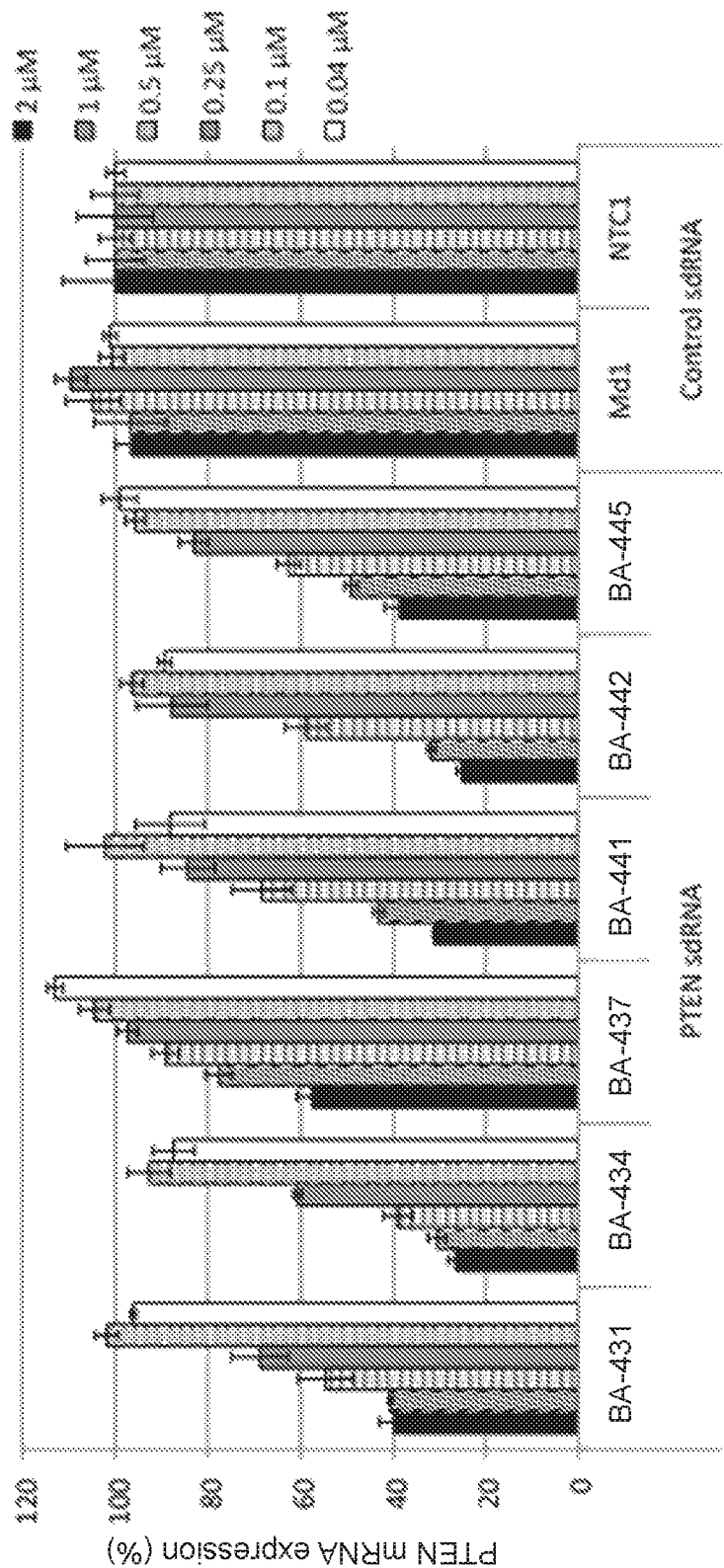
FIG. 6 is a graphic representation showing of a dose-response experiment in a PC12 using indicated sdRNA sequences to silence PTEN expression in comparison to a non-targeting control (NTC)

FIG. 6 shows that all tested sdRNAs reduced PTEN mRNA expression in a dose-dependent fashion in comparison to NTC. Three sdRNAs, BA-434, BA-441 and BA-442 showed the highest potency in reducing PTEN mRNA levels in PC12 cells (FIG. 6)

Example 5

Cross-Reactivity of Rat PTEN sdRNA Compounds in HeLa Cells

Cross-species PTEN targeting agents described herein were identified by comparison of human and rat gene sequences and validated by treating HeLa cells with designed sdRNA compounds. FIG. 35 shows that the BA-434 rat cDNA sequence is exactly homologous to the human cDNA sequence.

For sdRNA transfection, 2 μM solutions of PTEN, MAP4K4 (positive control) and NTC (non-targeting control) sdRNA were prepared in serum-free EMEM medium at 50 μl/well of 96-well plate.

HeLa cells were collected by trypsinization as described in EXAMPLE 1 and dispensed at 6,000 cells/50 μl/well into the plate with pre-diluted sdRNAs and placed in the incubator for 48 hrs.

PTEN expression was determined by qRT-PCR, as described in EXAMPLE 4.

Figure 7:
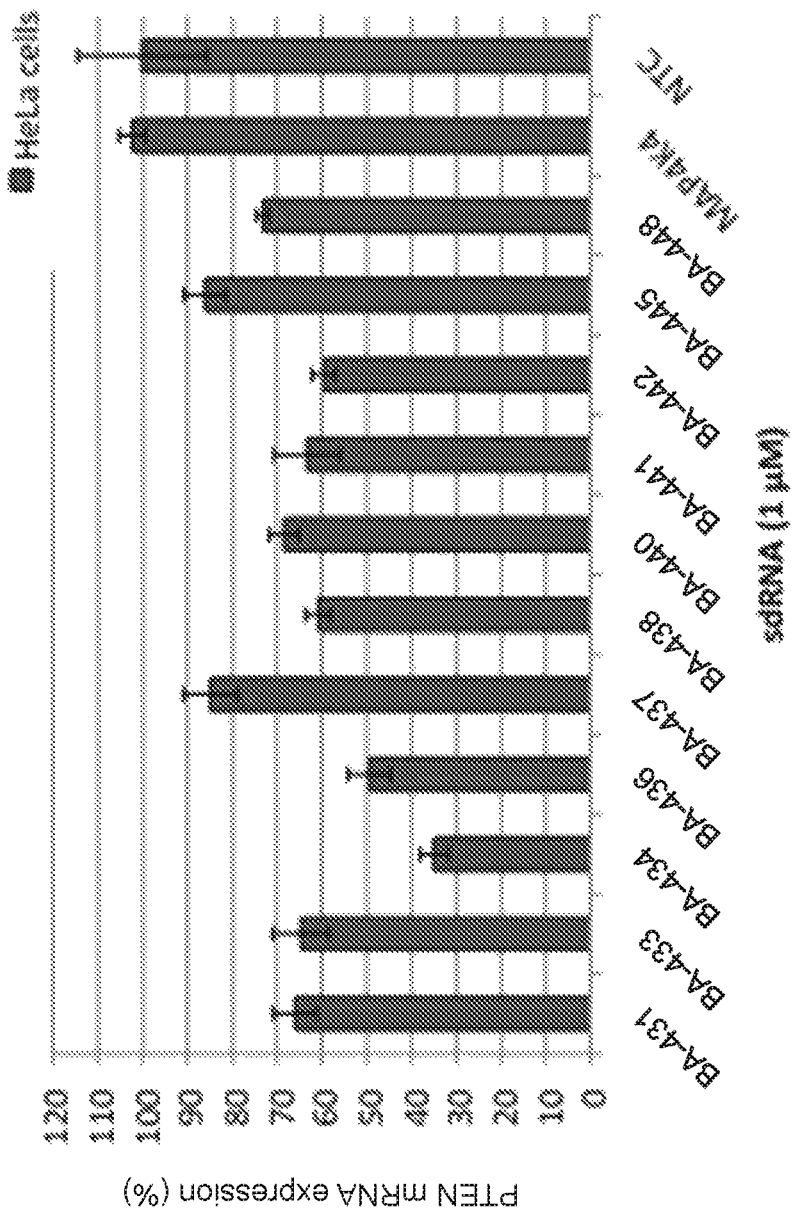
FIG. 7 is a graphic representation showing cross-reactivity of PTEN sdRNA compounds to human PTEN gene in HeLa cells in comparison to NTC (non-targeting control)

Cross-species reactivity of PTEN sdRNA sequences is demonstrated by PTEN gene silencing activity in HeLa cells (FIG. 7). BA-434 showed the highest efficacy in reducing PTEN mRNA in human HeLa cells.

Example 6

Validation of PTEN Silencing in HeLa Cells

The dose response effect of the silencing activity of the most potent PTEN compound identified in EXAMPLE 5, BA-434, was measured in HeLa cells.

Solutions of PTEN sdRNA BA-434 and NTC (non-targeting control) sdRNA were prepared in serum-free EMEM medium. The final concentration range of oligonucleotides was 0.04 μM-2 μM. Treatment with sdRNA (48 hr) and qRT-PCR analysis were performed as described in EXAMPLE 3. PTEN expression was normalized to GAPDH and plotted as percent of expression of NTC sdRNA-treated cells.

Figure 8:
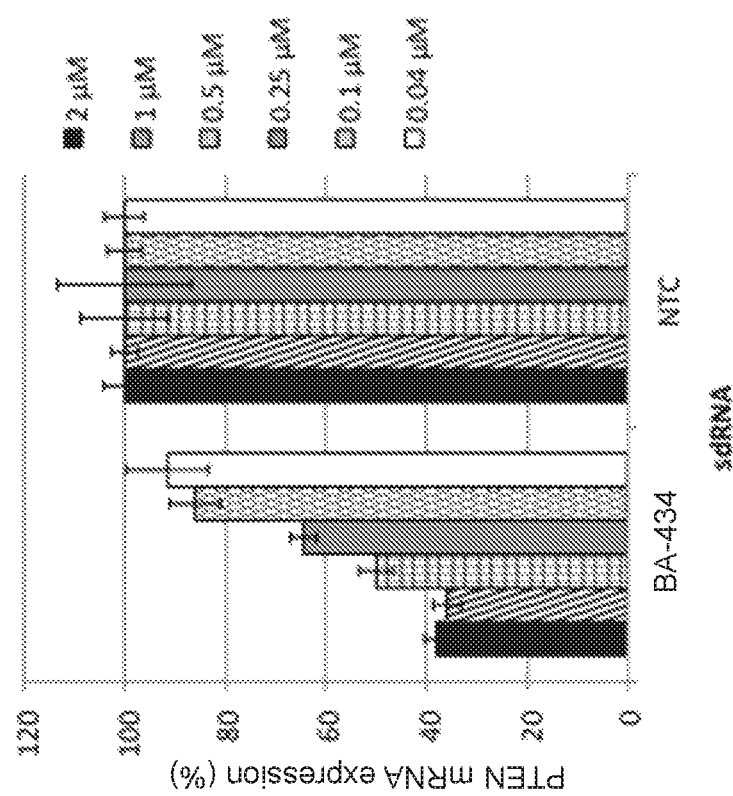
FIG. 8 is a graphic representation showing dose-dependent PTEN gene silencing in HeLa cells induced by BA-434 in comparison to NTC (non-targeting control)

As shown in FIG. 8, PTEN sdRNA BA-434 induces up to 60% reduction in PTEN mRNA expression in HeLa cells.

Example 7

Validation of PTEN sdRNA With Alternative Modification Pattern in PC-12 Cells

Silencing activity of fully stabilized PTEN compound (BA-434_fm) was tested in PC-12 cells for dose-response.

PC-12 cells were cultured and treated with sdRNA as described in EXAMPLE 3. Briefly, cells were treated with BA-434, BA-434_fm or NTC (non-targeting control) sdRNAs at the concentrations 0.04 μM-1 μM for 48 hr. Total RNA was isolated using PureLink Pro96 purification kit and used in one-step qRT-PCR. PTEN expression was normalized to GAPDH and plotted as percent of expression of NTC sdRNA-treated cells.

Figure 9:
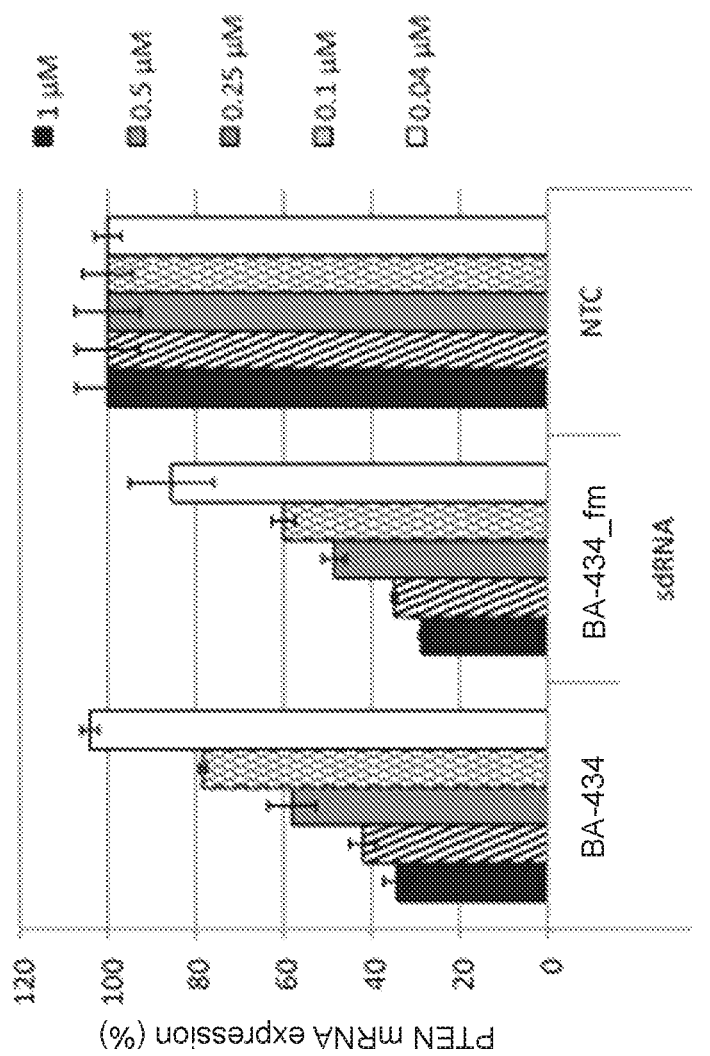
FIG. 9 is a graphic representation showing dose-dependent PTEN gene silencing in PC12 cells by BA-434 sdRNA and a fully modified BA-434 sdRNA (BA-434_fm) with an alternative modification pattern in comparison to NTC (non-targeting control)

FIG. 9 shows that in PC12 cells, fully stabilized PTEN compound BA-434_fm shows higher efficacy in silencing PTEN mRNA expression in comparison to BA-434 compound.

Example 8

Longevity of BA-434_fm-Induced Silencing in PC-12 Cells

Longevity of PTEN gene silencing by BA-434 and BA-434_fm sdRNA was tested in PC-12 cells as follows.

PC-12 cells were cultured and prepared for sdRNA transfection as described in EXAMPLE 3. Cells were treated with BA-434, BA-434_fm or NTC sdRNAs at 1 concentration for 48 hrs. Transfection medium was then changed for the fresh RPMI with 1% FBS and 100 ng/ml NGF. At the specified time (48 hr, 72 hr, 96 hr, and 7 d), cells were washed once with 100 μl/well PBS and once with FCW buffer. After removal of supernatant, cell processing mix of 23.5 μl FCPL and 1.5 μl gDNA wipeout solution was added to each well and incubated for 5 min at room temperature. Lysates were then transferred to PCR strips and heated at 75° C. for 5 min.

For qRT-PCR set up, the lysates were mixed with QuantiTect reagents from the FastLane Cell Multiplex Kit and with primer probe mix for PTEN-FAM/GAPDH-VIC. A volume of 9 μl/well of each reaction mix was mixed with 1 μl lysate per well and amplified using the settings recommended by the manufacturer. PTEN expression was normalized to GAPDH and plotted as percent of expression of NTC sdRNA-treated cells.

Figure 10:
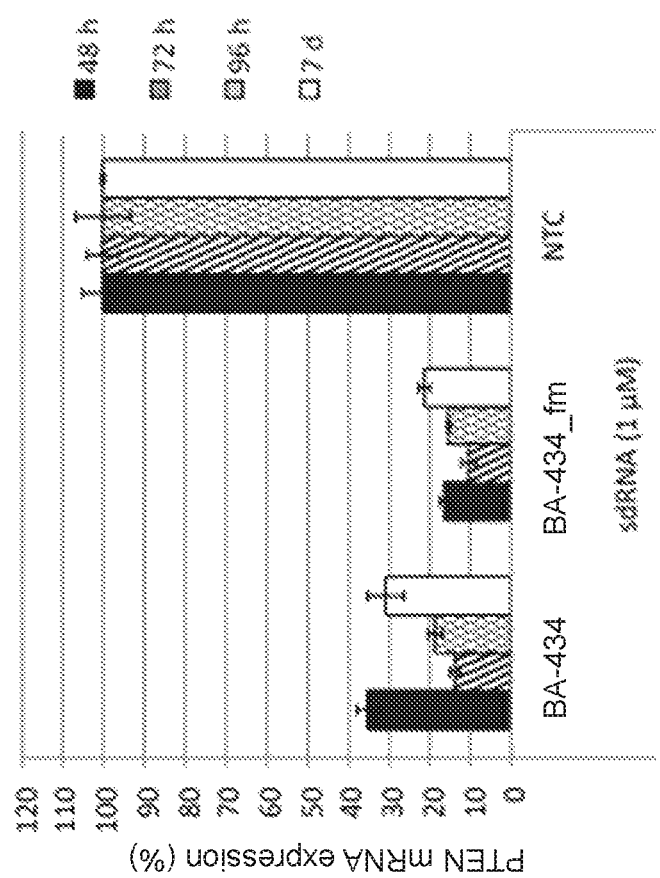
FIG. 10 is a graphic representation showing the stability of BA-434 and fully modified BA-434 (BA-434_fm) sdRNA-induced PTEN gene silencing in comparison to NTC (non-targeting control) in PC12 cells cultured for up to 7 days after administration.

As shown in FIG. 10, the PTEN gene silencing effect is stable for at least 7 days after transfection for both, BA_434 and BA-434_fm. BA-434_fm shows higher potency in reducing PTEN mRNA than BA-434 in PC12 cells.

PC12 cells were grown in DMEM/F12 media with 10% FBS, 5% horse serum, glutamine and Penicillin/Streptomycin, then 30,000 cells per well were plated in 24-well plates coated with collagen.

Example 9

PTEN Expression in PC12 Cells

PC12 cells were grown in DMEM/F12 media with 10% FBS, 5% horse serum, glutamine and Penicillin/Streptomycin, then 30,000 cells per well were plated in 24-well plates coated with collagen.

PC12 cells were treated for 72 hr with 1 μM of BA-441, BA-442, BA-434 or non-targeting sdRNA diluted in DMEM-F12 supplemented with 1% FBS and 100 ng/ml NGF. PTEN protein expression was examined by Western blotting. The primary antibodies used were mouse anti-GAPDH (1:3000 dilution, Santa Cruz, Dallas, Tex.) and rabbit anti-PTEN (1:1500, Cell Signaling Technology, Danvers, Mass.) and corresponding secondary antibodies conjugated to horse radish peroxidase (1:5000, Cell Signaling Technology).

Figure 11:
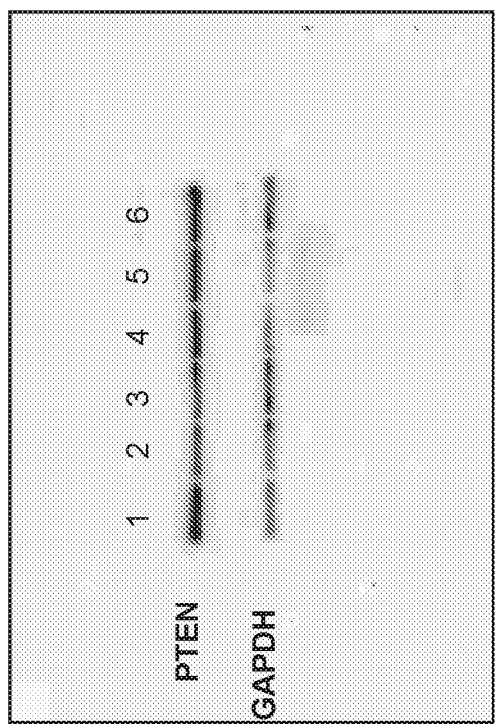
FIG. 11 is a representation of a Western blot showing PTEN protein expression and GAPDH protein expression, where lane 1: non-targeting control; lane 2: BA-434; lane 3: BA-441; lane 4: BA-442; lane 5: Control No RNA; lane 6: Control, no media change, no RNA.

FIG. 11 shows PTEN reduction after treatment with BA-434 and BA-442. The low FBS concentration did not affect PTEN mRNA expression in untreated cells and cells treated with NTC.

Example 10 qPCR Analysis of PTEN Knock-Down in Rat Primary Neurons

Timed pregnant Sprague Dawley rats were purchased from Taconic Biosciences (Rensselear, N.Y.). Animals were euthanized by $CO_2$ asphyxiation and embryonic day 17 (E17) embryos were removed from uterus. The embryo heads were separated, stored in Hibernate-E medium (Life Technologies, Woburn, Mass.) on ice. The cortex and hippocampus of the embryo were isolated from whole brain in DM (dissociation medium: HBSS with 2 mM $MgCl_2$, 0.2 mM kynurenic acid, 2 mM HEPES, pH 7.2) under dissecting microscope, and transferred into a 15 ml conical tubes with DM on ice.

The neuron cells were dissociated in a tissue culture hood. The DM was removed from the cortex and hippocampus tissues, a 5 mL warm sterilized papain/DL-cysteine (12.5 units of papain in 1× DM solution, with DL-cysteine) was added into the tube, and the tube inverted once to mix the brain tissues with solution, which was then incubated at 37° C. water bath for 5 min. The tube was transferred from the water bath into the tissue culture incubator, and brain tissue pieces were allowed to settle down to the bottom of the tube. The papain solution was removed and 5 mL 1% trypsin inhibitor (Worthington, Lake Wood, N.J.) in 1× DM was added to the brain tissue. The tube was inverted and then placed in the oven at 37° C. for 3 min. The trypsin inhibitor was then removed and this procedure was repeated 2 more times. After removal of the final trypsin inhibitor solution, 2 mL of ice cold plating medium was added and the cells triturated with a glass pipette and a latex bulb 10 to 20 times, until tissue was fully dissociated. For cortical neurons from 1 litter (between 8 to 12 embryos), the neurons were placed into 20 mL cold plating medium and trituration was performed as described before.

For plating and culture of the neurons, 24-well plates were pre-coated with 0.1 mg/mL poly-D-lysine overnight and washed with sterile water twice and ready for cell plating. Cortical neurons were plated at a density of 200 k to 400 k cells/well and cultured at 37° C. incubator with 5% $CO_2$. Hippocampus neurons were plated at a density of 5,000 to 20,000 cells/well in 8-well chamber slide pre-coated with PDL.

If the plating medium was DMEM with 10% FBS, 1× P/S, and 1× Glutamax, the medium was exchanged to Neurobasal medium supplemented with 1× B27, 1× P/S, and 1× Glutamax after one day. Half of the cell culture medium was replaced with fresh Neurobasal medium every 4 days.

To examine effects of BA-434 on PTEN mRNA expression in primary neurons, neurons were cultured for 8 days and then treated with different concentrations of BA-434, BA-441 or BA-442 ranging from 0.1 μM to 1 μM. Corresponding concentrations of NTC and MAP4K4 sdRNA were used as negative controls. sdRNAs were diluted in complete neurobasal culture medium and applied to the cells.

RNA was isolated from cells at 72 hr after treatment and PTEN mRNA was analyzed by qPCR. RNA was isolated from neuronal cells using Purelink RNA mini kit (Thermo Fisher Scientific) according to the manufacture's instruction. cDNA was prepared from RNA using High Capacity cDNA Reverse transcription kits (Thermo Fisher Scientific). 500 ng of RNA was mixed in a reaction tube with 10× Reaction buffer, 25× dNTP mix, 10× RT random primers and MultiScribe Reverse Transcriptase. Tubes were loaded on thermal cycler and the following program was run: 25° C. for 10 min, 37° C. for 120 min, and then 85° C. for 5 min to inactivate the RT reaction.

qPCR was performed using SYBR green PCR master mix (Thermo Fisher Scientific) using the following primers specific for PTEN and CSF-1 (housekeeping gene for internal normalization) transcript sequences:

The primers for PTEN transcript sequence are:

5' forward:
(SEQ ID NO: 1)
AAG GAC CAG AGA TAA AAA GGG AGT;

5' reverse:
(SEQ ID NO: 2)
ACC TTT AGC TGG CAG ACC AC;

The primers for CSF-1 transcript sequence are:

5' forward:
(SEQ ID NO: 3)
CAA GGA CTA TAA GGA ACA GAA CGA G (housekeeping gene CSF1);

5' reverse:
(SEQ ID NO: 4)
GAA ATT CTT GAT TTT CTC CAG CA.

25 ng/µL of cDNA diluted 1:5 and 1.5 µL of dilution were mixed with qPCR master mix (Thermo Fisher Scientific). Each reaction was run in duplicate. Ct values were collected and normalized with housekeeping gene CSF1 for each sample (ΔCt). All the samples are then normalized with non-targeting control (NTC) samples (ΔΔCt) and converted to 2^ΔΔCt.

Figure 12:
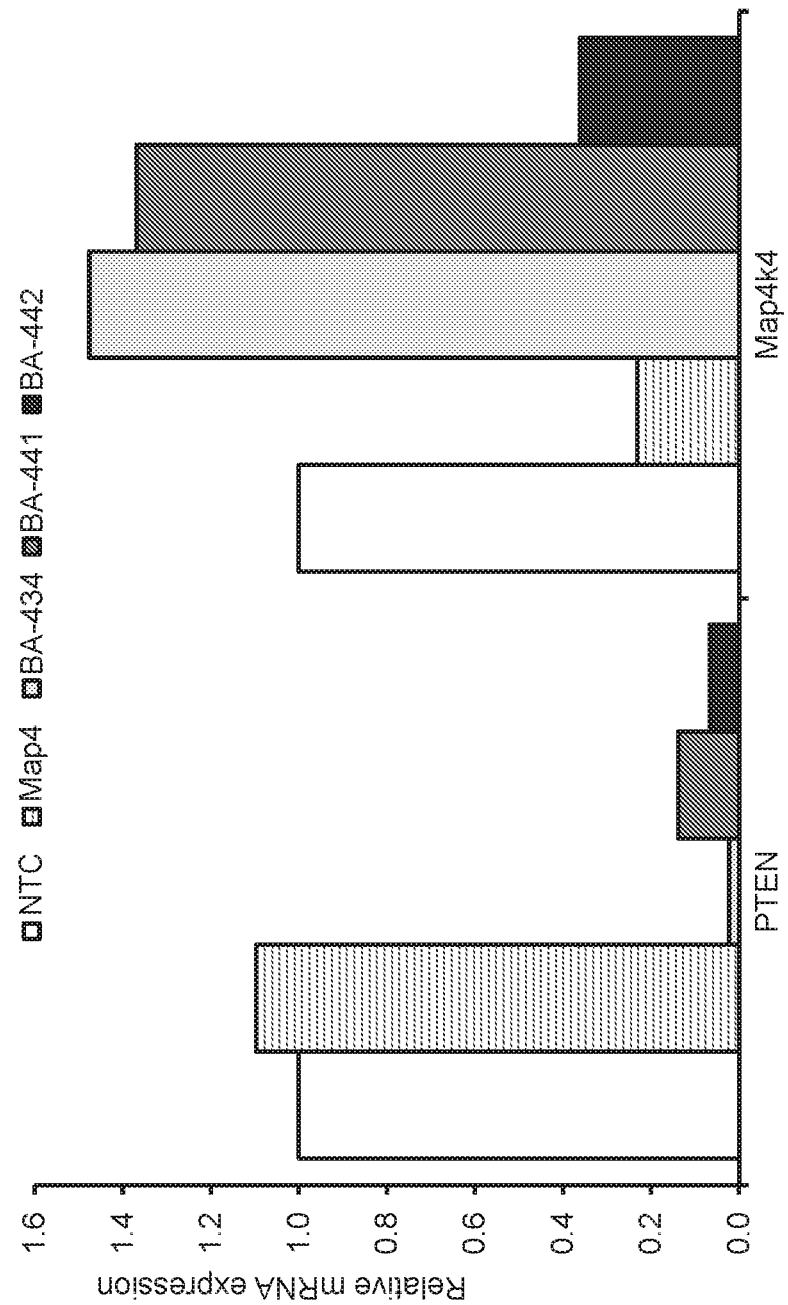
FIG. 12 is a graphic representation showing gene expression of PTEN and MAP4K4 in rat cortical neurons after treatment with BA-434, BA-441, BA-442 or with control sdRNAs with a non-targeting sequence (NTC) or a sequence targeting MAP4k4 (MAP4K4)
Figure 13:
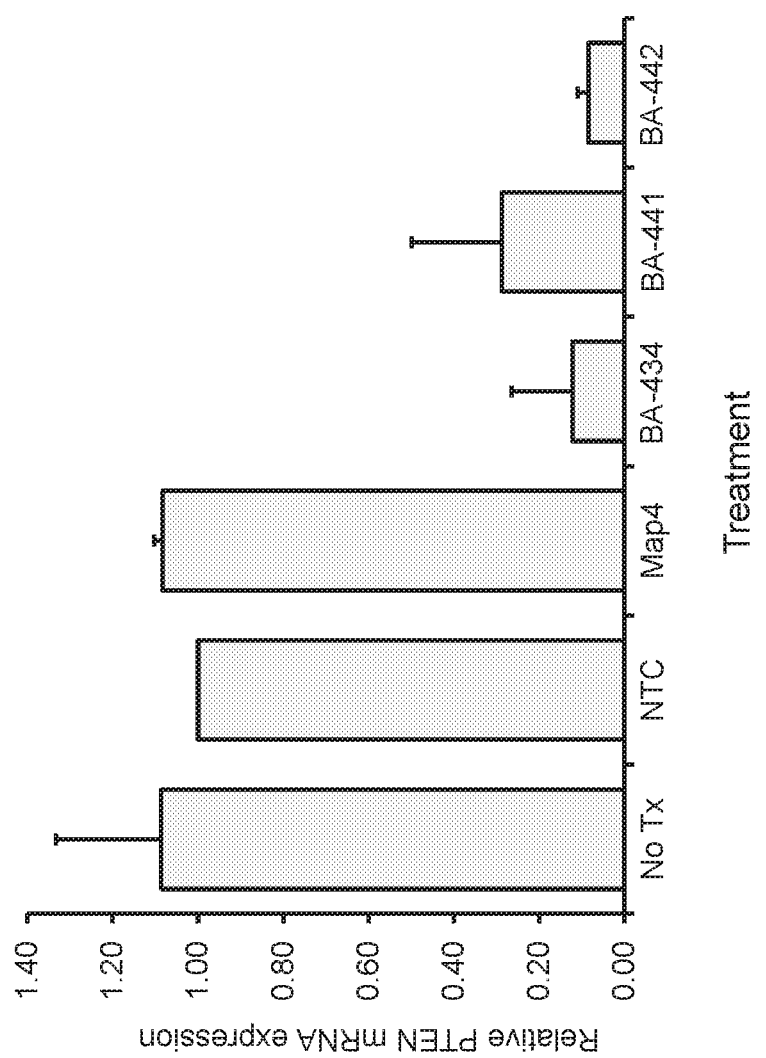
FIG. 13 is a graphic representation showing gene expression of PTEN in rat cortical neurons after treatment with BA-434, BA-441, BA-442 or with control sdRNAs with a non-targeting sequence (NTC) or a sequence targeting MAP4k4 (MAP4K4); No Tx, untreated control.

FIG. 12 shows that BA-434 most effectively reduced PTEN mRNA transcript. Three day treatment with 1 µM BA-434 induced a more than 95% decrease in PTEN mRNA transcript. BA-441 was less effective and induced an 85% reduction in PTEN mRNA transcript after 3 days of treatment (1 µM). BA-442 decreased PTEN mRNA transcript by more than 90% after 3 days of treatment (1 µM), however, this sdRNA also reduced MAP4k4 mRNA and consequently is not specific to PTEN mRNA. The experiments were repeated and similar results were obtained (FIG. 13). Low concentrations of BA-434 at 0.5 µM and 0.1 µM were still effective and reduced PTEN mRNA transcript by 95% or more (FIG. 14). When BA-434 treatment was sustained for 4 and 5 days, PTEN mRNA reduction remained over 90% (FIG. 15), demonstrating sustained treatment efficacy.

Example 11

Protein Analysis in Primary Neurons Treated with sdRNA

Primary cortical neurons were prepared as described in EXAMPLE 10 and cultured for 8 days.

Neurons were treated for 48 hr, 72 hr or 96 hr with 1 µM sdRNAs BA-434, BA-441 and BA-442 and then collected and lysed in RIPA buffer with proteinase inhibiter and phosphatase inhibitors (HALT, Thermo Fisher Scientific). Protein was loaded on 10% Bis-Tris protein gels (Thermo Fisher Scientific), resolved by SDSPAGE and transferred onto Immobilon-P PVDF membrane (Millipore, Billerica, Mass.). The membranes were incubated with antibodies against PTEN (Cell Signaling), Phospho-S6 Serine 240/44 (Cell Signaling), Phospho-Akt Threonine 308 (Cell Signaling), unphosphorylated S6 protein (Cell Signaling) and GAPDH (Santa Cruz). The membranes were washed with TBS-T buffer and blotted with anti-rabbit IgG (Promega) or anti-mouse IgG (Promega) secondary antibodies conjugated with horseradish peroxidase. Proteins were detected by chemiluminescence using Chemi-Doc imager (Biorad, Hercules, Calif.). The densitometric measurements of each band were performed with ImageJ. Values for PTEN and pS6 bands were normalized with the values of GAPDH band.

FIG. 16 show protein levels of PTEN, pS6 and GAPDH (loading control) in primary cortical neurons treated with BA-434, BA-441, BA-442, or NTC sdRNA for 48 hr or 72 hr. Densitometric analysis revealed a maximal decrease in PTEN protein levels at 72 hr for all treatments. However, BA-434 was more effective than BA-441 or BA-442 in reducing PTEN protein levels in rat primary neurons (FIGS. 16A and B). BA-434 treated cells also showed highest levels of phosphorylated S6 (FIGS. 16A and C).

Figure 17A:
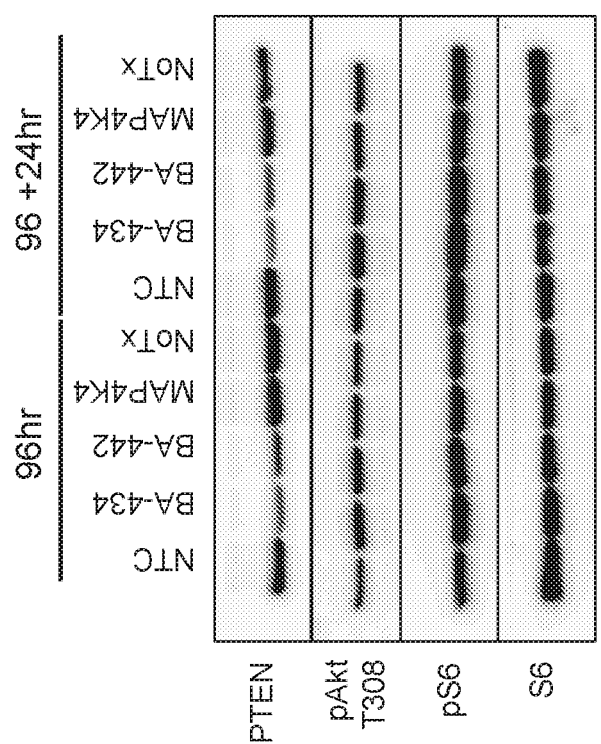
FIG. 17A is a representation of a Western blots showing protein levels of PTEN, phospho-AKT (Threonine 308) phospho-S6 (serine 240/44) and S6 protein in rat primary cortical neurons treated with the indicated sdRNA for 96 hours (96 hr) or treated for 96 hours followed by a medium change and cultured for an additional 24 hours (96+24 hr)

FIG. 17 shows protein levels of PTEN, pAKT Thr 308, pS6 Ser 240/44 and unphosphorylated S6 (loading control) in primary cortical neurons, treated with BA-434, BA-442, MAP4K4 or NTC sdRNA for 96 hr, and then extracted for Western blotting at 96 hr or 120 hrs. Densitometric analysis revealed that both, BA-434 and BA-442 reduce neuronal PTEN protein levels after 3 days of treatment and PTEN protein levels further decrease 24 hr after treatment washout indicating that the treatment efficacy is maintained even without treatment exposure. Both, BA-434 and BA-442 increased Akt and S6 phosphorylation, respectively, which correlates with PTEN protein reduction suggesting that PTEN gene silencing activates AKT/mTOR signaling.

Figures 16B, 16C:
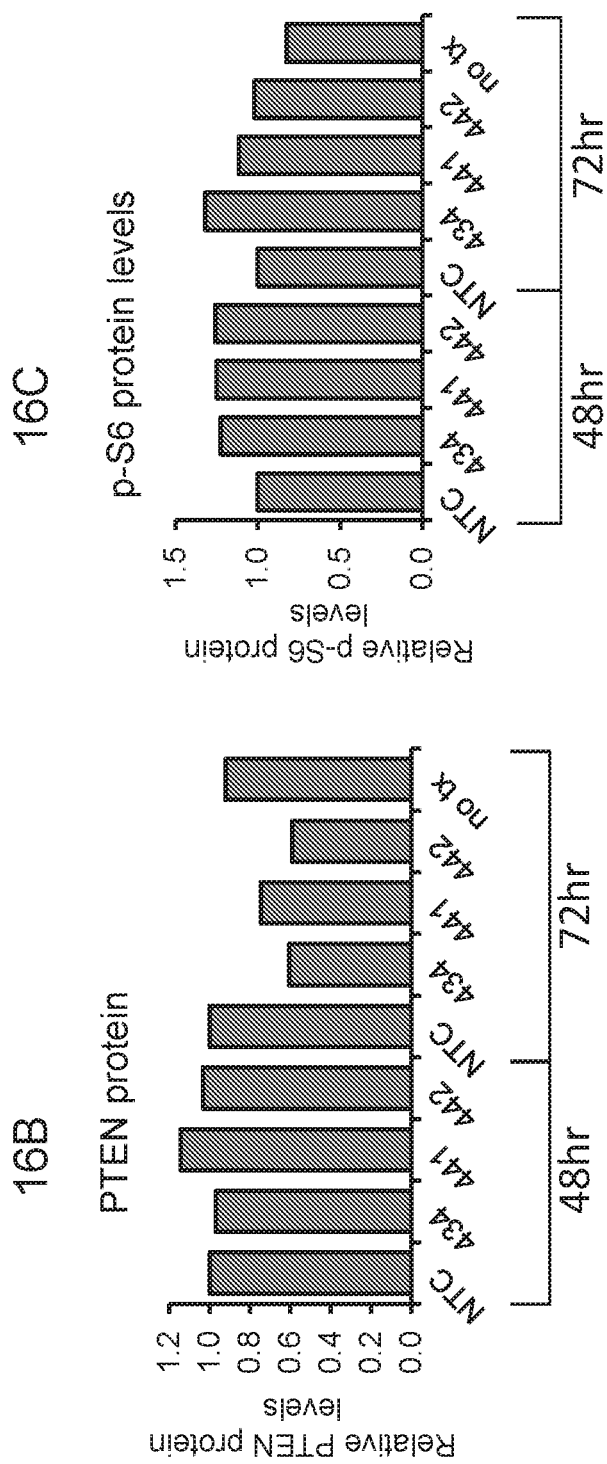
FIG. 16B is a graphic representation showing the expression of PTEN protein after treatment of the primary cortical neuron cultures with the specified sdRNA for either 48 hours or 72 hours; NTC (non-targeting control)
FIG. 16C is a graphic representation showing the expression of phosphoS6 protein after treatment of the primary cortical neuron cultures with the specified sdRNA for either 48 hours or 72 hours; NTC (non-targeting control)
Figure 18:
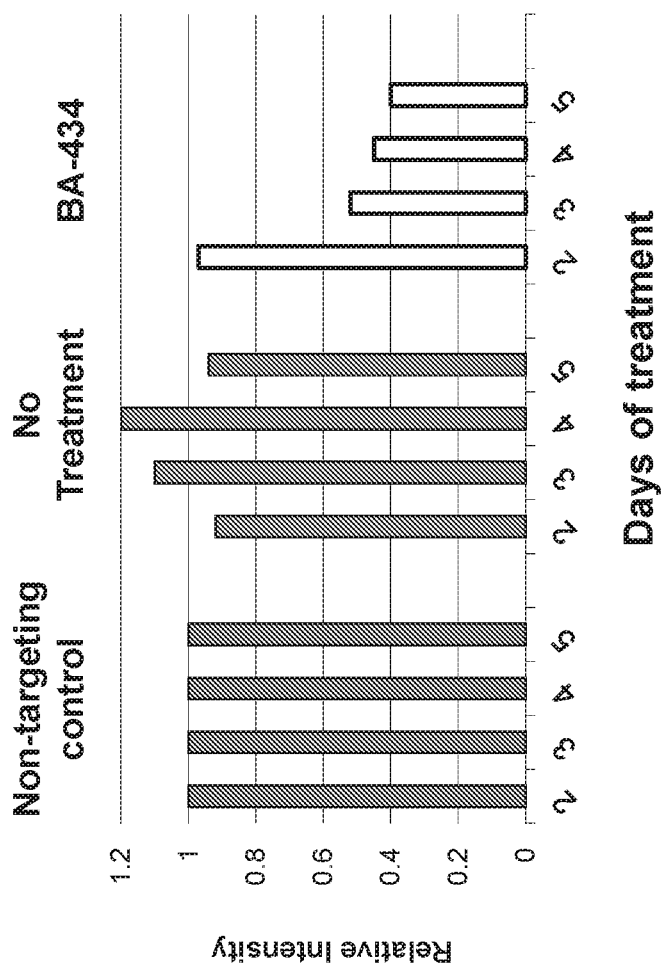
FIG. 18 is a graphic representation of the quantitation of PTEN protein levels in cultured primary cortical neurons after 2, 3, 4, or 5 days of exposure to a non-targeting control sdRNA, a vehicle control, or BA-434 sdRNA.

Use of RNAi for knock down of protein expression is typically effective immediately after it is added to cells in tissue culture. However, when sdRNA was applied to primary cortical neurons, it took at least 3 days to observe PTEN mRNA and protein knockdown (FIGS. 16B and 18). However, when fluorescent PTEN (Cy3-PTEN) is added to cultured cells, Cy3 fluorescence is observed immediately as with other fluorescent sdRNAs tested (FIG. 4). This could indicate that, in neurons, the high cholesterol level in the membrane delays the cleavage of the sdRNA to allow it access to the cytoplasm leading to a sustained delivery even after single dosing.

Example 12

Effect of Modification of BA-434 and Potency of BA-434 in Comparison to Commercially Available Self-Delivering siRNAs To improve the stability of BA-434, the lead sdRNA sequence with highest efficacy in neuronal cells, a fully fluoro- and methyl-modified (34FM) BA-434 (BA-434_fm) was synthesized. BA-434_fm has the same nucleotide sequence as BA-434 but increased fluoro-modification. Efficacy of BA-434 and BA-434_fm were compared against each other and against commercially available Accell sdRNAs produced by Dharmacon (Lafayette, Colo.).

Rat primary neurons were obtained and cultured as described in EXAMPLE 10. After 9 days in culture, cortical neurons were treated for 4 days with 0.1 µM or 0.5 µM BA-434, BA-434_fm or NTC sdRNA or Accell PTEN sdRNA or Accell NTC sdRNA. After 4 days of treatment, neurons were either extracted for PTEN mRNA analysis by qPCR as described in EXAMPLE 10 or for western blotting as described in EXAMPLE 11.

Figures 14A, 14B:
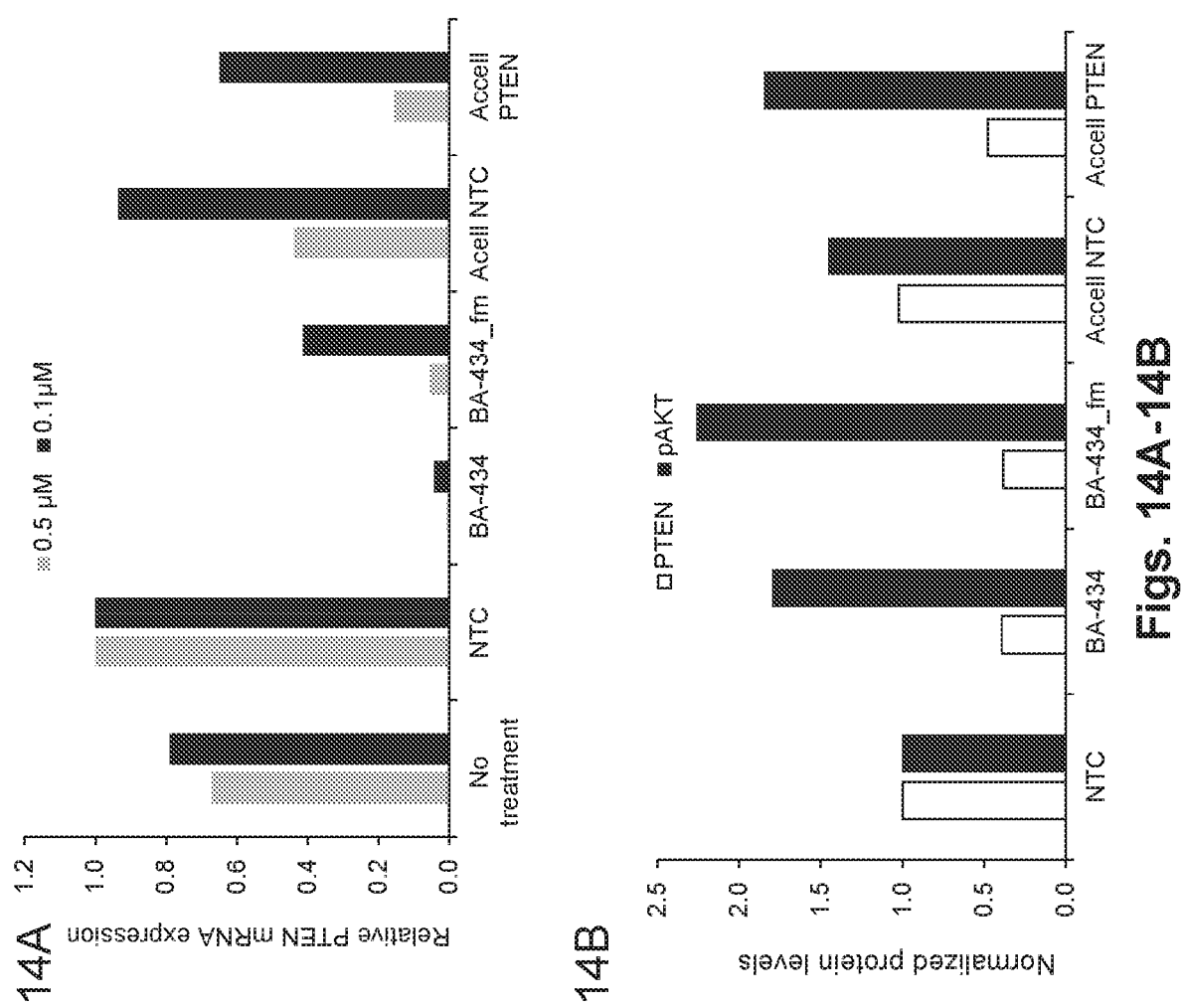
FIG. 14A is a graphic representation showing gene expression of PTEN in rat cortical neurons after treatment with 0.1 or 0.5 µM of BA-434, fully stabilized BA-434 (BA-434_fm), Accell sdRNA targeting PTEN (Accell PTEN) as well as non-targeting controls (NTC and Accell NTC)
FIG. 14B is a graphic representation showing protein levels of PTEN and phosphorylated AKT (Threonine 308 residue) in rat cortical neurons after treatment with 1 µM of BA-434, fully stabilized BA-434 (BA-434_fm), Accell sdRNA targeting PTEN (Accell PTEN) as well as non-targeting controls (NTC and Accell NTC)
Figure 15:
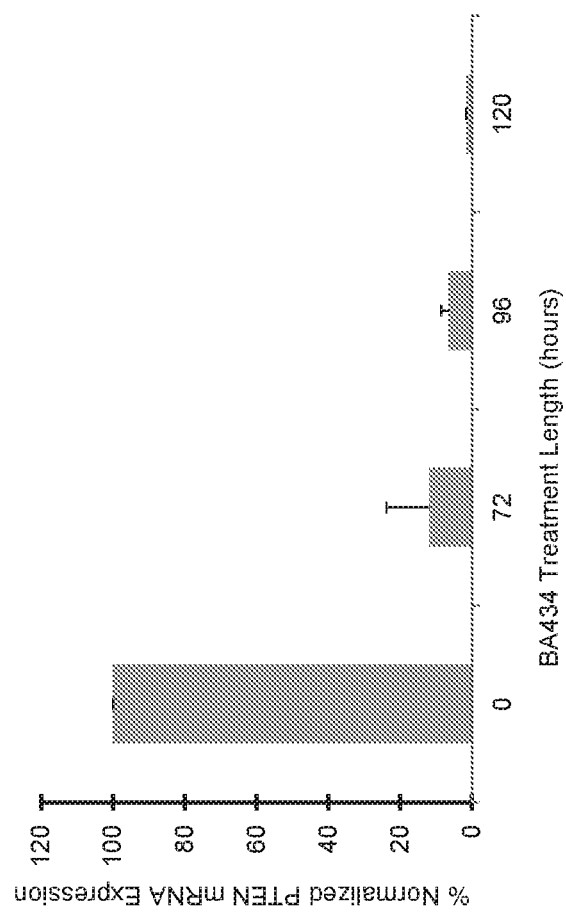
FIG. 15 is a graphic representation showing PTEN mRNA expression in rat cortical neurons 72, 96 and 120 hours after treatment with 1 µM of BA-434 in comparison to untreated cells (0 hr)

FIG. 14 shows that BA-434 possesses higher efficacy in reducing PTEN mRNA compared to both, BA-434_fm (99% vs 95% at 0.5 µM and 95% vs. 60% at 0.1 µM) and Accell PTEN sdRNA (99% vs 95% at 0.5 µM and 95% vs. 35% at 0.1 µM) (FIG. 14A). Western botting revealed that BA-434 and BA-434_fm treatment decreased PTEN protein level by 60%, whereas Accell PTEN sdRNA decreased PTEN protein levels by only 52% (FIG. 14B). Moreover, the BA-434 and BA-434_fm treated neurons showed higher phosphorylation of AKT compared to Accell sdRNA (FIG. 14B).

These results demonstrate that BA-434 sdRNA is a more efficacious compound than commercially available sdRNAs and possesses the optimal nucleotide modification for maximum potency in neuronal cells.

Example 13

Time-Course Analysis of BA-434 in Primary Rat Cortical Neurons

Primary rat cortical neurons from 17 d embryos were obtained from rat cortices (Brainbits Inc. Springfield, Ill.). Cortices were digested with papain and dissociated. After dissociation, cortical neurons were cultured in poly-D-lysine-coated 24-well plates with Neurobasal medium containing NbActiv (Brainbits, Springfield, Ill.), 1% fetal bovine serum and penicillin-streptomycin. After 3 d in culture, cells were treated with 0.01 µM, 0.1 µM, 0.5 µM or 1 µM BA-434 sdRNA or 1 µM non-targeting control (NTC) sdRNA. After 3 d of treatment, sdRNA was washed out from wells by medium exchange. Neurons were extracted either at 1 d, 4 d, 7 d or 11 d after washout (4 d, 7 d, 10 d and 14 d after treatment administration), and then processed for biochemical analysis. PTEN and GAPDH protein levels in cell culture samples were revealed using immunoblotting and measured by densitometry as described in EXAMPLE 11.

Figure 19A:
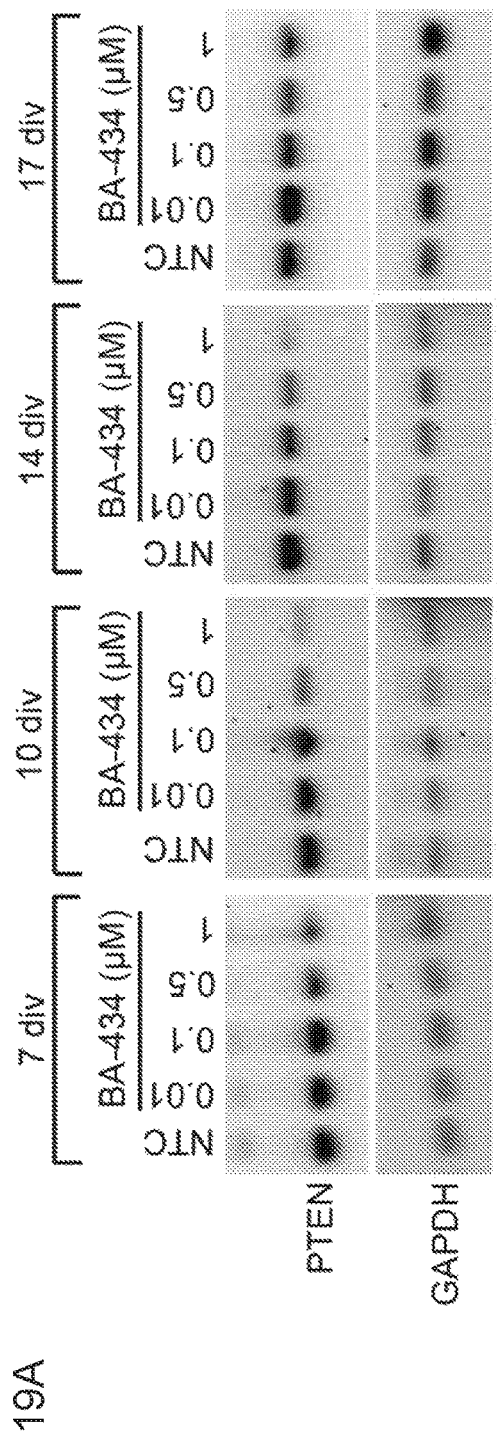
FIG. 19A are representations of Western blots showing PTEN and GAPDH protein levels in primary rat cortical neurons at indicated time-points after treatment with the indicated doses of BA-434.
Figure 19B:
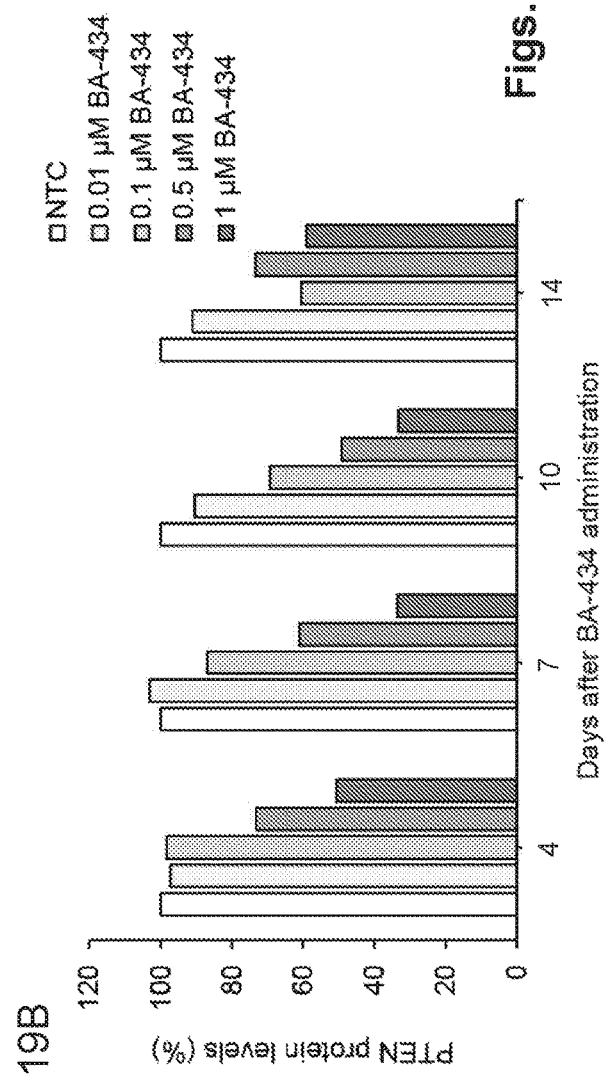
FIG. 19B is a graphic representation of the quantitation of PTEN protein levels in cultured primary rat cortical neurons at indicated time-points after treatment with indicated doses of BA-434.

FIG. 19 shows that PTEN protein levels were reduced in a dose-dependent fashion starting at 4 d after treatment (19A and B). The reduction in PTEN protein levels further decreased at 7 d and 10 d after treatment, although sdRNA was not present in the media for 4 d or 7 d, respectively (FIGS. 19A-B). These results demonstrate that a treatment effect lasts longer than the actual treatment exposure suggesting that a single dose would have extended efficacy. At 10 d after treatment, 7 d after treatment washout, PTEN protein level increased (FIGS. 19A-B), which indicates that the treatment effects on PTEN expression are reversible.

Example 14

Evaluation of Neurite Outgrowth in NGF-Deprived PC12 Cells

PC 12 cells were obtained from ATCC. Cells were plated in collagen-1 (70 µg/ml)-coated 6-well plates and cultured in PC12 growth media containing RPMI basal medium (Gibco®, ThermoFisher Scientific), 10% horse serum, 5% fetal bovine serum and penicillin streptomycin until reaching 80% confluency. Cells were extracted by trypsinization, plated on PDL pre-coated coverslips coated with 5 µg/ml laminin and cultured in DMEM/F12 media supplemented with 1% FBS and 1 ng/ml nerve growth factor (NGF, Peprotech, Rocky Hill, N.J.) for inducing neurite outgrowth. After 3 d in culture, cells were treated with 1 µM BA-434 or 1 non-targeting control (NTC) sdRNA for 3 days. Subsequently, sdRNA was washed out from wells by medium exchange and PC12 cells were kept in culture for one additional day until fixation with 4% paraformaldehyde solution. Cells were labeled with fluorescent antibodies against beta-3 tubulin and with Hoechst® (ThermoFisher Scientific, Waltham, Mass.) nuclear counterstain. 10 images per coverslip were acquired by fluorescence microscopy, and neurite length per image was semi-automatically quantified using the NeuroJ plugin for ImageJ. In addition, total number of neurites and the number of cells with neurites was manually quantified for each image by experimenter blinded to the experimental conditions.

FIG. 20 shows that BA-434 promotes neurite outgrowth in NGF-deprived PC12 cells. In comparison to untreated and NTC-treated PC12 cells, BA-434-treated cells grew more neurite (FIGS. 20 A, C, D) that were longer on average (FIGS. 20A and B). One reason, why injured axons in the spinal cord do not regenerate is the lack of trophic support. All neurotrophins activate phosphatidylinositol 3-phoshate (PI3K)/AKT signaling, which is required for axon growth and regeneration. PTEN counteracts activation of AKT signaling. Thus, these results suggest that treatment with BA-434 compensates for the lack of neurotrophic factors in the injured spinal cord.

Example 15

Effect of PTEN Knock Down on Astrocyte Wound Healing

After mammalian spinal cord injury reactive astrocytes form a glial scar (REF). Migration of reactive astrocyte into the lesion epicenter have a crucial role in CNS wound healing after trauma. Enhancing migration of astrocytes into the lesion site after rodent spinal cord contusion injury promotes seclusion of CNS infiltrating blood borne monocytes, to enhance lesion contraction resulting in a reduced lesion area and to improve recovery of hindlimb function. Increased migration of astrocytes in vitro after astrocyte monolayer wound scratch correlates with increased astrocytes migration and enhanced wound healing in vivo (Okada et al. (2006) *Nature Medicine* 12(7):829-34). PTEN knockout promotes cell migration and wound healing in vivo (Squarize et al. (2010) *PLOS One* 5(5): e10643).

To determine the effects of PTEN knock down by BA-434 on astrocyte migration and wound healing in vitro, primary rat astrocytes (Gibco, Thermo Fisher Scientific). Cells were seeded on PDL precoated glass coverslips (Corning) and grown in DMEM supplemented with 1% N2 (Hyclone, GE Healthcare Life Sciences, Marlborough, Mass.) and 10% FBS (Hyclone) (astrocyte growth media). After 3 d., medium was exchanged to 98% DMEM, 1% N2 and 1% FBS (astrocyte differentiation media) and cells were treated with 1 µM of non-targeting control sdRNA, 1 µM of BA-434 or left untreated. After 3 d of treatment, media was exchanged to astrocyte growth media to washout sdRNA.

After sdRNA washout, astrocyte monolayer was scratched with a sterile 100 uL pipette tip to induce an in vitro wound in the monolayer. 3 d after wounding cells were fixed using 4% PFA. Cells were immunolabeled with fluorescent GFAP antibodies. The in vitro wound was imaged using an epifluorescence microscope. The cell free area of the in vitro wound was measured using ImageJ plug-in.

Figure 21A:
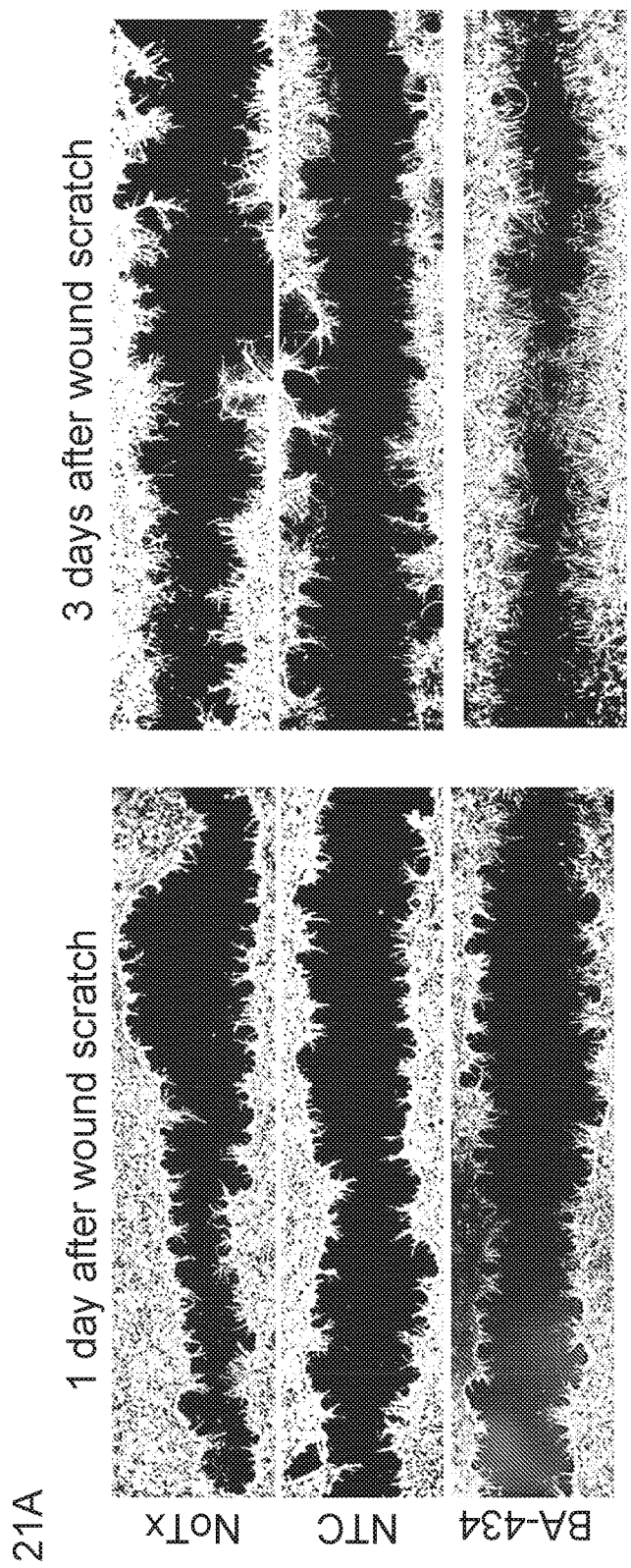
FIG. 21A is a set of representations of micrographs showing an astrocyte monolayer after scratch wounding at different time-points after scratch wound, showing that treatment with BA-434 promotes astrocyte migration and growth into the area of the scratch wound in comparison to untreated and non-targeting control (NTC) treated astrocytes.
Figure 21B:
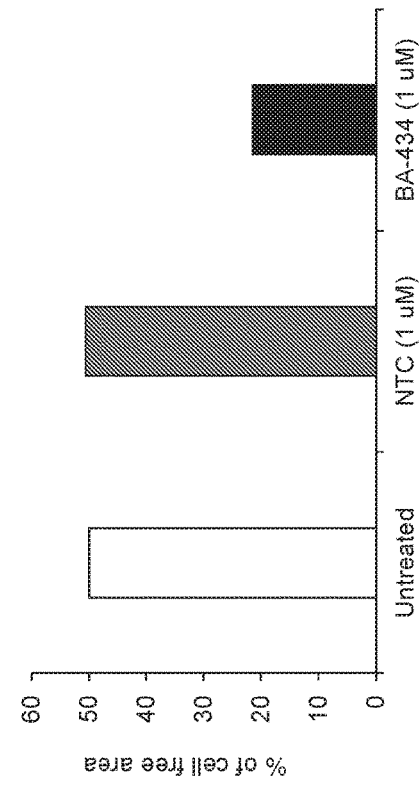
FIG. 21B is a graphic representation showing the quantification of wound area, as defined as cell free area, 3 days after wounding indicating that wound closure is more rapid in BA-434 astrocyte monolayers in comparison to untreated and non-targeting control (NTC) treated astrocytes.

FIG. 21 shows that after wound scratch, BA-434 treated astrocytes grew into the in vitro wound (FIG. 21A) resulting in a reduced the cell-free area after 3 days (FIG. 21B). These results suggest that BA-434 promotes astrocyte migration and astrocyte wound healing and spinal cord repair after injury. Contrary to current beliefs, promoting astrocyte migration aids rather than prevents CNS axon regeneration (Anderson et al. (2016) Nature. 532:195-200).

Example 16

PTEN Expression in Retinal Tissue

To determine PTEN expression in the normal retina, immunocytochemistry techniques were used. The eyes of adult rats were removed and fixed by immersion in 4% paraformaldehyde in 0.1 M phosphate buffer. The retinas were dissected, and prepared as flattened whole-mounts, immersed for 1 hr in the fixative solution, and rinsed in buffer, and left 4 h in a solution of 3% bovine serum albumin (BSA) with 2% Triton-X (blocking solution) with rabbit antibodies against PTEN (Cell Signaling). The retinas were rinsed in PBS+2% Triton-X then incubated in blocking solution with mouse antibody against NF-200 (BioLegend, San Diego, Calif.). After rinsing in PBS+2% Triton-X the retinas were incubated with the following secondary antibodies: Cy3-conjugated goat anti-rabbit antibody and a FITC-conjugated goat anti-mouse antibody. After rinsing in PBS+2% Triton-X 3 times over 1 hr, the retinas were given a final rinse in PBS, and then flat mounted on slides for viewing with a fluorescent microscope.

Figure 22:
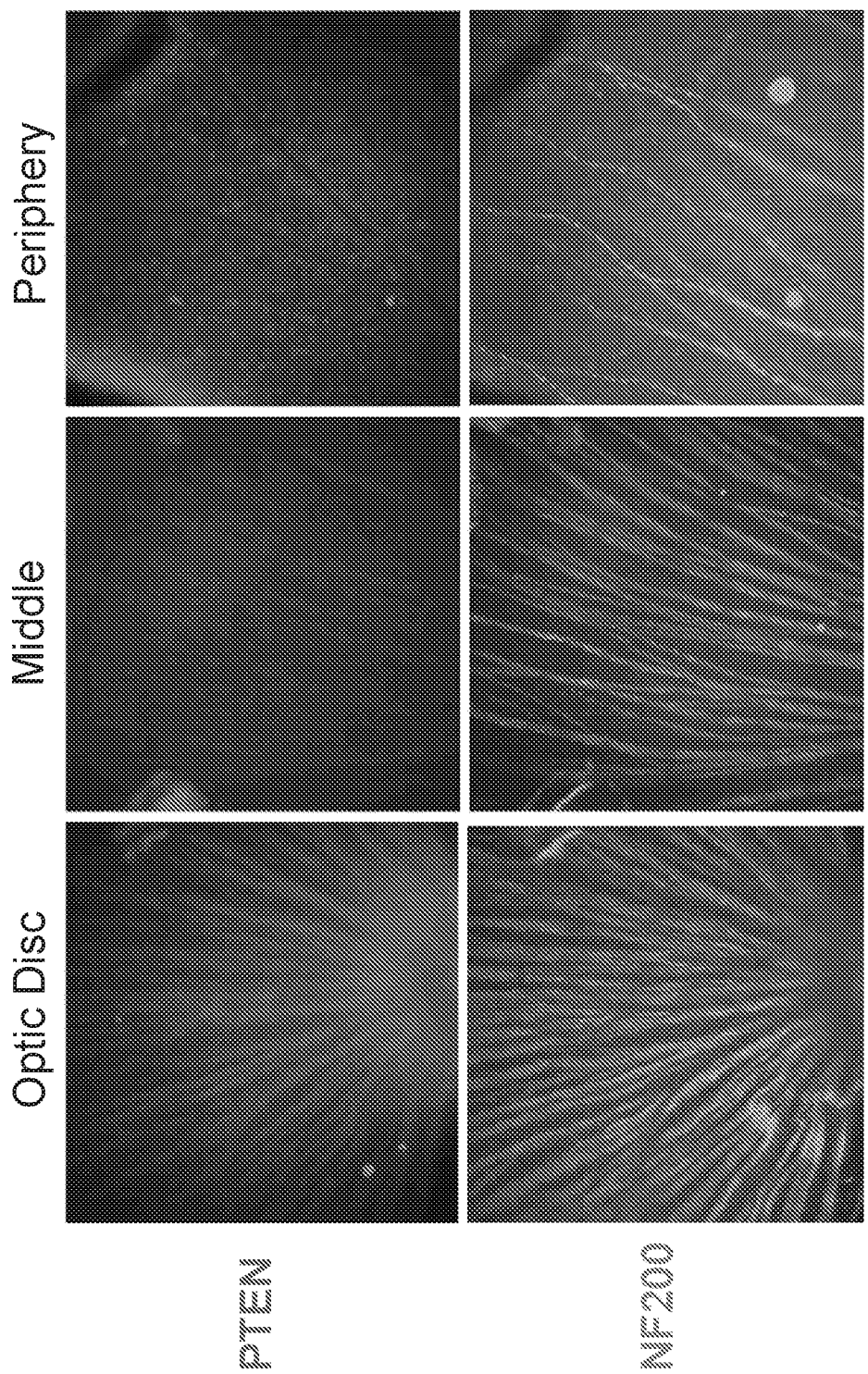
FIG. 22 is a series of representations of low power fluorograms of immunofluorescence staining of a whole mount of the rat retina stained for either PTEN protein (in red) or for neurofilament protein (NF200; in green) at locations near to the optic disc, in the middle radial portion of the retina or at the distal periphery of the retina.

In FIG. 22 three areas from a single retina are shown. The left panel shows the region near the disc, the middle panel is an image from the center of the retina, and the right panel is an image from the peripheral retina. It can be seen that there is strong PTEN immunoreaction near the disc region, and axons in the peripheral region are not labelled for PTEN. This pattern of PTEN expression of the retina correlates with the regenerative ability of RGC axons: axons near the periphery of the retina have a robust regenerative ability, those near the disc regenerate less robustly.

Example 17

PTEN Immunoreactivity in Retinal Tissue

Using the same whole-mount techniques described in EXAMPLE 14, retinas were prepared to examine PTEN immunoreactivity.

Figure 23:
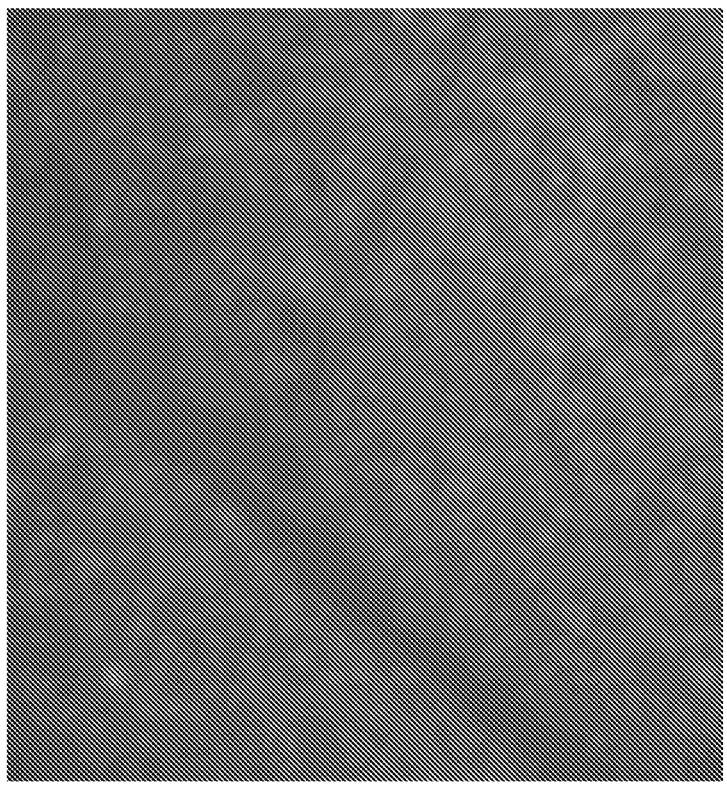
FIG. 23 is a representation of a moderate magnification of the periphery of the rat retina stained via immunofluorescence for PTEN protein identifying the retinal ganglion cell bodies.

FIG. 23 shows that the RGC cell bodies react strongly with PTEN, even in the periphery, despite the absence of immunostaining in their axonal processes.

Example 18

Knockdown of PTEN in Retinal Tissue

To investigate the ability of BA-434 to knockdown the expression of PTEN in the retina, 46 µg Cy3-BA-434 were injected into the vitreous in a total volume of 5 µL using a Hamilton syringe inserted into the posterior chamber without damaging the lens. The needle was inserted in the sclera just above the radial edge of the retina so that the retina was not touched by the needle. For this procedure, the rats were anesthetized, the eye was immobilized between 2 gloved fingers, and the sclera was punctured at the nasal superior aspect of the retina. The compound was injected into the vitreous using 1 mm of the Hamilton syringe capillary needle.

For the whole mount preparation, the superior aspect of the eye was identified by tying a silk suture to the tissue so that the eye orientation could be identified after removal. During the preparation of the retina, whole mount was prepared (as described in EXAMPLE 16). A longer, deeper cut was made in the superior part of the retina during the flat mount procedure to allow identification of the orientation of the retina on the slide, which allows precise localization of the quadrant of the eye where the test BA-434 was injected.

Figure 24A:
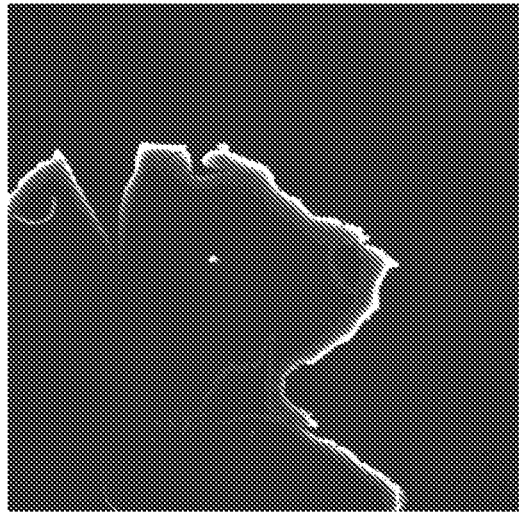
FIG. 24A is a representation of a fluorogram of low power (2×) micrograph of a whole mount of a rat retina for overall retinal tissue.
Figure 24B:
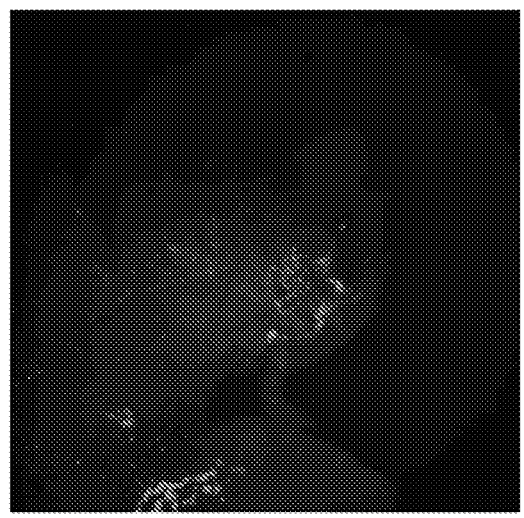
FIG. 24B is a representation of a fluorogram of low power (2×) micrograph of a whole mount of a rat retina for localization of injected, fluorescently labeled BA-434.
Figure 24C:
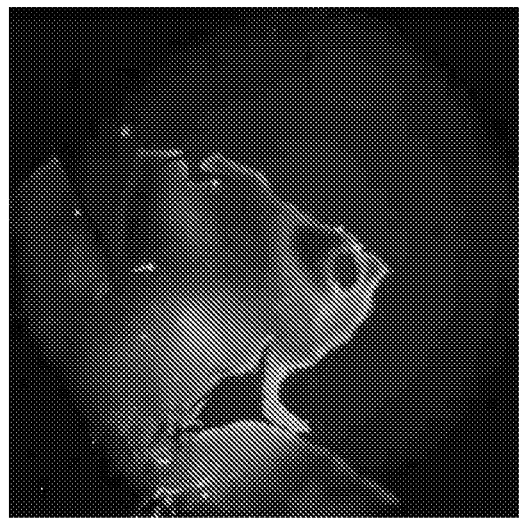
FIG. 24C is a representation of a fluorogram of low power (2×) micrograph of a whole mount of a rat retina for immunofluorescent staining for PTEN protein 4 days after intravitreal injection of sdRNA BA-434.

FIG. 24 shows a whole mount preparation. The Cy3-BA-434 was located throughout the retina, with a higher concentration where the compound was injected which the lower right quadrant of the eye is shown in the photograph. PTEN immunolabeling of the retina, shown in FIG. 24C, was reduced at the injection site.

Figure 25:
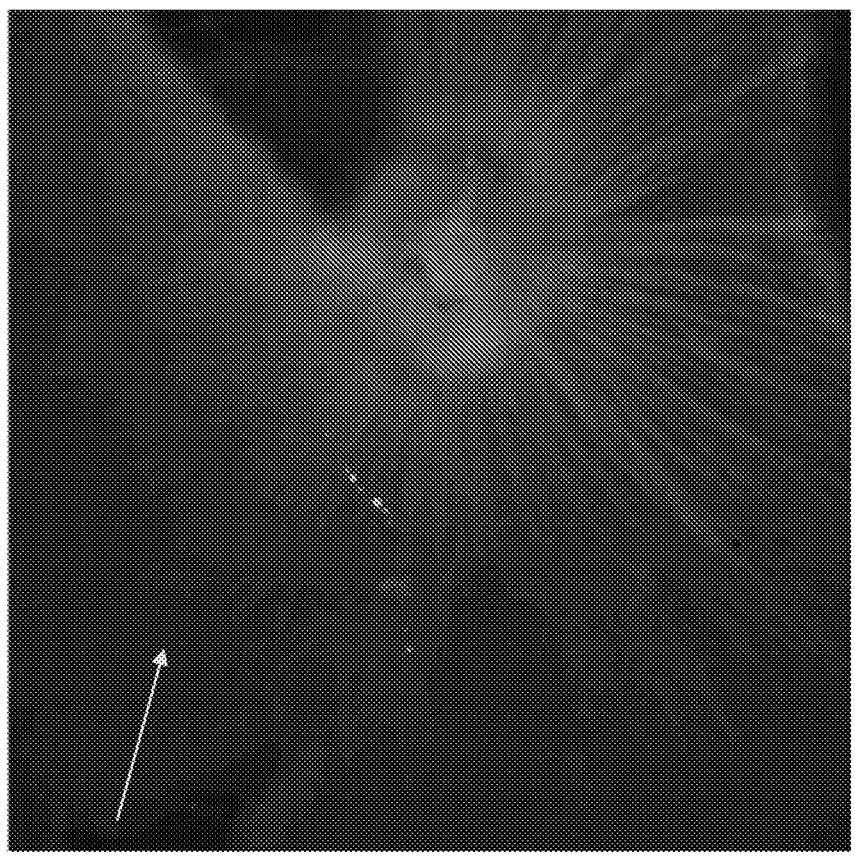
FIG. 25 is a representation of a fluorogram of a higher power view of a rat retinal whole mount stained for PTEN protein 4 days after intravitreal injection of BA-434, where the arrow indicates injection region where axonal PTEN staining is clearly reduced.

At higher magnification of a BA-434-treated retina, there is the greatest loss of immunoreaction of axonal PTEN in the quadrant of the retina closest to the injection site (FIG. 25). Western blots of the retinas indicate that there is knockdown throughout the retina, but the magnitude of knockdown is variable across the retina at 4 days. Observation in the optic nerve shows that PTEN is routinely present in RGC axons (FIG. 28) and the expression of PTEN changes after axon injury. An upregulation of PTEN after axonal injury is detrimental to successful axon regeneration and knockdown of PTEN facilitates regrowth.

Example 19

Time-Course Analysis of PTEN Protein Knock-Down in Rat Retina after BA-434 Intravitreal Administration The left eye of 12 adult rats was intravitreally injected with 40 µg BA-434 as described in EXAMPLE 15. As the control, 3 rats were similarly injected with 40 µg NTC (non-targeting control) sdRNA. Whole retinas from the left and right eye of each rat were extracted at 4 d, 7 d, and 14 d after injection of BA-434 (3 rats per time point) or 14 d after injection of NTC, respectively, and snap frozen in liquid nitrogen.

Tissue weight was measured and an equivalent volume of lysis buffer (Boston Bioproducts, Boston, Mass.) was added to each sample. Retinas were homogenized inside lysis buffer using a 16-gauge needle syringe. Samples were incubated on ice for 30 min and then centrifuged at 10,000 rpm for 10 min at 4° C. Supernatant was transferred to a new tube and mixed 3:1 with Laemmli buffer (BioRad). Samples were boiled at 95° C. for min.

Samples were subjected for SDS-PAGE as described in EXAMPLE 11 for protein separation. Proteins were transferred on PVDF membranes (Millipore). Membranes were immunolabeled with antibodies against PTEN (Cell Signaling) and GAPDH (Santa Cruz).

PTEN and GAPDH protein levels were revealed by chemiluminescence and measured using densitometric analysis as described in EXAMPLE 11. PTEN levels were normalized against GAPDH and the ratio between left (treated) and right (untreated) eye was determined for each individual animal.

PTEN and GAPDH levels were also investigated in pooled samples, which contained 10 µg of each individual animal per group. In pooled retina samples, levels of phosphorylated AKT (pAKT), glycogen synthase kinase beta (pGSK3β) and ribosomal protein S6 (pS6rb) as well as the corresponding unphosphorylated protein (AKT, GSK3β and S6rb) were also examined as described above.

Figures 26A, 26B:
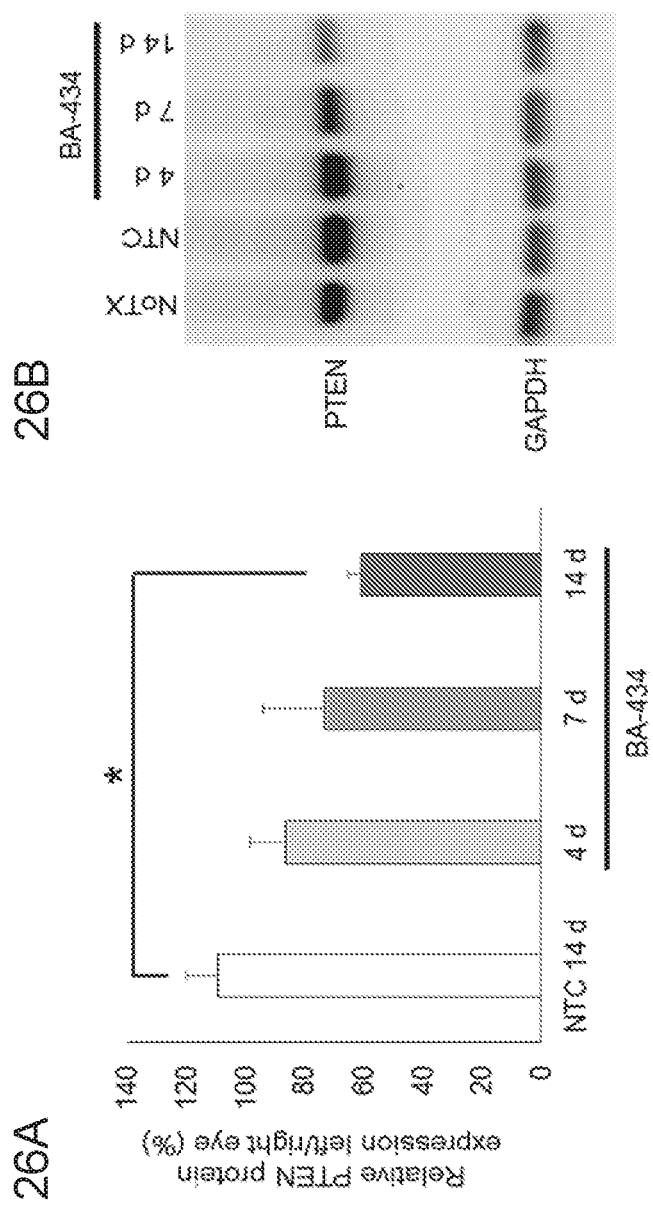
FIG. 26A is a graphic representation showing the quantitation of PTEN protein levels in whole retinal homogenates extracted at 4, 7 and 14 days after intravitreous injection of BA-434 or 14 days after intravitreous injection of non-targeting control (NTC), respectively (plotted are means±SEM. N=3 animals per condition. $P^* < 0.05$ by Student's t-test)
FIG. 26B is a representation of an immunoblot for PTEN and GAPDH (loading control) of pooled retinal homogenates (N=3 animals per condition) showing PTEN protein decrease over time after BA-434 injection.
Figure 27A:
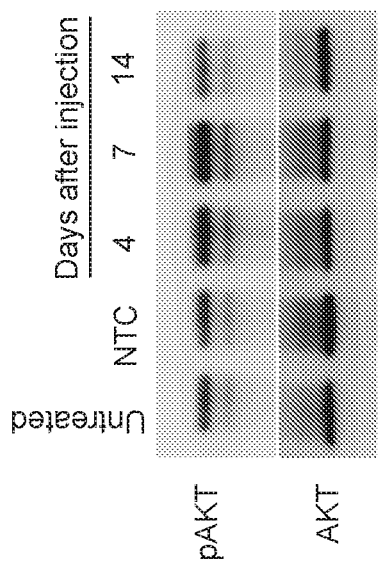
FIG. 27A is a representation of an immunoblot for phosphorylated AKT and unphosphorylated (total) AKT (loading control) of pooled retinal homogenates (N=3 animals per condition) showing increased amount of activated (phosphorylated) AKT at 4 and 7 days after BA-434 injection indicating increased activity of pro-regenerative AKT signaling.
Figure 27B:
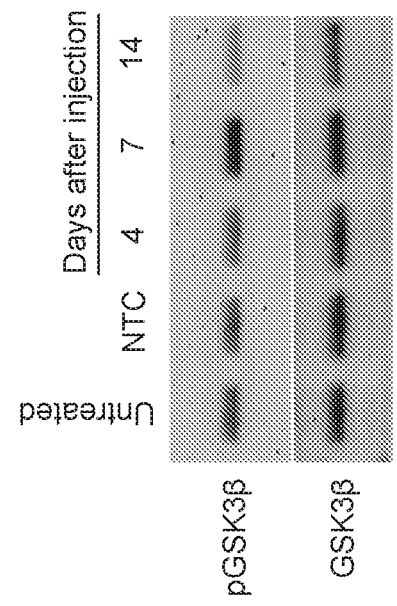
FIG. 27B is a representation of an immunoblot for phosphorylated glycogen synthase kinase 3 beta (GSK-3β) and unphosphorylated (total) GSK-3β (loading control) of pooled retinal homogenates (N=3 animals per condition) showing increased amount of inactivated (phosphorylated) GSK-3β at 7 days after BA-434 injection indicating decreased activity of axon growth inhibitory GSK-3β signaling.
Figure 27C:
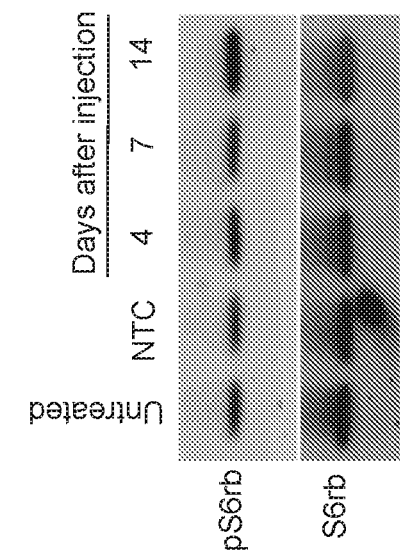
FIG. 27C is a representation of an immunoblot for phosphorylated ribosomal protein S6 (S6rb) and unphosphorylated (total) S6rb (loading control) of pooled retinal homogenates (N=3 animals per condition) showing increased amount of activated (phosphorylated) S6rb at 14 days after BA-434 injection indicating increased activity of pro-regenerative mTOR signaling.

FIG. 26 shows that BA-434 reduced PTEN protein levels in the rat retina in a time-dependent fashion. While at 4 d after BA-434 treatment, PTEN protein levels were comparable with non-targeting control and untreated eyes, PTEN protein was markedly reduced at 7 and 14 d after BA-434 treatment in comparison to control. FIG. 27 shows that reduction in PTEN protein correlated with increase phosphorylation of AKT (FIG. 27A), GSK-3beta (FIG. 27B) and (FIG. 27C). These results suggests that PTEN knock down with BA-434 activates intracellular signaling pathways in retinal ganglion cells, which promote axon regeneration after injury.

Example 20

Promotion of Axon Regeneration by BA-434

To determine the ability of BA-434 to promote axon regeneration, an optic nerve crush model was used.

For surgery, the head was immobilized with a rodent head holder/gas mask and the periorbital area was shaved and prepared by cleaning with 70% alcohol followed by iodine (Povidone solution). The skin was opened along the mid-line of the skull and retracted laterally to expose the left superior orbital rim. An incision was made in the rim periosteum to access the superior aspect of the left orbit. The superior rectus and oblique muscles were sectioned near their insertion in the eye and the retractor bulbi muscle was opened longitudinally to access the optic nerve (ON) at its exit from the eye. The optic nerve was crushed with fine forceps or by tying a 10-0 fine suture around the nerve. This procedure was done after lifting the nerve out of the sheath to avoid damaging the ophthalmic artery. The optic nerve was crushed, and at the same time 40 µg BA-434 or non-targeting control (NTC) sdRNA was injected into the eye, as described in EXAMPLE 16. In all animals, the left eye was the treated eye and the right eye was untreated (without optic nerve injury). Following optic nerve crush the retinal blood flow was assessed by direct ophthalmoscopy of the eye fundus through the operating microscope. When necessary, eye fundus examination was facilitated by a drop of 1% tropicamide (Alcon). Animals that show ischemia were euthanized.

Two weeks later 0.5% cholera toxin beta (CTB) subunit conjugated to Alexa 555 (Thermo Fisher Scientific) was injected intravitreally into the left eye to anterogradely label the retinal ganglion cells (RGCs) and their injured axons. Twenty-four hours after injection of CTB, the animals were deeply anaesthetized and then transcardially perfused with 4% paraformaldehyde solution. After perfusion and a 1 cm piece of optic nerve, with the injury site in the center, were extracted and transferred to 30% sucrose solution for 48 hrs. The optic nerve was embedded in Shandon M-1 embedding matrix (Thermo Fisher Scientific) and snap-frozen in cold (−80° C.) isopentane. 15 µm longitudinal sections of the optic nerve were prepared using a Leica cryostat and mounted on Superfrost Plus microscope slides (Thermo Fisher Scientific).

Figure 28A:
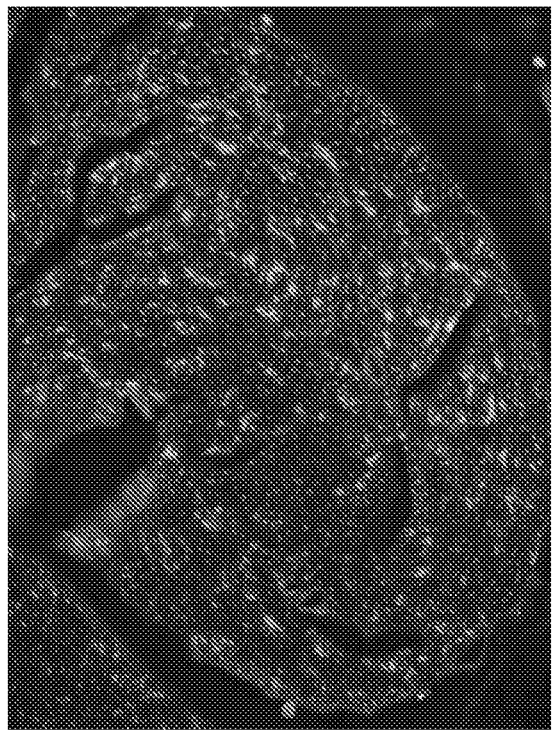
FIG. 28A is a representation of fluorogram of an optic nerve sectioned in longitudinal and double fluorescently stained for PTEN protein (green) and βIII-tubulin (red)
Figure 28B:
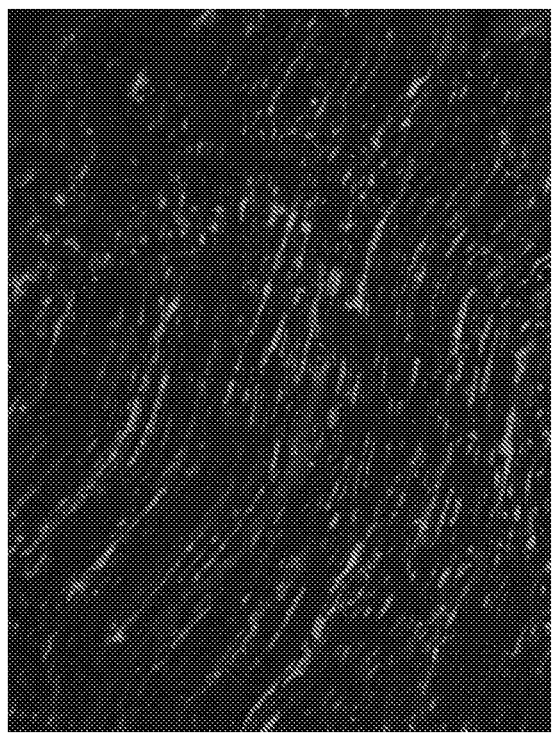
FIG. 28B is a representation of fluorogram of an optic nerve sectioned in cross-sectional plane and double fluorescently stained for PTEN protein (green) and βIII-tubulin (red)
Figures 29A, 29B, 29C:
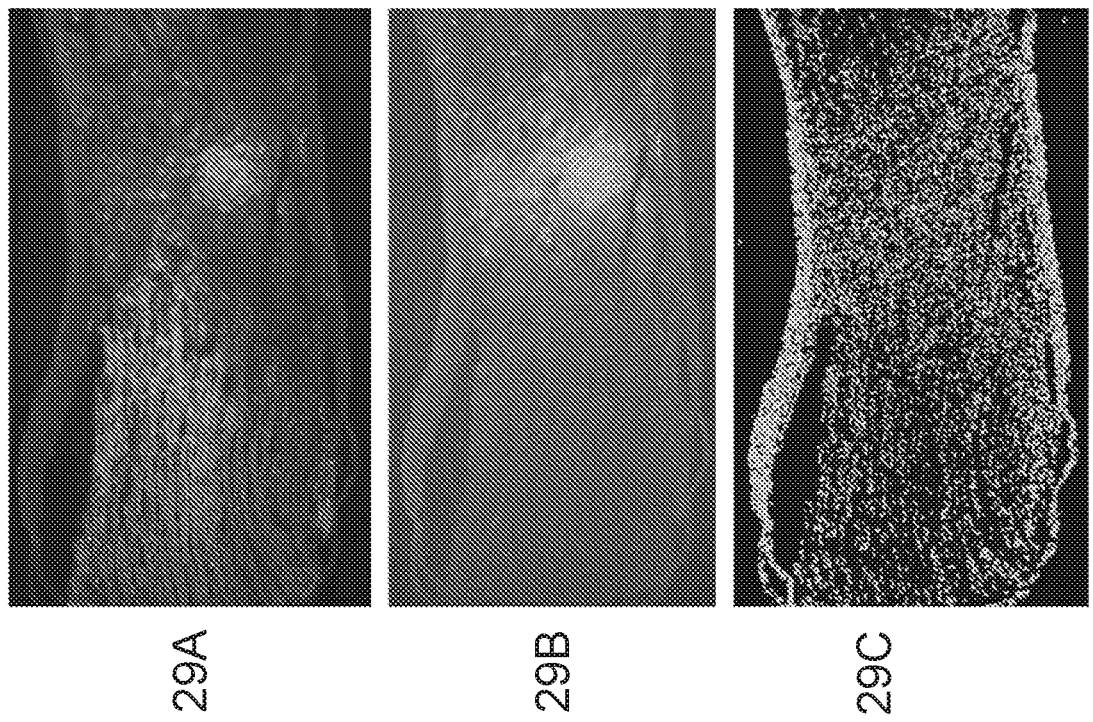
FIG. 29A is a representation of a fluorogram of the injured rat optic nerve labelled with fluorescent cholera toxin, which is used as a nerve pathway tracer.
FIG. 29B is a representation of a fluorogram of the injured rat optic nerve fluorescently labeled with Iba-1 antibodies to identify inflammatory immune cells that have become localized to the injury site.
FIG. 29C is a representation of a fluorogram of the injured rat optic nerve fluorescent labeled with DAPI showing the cellular disorganization at the injury site.

Sections were immunolabeled with rabbit anti-IBA-1 primary antibodies and corresponding secondary fluorescent antibody as described in EXAMPLE 13 as well as with DNA-binding dye DAPI (Thermo Fisher Scientific). Sections were then imaged using a Nikon epifluorescence microscope. FIG. 28 shows a longitudinal image of the crushed optic nerve from a control animal. Injured axons do not regenerate through the lesion site and the axonal tips remain close the rostral lesion border (FIG. 29A). The lesion site can be unambiguously identified because it accumulates IBA-1 positive immune cells immune cells (FIGS. 29B and C).

GAP43 is only expressed in growing axons during development or during regeneration. To determine if BA-434 can induce long-distance regeneration, after applying BA-434 to the eye after optic nerves crush the sections were immunolabeled with anti-GAP43 antibody (Abcam, Cambridge, Mass.) as described in EXAMPLE 13. FIG. 30 shows that after BA-434 treatment markedly more CTB-positive axons were visible inside and behind the injury site. These axons were also GAP-43 positive (FIG. 30C) demonstrating that they were regenerating through the lesion. The distance of regeneration in relation to the rostral lesion border was also markedly increased in the BA-434 treated animal demonstrating that the treatment promotes long-distance regeneration.

Example 21

In Vivo Injection of BA-434-Cy3 and Spinal Cord PTEN Expression

To determine tissue distribution of BA-434 in the spinal cord, a laminectomy was performed in adult Balb-C mice and BA-434 (10 µg-50 µg) was injected into the grey matter of the spinal cord. 24 hr after intraspinal injection the mice were deeply anaesthetized and then transcardially perfused with 4% paraformaldehyde. A 1.5 cm piece of spinal cord comprising the injection site, was dissected from the vertebral column and transferred to 30% sucrose solution. 20 um cryostat sections were prepared and imaged as described in EXAMPLE 17. Sections were immunolabeled with a PTEN antibody as described in EXAMPLE 13.

Figure 31:
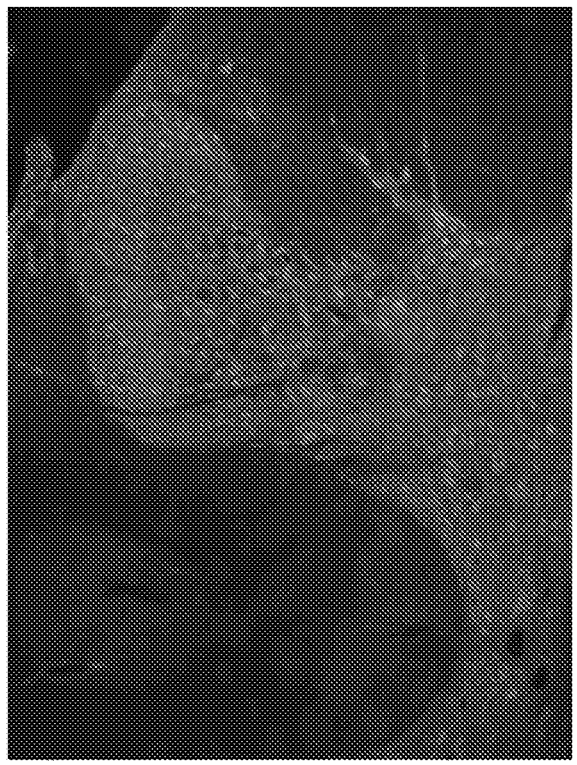
FIG. 31 is a representation of a fluorogram showing a cross section of the rat spinal cord focused on the dorsal portion of the cord stained by immunofluorescence for PTEN protein.
Figure 32A:
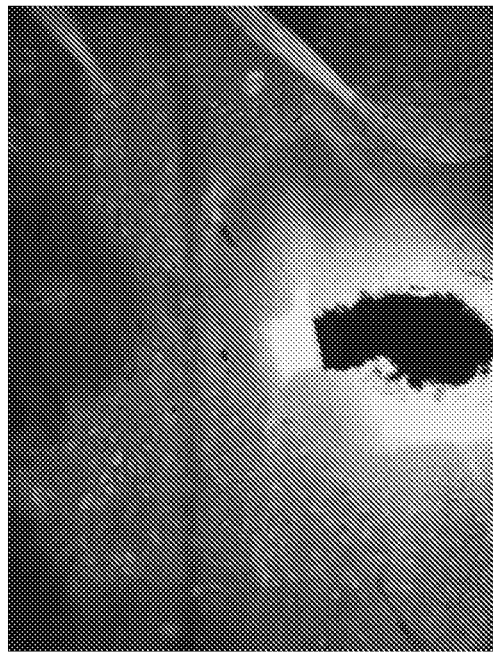
FIG. 32A-32B is a representation of a fluorogram of the cross-sectional plane of a mouse spinal cord 24 hours after intraspinal injection of fluorescently labeled BA-434 where (A) localizes the fluorescent BA-434 sdRNA and (B) is shows immunolabeling for PTEN protein.
Figure 32B:

FIG. 31 shows that neurons in the grey matter of the spinal cord highly express PTEN. Moreover, BA-434 injected directly into the spinal cord (FIG. 32A) is able to spread from the immediate injection site to the surrounding gray matter, which comprises a vast number of PTEN-expressing cells (FIG. 32B) including propriospinal interneurons.

Example 22

Uptake of BA-434 by Neuronal Axons

To determine whether BA-434 is taken up by neuronal axons, E17 cortical neurons were obtained as described in EXAMPLE 10 and plated in microfluidic chambers.

Microfluidic chambers consisted of a cell soma compartment and an axon compartment which are connected by capillary channels with a diameter of 5 µm.

Microfluidic chambers were casted using custom made molds that were filled with polydimethylsiloxane (PDMS) and cured at 60° C. After removal from the molds, PDMS microfluidic chambers were tested for proper sealing and separation of both compartments by adding Trypan blue solution to the axon compartment.

PDL/Laminin pre-coated coverslips (Fisher Scientific, Hampton, N.H.) and E17 rat cortical neurons were plated on the coverslip. 10 days after plating 1 µm of BA-434-Cy3 was added to the axon compartment. 3 days after treatment administration, 4% paraformaldehyde solution was added to each compartment to fix neuronal soma and axons.

Microfluidic chambers were imaged using an epifluorescence microscope. FIG. 33 shows that axons have uptaken BA-434-Cy3. In addition, BA-434-Cy3 fluorescence was detected in the neuronal cell bodies of the soma compartment. These results demonstrate that BA-434 is uptaken by neuronal axons and retrogradely transported to the neuronal soma, suggesting that local delivery of BA-434 to the lesion site is sufficient to silence PTEN gene expression in the axons and the neuronal cell bodies, even if latter are far away from the injury site.

Example 23

Delivery, Dose and Therapeutic Window for Treatment of SCI with sdRNA

To examine the effects of BA-434 on axon regeneration and function recovery after SCI and to validate the clinical route of delivery by direct application to the injured spinal cord during decompression surgery, local delivery in a fibrin or collagen matrix in a rat model of spinal cord injury is used (FIG. 37).

Adult pathogen-free male and female Sprague-Dawley rats (8 weeks) are housed under a 12-h light-dark cycle with free access to water and food. Under isoflurane anesthesia (3-5%), rats are subjected to laminectomy at the level of T9. To do this, the skin is opened and bone removed with rongeurs to expose the T9 spinal cord. The spinal cord is injured by contusion injury using the Infinite Horizon contusion injury device (Precision Systems and Instrumentation because it models human SCI lesions. On the day of surgery, animals are randomized to their respective group.

After contusion injury sdRNA is delivered by injecting the sdRNA into a matrix already FDA-approved for human use. Either an approved fibrin sealant such as Tisseel®, or a collagen matrix, such as Evolence®, is used. Both compounds are sold as pre-filled syringes. The gel is applied to the spinal cord and allowed to polymerize and to control residual bleeding from the surgery. Either directly after the injury, 1 d or 3 d after injury, 5 µL containing about 40 sdRNA is injected into the formed clot, or using a sterile Hamilton syringe. For controls, a non-targeting sdRNA is injected into the matrix after contusion and laminectomy only (sham) animals are used as well. After test compound application, the overlaying muscle and skin are sutured.

Determination of sdRNA diffusion and activity in spinal cord tissue is determined by using Cy-3 fluorescently labeled sdRNA (both BA-434 and NTC). The animals are sacrificed with an overdose of anesthetics and perfused with 0.9% saline followed by perfusion with 4% PFA solution. A 2 cm spinal cord piece, with the lesion site in the center will be dissected from the vertebral column and transferred to 30% sucrose. 30 µm serial longitudinal cryostat sections of the spinal cord are prepared and mounted onto superfrost microscope slides and the area of Cy3 fluorescence will be revealed and measured with epifluorescence microscopy.

To examine efficacy and activity of BA-434 in the rat spinal cord, the biomarkers PTEN, p-S6 and p-AKT are evaluated in spinal cord tissue at different time-points after treatment administration. Western blotting of spinal cord tissue is performed as described in EXAMPLE 13. The animals are sacrificed with an overdose of anesthetics and perfused with 0.9% saline. 3 pieces of spinal cord tissue are collected including the lesion site and the dorsal and ventral regions directly adjacent to the lesion site. After tissue is dissected from vertebral column it is snap frozen with liquid nitrogen.

Tissue samples are processed as described in EXAMPLE 19. Proteins are resolved with SDS-PAGE as described in EXAMPLE 11 and probed with antibodies as described in Example 11.

For anterograde labeling of regenerating CST axons, 4 months after injury, CST fibers are labeled by injection of the anterograde tracer BDA (Molecular Probes, Eugene, Oreg.) into the motor cortex using a 10 µl Hamilton syringe. Approximately 3 µL 10% BDA prepared in saline is injected at 8 sites from each side. The animals are euthanized with anesthetic overdoses 2 weeks later, and perfused transcardially with saline, then 4% paraformaldehyde. The spinal cords are removed and serial longitudinal cryostat sections of the spinal cord are cut at 30 µm thickness and reacted for BDA with avidin-biotin-peroxidase complex or with fluorescent secondary antibodies. Sections are co-labelled with fluorescent antibodies against GAP-43 as described in EXAMPLE 17 to identify regenerating axons. Measurement of axon regeneration is assessed as described in Dergham *J. Neurosc* (2002). 22:6570-6577).

For the demonstrating anatomical spinal cord regeneration and repair, the rats are sacrificed with an overdose of anesthetic and were intracardially perfused with 0.9% saline, followed by phosphate-buffered 4% paraformaldehyde (PFA). Brain and spinal cord (containing also the site of SCI) is extracted from skull and the vertebral column, respectively. CNS tissue is post-fixed in 4% PFA for 2 hr and transferred into a 30% sucrose solution for at least 48 h. Cryostat sections of the PFA-fixed spinal cord piece are prepared. Spinal cord is embedded into tissue molds using Shandon M1 embedding matrix (Thermo Fisher Scientific) and snap-frozen in cold isopentane. 15 µm longitudinal sections of the lesion site and coronal sections of the adjacent rostral and caudal spinal cord regions are obtained using a Leica cryostat, mounted onto Super Frost microscope slides and dried. Sections are permeabilized with 0.1% Triton-X in 1×PBS for 1 hr and subsequently incubated for 1 hr with a blocking solution (5% normal goat serum, 3% BSA in PBS).

Regenerating fibers are detected with fluorescent antibodies against serotonin (to reveal regeneration of raphespinal fibers), PKC-gamma (to reveal regeneration of CST fibers) and GAP43 (to reveal all regenerating fibers). Antibody labeling procedure is performed as described in EXAMPLE 13. Images of the tissue sections are acquired by fluorescent microscopy. The number v, caudal and inside the lesion site will be manually counted by an experimenter blinded to the experimental conditions.

Spinal cord repair and wound healing is revealed by immunolabeling the tissue section with antibodies against the astrocyte marker GFAP. Immunolabeling is performed as described in EXAMPLE 13. The size of the lesion is identified by increased GFAP immunoreactivity of the astroglial scar. Lesion area of every 6th consecutive section will be measured with ImageJ and average area is determined for each animal.

Motor function of control and sdRNA treated rats treated with sdRNA is assessed using a battery of behavioral assays that measure hindlimb locomotor function including the Basso, Beattie, and Bresnahan (BBB) Open Field Locomotor Rating Scale (Basso, et al. (1995) ibid.) and the horizontal ladder. For BBB scoring, rats are evaluated by two observers for 4 min. Locomotion is taped using a video camera by another observer. Hindlimb BBB scores are determined for each animal in a blinded fashion for both hind-limbs and then averaged to obtain the score of each animal. For horizontal ladder animals are video recorded while passing an elevated horizontal with variable spaced ladder rungs and foot slips between the ladder rungs are counted for each animal. The average number of foot slips per animal from two ladder runs will be obtained and used as a measure for voluntary hind limb control.

Delivery of BA-434 locally to the spinal cord lesion site promotes after SCI enhances regeneration and spinal cord repair. Neurons in the spinal cord grey matter highly express PTEN (FIGS. 31 and 32). Stimulation of plasticity in the spinal cord e.g., by enhancing axon sprouting and by stimulating regeneration of injured axon at the lesion site is sufficient to promote functional recovery after SCI. After BA-434 administration to the injury site, PTEN expression in spinal cord interneurons is decreased which correlates with an increased amount of PKC gamma, 5HT and GAP43-positive fibers in and around the lesion, indicating that the treatment induces plasticity of the local circuitry in the spinal cord. In addition, BA-434 local administration to the

Example 24

Prevention of Retinal Ganglion Neuron Loss in a Model of Glaucoma with sdRNA To determine the effects of BA-434 on retinal ganglion neuron survival and functional recovery in the setting of glaucoma (as a model of optic neuropathy), local intravitreal delivery of BA-434 is performed (as also described for FIG. 30B) in a rat model of glaucoma. In this model, injection of hyperosmolar saline solution into the aqueous humor outflow tracts, including the episcleral vessels that drain aqueous humor (Morrison et al. (2008) *Prog. Brain Res.*, 173: 285-301). Five to seven days after saline injection, Tono-Pen measurements show that intraocular pressure is elevated, as occurs in glaucoma.

One week after the procedure to induce an elevation in intraocular pressure in the left eye, BA-434 is injected intravitreally in one cohort as described above in EXAMPLE 18. For a control cohort, NTC is injected intravitreally and another group receives no injection. One to two weeks after sdRNA injection, the animals are perfused transcardially with 4% paraformaldehyde to fix the tissues. Optic nerves are dissected and immersion fixed for an additional 24 hours. They are then embedded in plastic to allow for ultrathin sectioning. Ultrathin cross sections of the optic nerve from the area immediately adjacent to the eye globe are stained using Luxol Fast Blue to identify myelinated axons in the nerve. Counting of the myelinated axons in high power microscopic views show that knockdown of PTEN using BA-434 prevents loss of myelinated axons as compared to the NTC control, thus lessening the nerve loss caused by elevated intraocular pressure. Degenerative changes in the nerve (which only contains axons derived from retinal ganglion cells) are also reduced by BA-434 treatment.

As a companion validation, retinas are removed from the eyes of the BA-434 and NTC treated rats and prepared for flat mount fluorescent microscopy characterization as described in EXAMPLE 18 above. Immunofluorescent histochemistry shows using antibodies against Brn3a identifies all retinal ganglion cells (RGCs) in the flatmount specimen. Counting of the stained cell bodies shows that BA-434 treatment prevents the loss of RGCs in eyes with elevated intraocular pressure, modeling glaucoma, while NTC treatment or no injection show no capacity for preventing loss of RGCs in the retina.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A phosphatase and tensin homolog (PTEN) targeting agent comprising an isolated sdRNA molecule comprising a guide nucleotide strand having a nucleotide sequence comprising SEQ ID NO:5 or SEQ ID NO:7, a passenger strand having a nucleotide sequence comprising SEQ ID NO:6 or SEQ ID NO:8, and a cholesterol-TEG molecule attached at the 3' end of the passenger strand;
the isolated sdRNA molecule comprising a double-stranded region that is 8-15 nucleotides long and a single-stranded region that is 4-12 nucleotides long at the 3' end of the guide nucleotide strand;
wherein at least 40% of the nucleotides of the sdRNA molecule are modified with at least one modification; and wherein the sdRNA molecule does not form a hairpin.

2. The PTEN targeting agent of claim 1, wherein the at least one modification is a phosphorothioate, O-methyl, and/or 2-fluoro modification.

3. The PTEN targeting agent of claim 1, wherein the passenger strand has a nucleotide sequence comprising SEQ ID NO:8 and the guide strand has a nucleotide sequence comprising SEQ ID NO:7.

4. A pharmaceutical composition comprising the PTEN targeting agent of claim 3 and a pharmaceutically acceptable carrier.

5. A method of inhibiting PTEN expression in a mammalian cell, comprising contacting the cell with an amount of PTEN sdRNA molecule such that PTEN mRNA expression is inhibited, wherein the sdRNA molecule comprises a guide nucleotide strand having a nucleotide sequence comprising SEQ ID NO:5 or SEQ ID NO:7, a passenger strand having a nucleotide sequence comprising SEQ ID NO:6 or SEQ ID NO:8, and a cholesterol-TEG molecule attached at the 3' end of the passenger strand;
the isolated sdRNA molecule comprising a double-stranded region that is 8-15 nucleotides long and a single-stranded region that is 4-12 nucleotides long at the 3' end of the guide nucleotide strand;
wherein at least 40% of the nucleotides of the sdRNA molecule are modified with at least one modification; and wherein the sdRNA molecule does not form a hairpin.

6. The method of claim 5, wherein the sdRNA molecule is BA-434 and comprises a passenger sequence comprising SEQ ID NO:8 and a guide sequence comprising SEQ ID NO:7.

7. The method of claim 5, wherein the cell is located in the central nervous system.

8. The method of claim 5, wherein the mammalian cell is a neuronal cell, an astrocyte, or an oligodendrocyte.

9. The method of claim 5, wherein the cell is in the spinal cord.

10. The method of claim 5, wherein the cell is in the retina or optic nerve.

11. A method of treating a CNS injury, comprising contacting the injury with an amount of the PTEN targeting agent of claim 3 effective to promote axon regeneration.

12. A method of treating a CNS injury, comprising contacting the injury with an amount of the PTEN targeting agent of claim 3 effective to promote astrocyte cell migration to, and proliferation at, the injury.

13. The method of claim 11, wherein the CNS injury is a spinal cord injury or an optic neuropathy.

14. The method of claim 11, wherein plasticity of interneurons is promoted at the injury.

15. A method for promoting the survival or regeneration of a mature CNS neuron, the neuron having an axonal injury, the method comprising contacting the injured neuron with a therapeutically effective amount of PTEN sdRNA molecule comprising a guide nucleotide strand having a nucleotide sequence comprising SEQ ID NO:5 or SEQ ID NO:7, a passenger strand having a nucleotide sequence comprising SEQ ID NO:6 or SEQ ID NO:8, and a cholesterol-TEG molecule attached at the 3' end of the passenger strand;
the isolated sdRNA molecule comprising a double-stranded region that is 8-15 nucleotides long and a single-stranded region that is 4-12 nucleotides long at the 3' end of the guide nucleotide strand;
wherein at least 40% of the nucleotides of the sdRNA molecule are modified with at least one modification; and wherein the sdRNA molecule does not form a hairpin.

16. The method of claim 15, wherein the injured neuron is in the spinal cord of a mammalian subject.

* * * * *

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
aaggaccaga gataaaaagg gagt                                           24

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
acctttagct ggcagaccac                                                20

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
caaggactat aaggaacaga acgag                                          25

<210> SEQ ID NO 4
<211> LENGTH: 23
<212> TYPE: DNA
```

```
<213> ORGANISM: Artificial Sequence
<220> FEATURE:
<223> OTHER INFORMATION: Synthetic Construct

<400> SEQUENCE: 4
gaaattcttg attttctcca gca                                              23

<210> SEQ ID NO 5
<211> LENGTH: 15
<212> TYPE: RNA
<213> ORGANISM: Artificial Sequence
<220> FEATURE:
<223> OTHER INFORMATION: Synthetic Construct

<400> SEQUENCE: 5
uagcuaccug uuaaa                                                       15

<210> SEQ ID NO 6
<211> LENGTH: 20
<212> TYPE: RNA
<213> ORGANISM: Artificial Sequence
<220> FEATURE:
<223> OTHER INFORMATION: Synthetic Construct

<400> SEQUENCE: 6
uuuaacaggu agcuauaaua                                                  20

<210> SEQ ID NO 7
<211> LENGTH: 15
<212> TYPE: RNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: 2'-O-methylated adenosine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (11)..(12)
<223> OTHER INFORMATION: um
<220> FEATURE:
<221> NAME/KEY: modified_base
<222> LOCATION: (13)..(15)
<223> OTHER INFORMATION: 2'-O-methylated adenosine

<400> SEQUENCE: 7
uagcuaccug uuaaa                                                       15
```

<210> SEQ ID NO 8
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(3)
<223> OTHER INFORMATION: 2'-fluorinated uridine
<220> FEATURE:
<221> NAME/KEY: modified_base
<222> LOCATION: (6)..(6)
<223> OTHER INFORMATION: 2'-fluorinated cytidine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluorinated uridine
<220> FEATURE:
<221> NAME/KEY: modified_base
<222> LOCATION: (13)..(13)
<223> OTHER INFORMATION: 2'-fluorinated cytidine
<220> FEATURE:
<221> NAME/KEY: modified_base
<222> LOCATION: (14)..(14)
<223> OTHER INFORMATION: 2'-fluorinated uridine
<220> FEATURE:
<221> NAME/KEY: modified_base
<222> LOCATION: (16)..(16)
<223> OTHER INFORMATION: 2'-fluorinated uridine
<220> FEATURE:
<221> NAME/KEY: modified_base
<222> LOCATION: (19)..(19)
<223> OTHER INFORMATION: 2'-fluorinated uridine

<400> SEQUENCE: 8
uuuaacaggu agcuauaaua                                               20

<210> SEQ ID NO 9
<211> LENGTH: 8718
<212> TYPE: DNA
<213> ORGANISM: Homo sapiens

<400> SEQUENCE: 9
cctcccctcg cccggcgcgg tcccgtccgc ctctcgctcg cctcccgcct cccctcggtc     60
ttccgaggcg cccgggctcc cggcgcggcg gcggaggggg cgggcaggcc ggcgggcggt    120
gatgtggcgg gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300 gccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcgcggcgg cacctcccgc tcctggagcg gggggagaa gcggcggcgg    540 cggcggccgc ggcggctgca gctccaggga gggggtctga gtcgcctgtc accatttcca    600
gggctgggaa cgccggagag ttggtctctc cccttctact gcctccaaca cggcggcggc    660

```
ggcggcggca catccaggga cccgggccgg tttaaaccct cccgtccgcc gccgccgcac    720 ccccccgtggc ccgggctccg gaggccgccg gcggaggcag ccgttcggag gattattcgt   780
cttctcccca ttccgctgcc gccgctgcca ggcctctggc tgctgaggag aagcaggccc   840
agtcgctgca accatccagc agccgccgca gcagccatta cccggctgcg gtccagagcc   900
aagcggcggc agagcgaggg gcatcagcta ccgccaagtc cagagccatt ccatcctgc    960 agaagaagcc ccgccaccag cagcttctgc catctctctc ctccttttc ttcagccaca   1020 ggctcccaga catgacagcc atcatcaaag agatcgttag cagaaacaaa aggagatatc   1080
aagaggatgg attcgactta gacttgacct atatttatcc aaacattatt gctatgggat   1140
ttcctgcaga aagacttgaa ggcgtataca ggaacaatat tgatgatgta gtaaggtttt   1200
tggattcaaa gcataaaaac cattacaaga tatacaatct ttgtgctgaa agacattatg   1260
acaccgccaa atttaattgc agagttgcac aatatccttt tgaagaccat aacccaccac   1320
agctagaact tatcaaaccc ttttgtgaag atcttgacca atggctaagt gaagatgaca   1380
atcatgttgc agcaattcac tgtaaagctg aaagggacg aactggtgta atgatatgtg    1440
catatttatt acatcggggc aaattttaa aggcacaaga ggccctagat ttctatgggg     1500
aagtaaggac cagagacaaa aagggagtaa ctattcccag tcagaggcgc tatgtgtatt   1560
attatagcta cctgttaaag aatcatctgg attatagacc agtggcactg ttgtttcaca   1620
agatgatgtt tgaaactatt ccaatgttca gtggcggaac ttgcaatcct cagtttgtgg   1680
tctgccagct aaaggtgaag atatattcct ccaattcagg acccacacga cgggaagaca   1740
agttcatgta ctttgagttc cctcagccgt tacctgtgtg tggtgatatc aaagtagagt   1800
tcttccacaa acagaacaag atgctaaaaa aggacaaaat gtttcacttt tgggtaaata   1860
cattcttcat accaggacca gaggaaaacct cagaaaaagt agaaaatgga agtctatgtg   1920
atcaagaaat cgatagcatt tgcagtatag agcgtgcaga taatgacaag gaatatctag   1980
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc agagaatga accttttgat gaagatcagc    2220
atacacaaat tacaaaagtc tgaatttttt tttatcaaga gggataaaac accatgaaaa    2280
taaacttgaa taaactgaaa atggaccttt ttttttttaa tggcaatagg acattgtgtc   2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat    2460
ataccttttt gtgtcaaaag gacatttaaa attcaattag gattaataaa gatggcactt    2520
tcccgtttta ttccagtttt ataaaaagtg gagacagact gatgtgtata cgtaggaatt     2580
ttttcctttt gtgttctgtc accaactgaa gtggctaaag agcttgtgta tatactggtt      2640
cacatcctac ccctttgcac ttgtggcaac agataagttt gcagttggct aagagaggtt    2700
tccgaagggt tttgctacat tctaatgcat gtattcgggt taggggaatg gagggaatgc    2760
tcagaaagga ataaatttta tgctggactc tggaccatat accatctcca gctatttaca    2820
cacacctttc tttagcatgc tacagttatt aatctggaca ttcgaggaat tggccgctgt   2880
cactgcttgt tgtttgcgca ttttttttta aagcatattg gtgctagaaa aggcagctaa    2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
```

```
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tattttacta    3240
gttttcaatc ataatacctg ctgtggatgc ttcatgtgct gcctgcaagc ttctttttc    3300 tcattaaata taaatatttt tgtaatgctg cacagaaatt ttcaatttga gattctacag    3360
taagcgtttt ttttctttga agatttatga tgcacttatt caatagctgt cagccgttcc    3420
acccttttga ccttacacat tctattacaa tgaattttgc agttttgcac atttttaaa    3480 tgtcattaac tgttagggaa ttttacttga atactgaata catataatgt ttatattaaa    3540
aaggacattt gtgttaaaaa ggaaattaga gttgcagtaa actttcaatg ctgcacacaa    3600
aaaaaagaca tttgattttt cagtagaaat tgtcctacat gtgctttatt gatttgctat    3660
tgaaagaata gggtttttt ttttttttt ttttttttt ttaaatgtgc agtgttgaat    3720
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggtttttt ttttccagaaa tttggtgtct    3900 tcaaattata ccttcacctt gacatttgaa tatccagcca ttttgtttct taatggtata    3960
aaattccatt tcaataact tattggtgct gaaattgttc actagctgtg gtctgaccta    4020
gttaatttac aaatacagat tgaataggac ctactagagc agcatttata gagtttgatg    4080
gcaaatagat taggcagaac ttcatctaaa atattcttag taaataatgt tgacacgttt    4140
tccatacctt gtcagtttca ttcaacaatt tttaaatttt taacaaagct cttaggattt    4200
acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380
ttataaatat tgttctttgt tacaatttcg ggcaccgcat attaaaacgt aactttattg    4440
ttccaatatg taacatggag ggccaggtca taaataatga cattataatg gcttttgca    4500 ctgttattat ttttcctttg gaatgtgaag gtctgaatga gggttttgat tttgaatgtt    4560
tcaatgtttt tgagaagcct tgcttacatt ttatggtgta gtcattggaa atggaaaaat    4620
ggcattatat atattatata tataaatata tattatacat actctcctta ctttatttca    4680
gttaccatcc ccatagaatt tgacaagaat tgctatgact gaaaggtttt cgagtcctaa    4740
ttaaactttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagtgggg ccctgtacca tcccaagtcc    4920
tttgtagctc ctcttgaaca tgtttgccat acttttaaaa gggtagttga ataaatagca    4980
tcaccattct ttgctgtggc acaggttata aacttaagtg gagtttaccg gcagcatcaa    5040
atgtttcagc tttaaaaaat aaaagtaggg tacaagttta atgtttagtt ctagaaattt    5100
tgtgcaatat gttcataacg atggctgtgg ttgccacaaa gtgcctcgtt tacccttaaa    5160
tactgttaat gtgtcatgca tgcagatgga aggggtggaa ctgtgcacta aagtgggggc    5220
tttaactgta gtatttggca gagttgcctt ctacctgcca gttcaaaagt tcaacctgtt    5280
ttcatataga atatatatac taaaaaattt cagtctgtta aacagcctta ctctgattca    5340
gcctcttcag atactcttgt gctgtgcagc agtggctctg tgtgtaaatg ctatgcactg    5400
```

```
aggatacaca aaaataccaa tatgatgtgt acaggataat gcctcatccc aatcagatgt    5460
ccatttgtta ttgtgtttgt taacaaccct ttatctctta gtgttataaa ctccacttaa    5520
aactgattaa agtctcattc ttgtcattgt gtgggtgttt tattaaatga gagtttataa    5580
ttcaaattgc ttaagtccat tgaagtttta attaatgggc agccaaatgt gaatacaaag    5640
ttttcagttt ttttttttcc tgctgtcctt caaagcctac tgtttaaaaa aaaaaaaaaa    5700
aaaaaacatg gcctgagagt agagtatctg tctactcatg tttaattaag gaaaaacact    5760 tattttttagg gctttagtca tcacttcata aattgtataa gcacattaaa tagcgttcta    5820
gtcctgaaaa agtccaagat tcttagaaaa ttgtgcatat ttttattatg acagatgttt    5880
gaagataatt ccccagaatg gatttgatac tttagatttc aattttgtgg cttttgtcta    5940
ttattctgta ctctgccatc agcatatgga aagcttcatt tactcatcat gacttgtgcc    6000
atataaaaat tgatatttcg gaatagtcta aaggactttt tgtacttgaa tttaatcatg    6060
ttgtttctaa tattcttaaa agcttgaaga ctaaagcata tcctttcaac aaagcatagt    6120
aaggtaataa gaaagtgtag tttgtacaag tgttaaaaaa ataaagtaga caatgttaca    6180
gtgggactta ttatttcaag tttacatttt ctccatgtaa ttttttaaaa agtaaatgaa    6240
aaaatgtgca ataatgtaaa atatgaagtg tatgtgtaca cacattttat ttttcggtat    6300
cttgggtata cgtatggttg aaaactatac tggagtctaa aagtattcta atttataaga    6360
agacattttg gtgatgtttg aaaaatagaa atgtgctagt tttgttttta tatcatgtcc    6420
tttgtacgtt gtaatatgag ctggcttggt tcagtaaatg ccatcaccat ttccattgag    6480
aatttaaaac tcaccagtgt ttaatatgca ggcttccaaa ggcttatgaa aaaaatcaag    6540
acccttaaat ctagttaatt tgctgctaac atgaaactct ttggttcttt tattttttgcc    6600 agataattag acacacatct aaagcttagt cttaaatggc ttaagtgtag ctattgatta    6660
gtgctgttgc tagttcagaa agaaatgttt gtgaatggaa acaagaatat tcagtccaaa    6720
ctgttgtaag gacagtacct gaaaaccagg aaacaggata atggaaaaag tcttttaaag    6780
atgaaatgtt ggagccaact ttcttataga attaattgta tgtggctata gaaagcctaa    6840
tgattgttgc ttatttttga gagcatatta ttcttttatg accataatct tgctgttttt    6900
ccatcttcca aaagatcttc cttctaatat gtatatcaga atgtgggtag ccagtcagac    6960
aaattcatat tggttggtag ctttaaaaag tttgtaatgt gaagacagga aaggacaaaa    7020
tagtttgctt tggtggtagt actctggttg ttaagctagg tattttgaga ctacttcccc    7080
atcacaacaa caataaaaata atcactcata atcctatcac ctggagacat agccatcgtt    7140
aatatgttag tgactataca atcatgtttt cttctgtata tccatgtata ttctttaaaa    7200
atgaaattta tactgtacct gatctcaaag cttttttagct tagtatatct gtcatgaatt    7260
tgtaggatgt tccattgcat cagaaaacgg acagtgattt gattactttc taatgccaca    7320
gatgcagatt acatgtagtt attgagaatc cttcgaatt cagtggctta atcatgaatg    7380
tctaaatatt gttgacatta ggatgataca tgtaaattaa agttacattt gtttagcata    7440
gacaagctta acattgtaga tgtttctctt caaaaatcat cttaaacatt tgcatttgga    7500
attgtgttaa atagaatgtg tgaaacactg tattagtaaa cttcatcacc tttctacttc    7560
cttatagttt gaacttttca gttttttgtag ttcccaaaca gttgctcaat ttagagcaaa    7620
ttaatttaac acctgccaaa aaaaggctgc tgttggctta tcagttgtct ttaaattcaa    7680
atgctcatgt gactttatc acatcaaaaa atatttcatt aatgattcac ctttagctct    7740
gaaaattacc gcgtttagta attatagtgg gcttataaaa acatgcaact cttttttgata    7800
```

```
gttatttgag aatttggtg aaaaatattt agctgagggc agtatagaac ttataaacca    7860
atatattgat atttttaaaa catttttaca tataagtaaa ctgccatctt tgagcataac    7920
tacatttaaa aataaagctg catattttta aatcaagtgt ttaacaagaa tttatatttt    7980
ttatttttta aaattaaaaa taattatat ttcctctgtt gcatgaggat tctcatctgt    8040
gcttataatg gttagagatt ttatttgtgt ggaatgaagt gaggcttgta gtcatggttc    8100
tagtgtttca gtttgccaag tctgtttact gcagtgaaat tcatcaaatg tttcagtgtg    8160
gttttctgta gcctatcatt tactggctat ttttttatgt acacctttag gattttctgc    8220
ctactctatc cagttgtcca aatgatatcc tacatttac aaatgccctt tcagtttcta    8280 tttcttttt ccattaaatt gccctcatgt cctaatgtgc agtttgtaag tgtgtgtgtg    8340
tgtgtctgtg tgtgtgtgaa tttgattttc aagagtgcta gacttccaat ttgagagatt    8400
aaataattta attcaggcaa acatttttca ttggaatttc acagttcatt gtaatgaaaa    8460
tgttaatcct ggatgacctt tgacatacag taatgaatct tggatattaa tgaatttgtt    8520
agtagcatct tgatgtgtgt tttaatgagt tattttcaaa gttgtgcatt aaaccaaagt    8580
tggcatactg gaagtgttta tatcaagttc catttggcta ctgatggaca aaaaatagaa    8640
atgccttcct atggagagta ttttccttt aaaaaattaa aaaggttaat tatttttgact    8700 aaaaaaaaaa aaaaaaaa                                                  8718

<210> SEQ ID NO 10
<211> LENGTH: 1212
<212> TYPE: DNA
<213> ORGANISM: Rattus norvegicus

<400> SEQUENCE: 10
atgacagcca tcatcaaaga gatcgttagc agaaacaaaa ggagatatca agaggatgga      60
ttcgacttag acttgaccta tatttatcca aatattattg ctatgggatt tcctgcagaa     120
agacttgaag gtgtatacag gaacaatatt gatgatgtag taaggttttt ggattcaaag     180
cataaaaacc attacaagat atacaatcta tgtgctgaga gacattatga caccgccaaa     240
tttaactgca gagttgcaca gtatcctttt gaagaccata acccaccaca gctagaactt     300
atcaaaccct tttgtgaaga tcttgaccaa tggctaagtg aagacgacaa tcatgttgca     360
gcaattcact gtaaagctgg gaaaggacgg actggtgtaa tgatttgtgc atatttattg     420
catcggggca gttttttaaa ggcacaagag gccctggatt tttatgggga agtaaggacc     480
agagataaaa agggagtaac tattcccagt cagaggcgct atgtatatta ttatagctac     540
ctgttaaaga atcacctgga ttacagacca gtggcactgt tgtttcacaa gatgatgttt     600
gaaactattc caatgttcag tggcggaact tgcaatcccc agtttgtggt ctgccagcta     660
aaggtgaaga tctactcctc caactcagga cccacgcggc gggaggacaa gctcatgtac     720
tttgagttcc ctcagccatt gcctgtgtgt ggtgacatca aagtagagtt cttccacaaa     780
cagaacaaga tgctcaaaaa ggacaaaatg tttcactttt gggtaaatac gttcttcata     840
ccaggaccag aggaaacctc agaaaaagtg gaaaatggaa gtctttgtga tcaggaaatc     900
gatagcattt gtagtataga gcgtgcggat aatgacaagg agtatcttgt gctcaccctg     960
acaaaaaatg atcttgacaa agcaaacaaa gacaaggcca accgatactt ctctccaaat    1020
tttaaggtga agttatactt cacaaaaaca gtagaggagc catcaaatcc agaggctagc    1080
agttcaactt ctgtgactcc agacgttagt gacaatgaac ctgatcatta tagatattct    1140
```

```
gacaccactg actctgatcc agagaatgaa cctttttgatg aagatcagca ttcacaaatt    1200
acaaaagtct ga                                                          1212
```